United States Patent
Chao et al.

(10) Patent No.: US 11,242,386 B2
(45) Date of Patent: Feb. 8, 2022

(54) CEACAM6 CAR IMMUNE CELLS TO TREAT CANCERS

(71) Applicants: HELIX BIOPHARMA CORP., Richmond Hill (CA); NATIONAL RESEARCH COUNCIL OF CANADA, Ottawa (CA)

(72) Inventors: Heman Lap Man Chao, Aurora (CA); Wah Yau Wong, Edmonton (CA); Baomin Tian, Edmonton (CA); Lakshmi Krishnan, Gloucester (CA); Jamshid Tanha, Ottawa (CA); Marni Diane Uger, Richmond Hill (CA)

( * ) Notice: Subject to any disclaimer, the term of this patent is extended or adjusted under 35 U.S.C. 154(b) by 0 days.

(21) Appl. No.: 15/651,692

(22) Filed: Jul. 17, 2017

(65) Prior Publication Data

US 2018/0016337 A1    Jan. 18, 2018

Related U.S. Application Data

(60) Provisional application No. 62/410,581, filed on Oct. 20, 2016, provisional application No. 62/363,541, filed on Jul. 18, 2016.

(51) Int. Cl.
| | |
|---|---|
| C07K 16/28 | (2006.01) |
| C07K 14/705 | (2006.01) |
| C07K 14/47 | (2006.01) |
| C07K 16/30 | (2006.01) |
| A61K 35/17 | (2015.01) |
| A61K 45/06 | (2006.01) |
| C07K 14/725 | (2006.01) |
| C12N 5/0783 | (2010.01) |

(52) U.S. Cl.
CPC .......... *C07K 16/2803* (2013.01); *A61K 35/17* (2013.01); *A61K 45/06* (2013.01); *C07K 14/4748* (2013.01); *C07K 14/7051* (2013.01); *C07K 14/70517* (2013.01); *C07K 14/70521* (2013.01); *C07K 14/70578* (2013.01); *C07K 14/70596* (2013.01); *C07K 16/30* (2013.01); *C07K 16/303* (2013.01); *C07K 16/3015* (2013.01); *C12N 5/0636* (2013.01); *C07K 2317/22* (2013.01); *C07K 2317/24* (2013.01); *C07K 2317/34* (2013.01); *C07K 2317/53* (2013.01); *C07K 2317/565* (2013.01); *C07K 2317/569* (2013.01); *C07K 2319/02* (2013.01); *C07K 2319/03* (2013.01); *C07K 2319/033* (2013.01); *C07K 2319/74* (2013.01); *C12N 2510/00* (2013.01)

(58) Field of Classification Search
None
See application file for complete search history.

(56) References Cited

U.S. PATENT DOCUMENTS

2013/0071414 A1 *   3/2013   Dotti .................... C12N 5/0636
                                                        424/184.1

FOREIGN PATENT DOCUMENTS

| CA | 2813133 A1 | 4/2012 | |
|---|---|---|---|
| JP | 2016520074 A | 7/2016 | |
| WO | 2012/040824 A1 | 4/2012 | |
| WO | 2012040824 A1 | 4/2012 | |
| WO | 2015/069922 A2 | 5/2015 | |
| WO | 2015/095895 A1 | 6/2015 | |
| WO | 2015095895 A1 | 6/2015 | |
| WO | WO-2015095895 A1 * | 6/2015 | ............. A61K 35/17 |
| WO | 2016073381 A1 | 5/2016 | |

OTHER PUBLICATIONS

Stanley et al. (Proc. of the Royal Society of London B 1994, 256: 1-6) (Year: 1994).*
Mátés et al. (Nature Genetics May 3, 2009 41(6): 753-761) (Year: 2009).*
Almagro & Fransson, Frontiers in Bioscience 2008; 13:1619-33 (Year: 2008).*
Arbabi-Ghahroudi, M. (Frontiers in Immunology Nov. 2017, Article 1589, 8: 1-8) (Year: 2017).*
Wah Yau Wong et al. Proceedings of the AACR Special Conference on Tumor Immunology and Immunotherapy; Oct. 20-23, 2016; Boston, MA. Philadelphia (PA): AACR; Cancer Immunol Res 2017; 5(3 Suppl):Abstract nr A74. (Year: 2016).*
International search report dated Sep. 14, 2017 for corresponding PCT application PCT/CA2017/050860.
Chmielewski, Markus, et al. "T Cells That Target Carcinoembryonic Antigen Eradicate Orthotopic Pancreatic Carcinomas Without Inducing Autoimmune Colitis in Mice", Gastroenterology vol. 143. No. 4, pp. 1095-1107, 2012.
Nolan, K.F., et al, "Bypassing Immunization: Optimized Design of 'Designer T Cells' against Carcinoembryonic Antigen (CEA)-expressing Tumors, and Lack of Suppression by Soluble CEA", Clinical Cancer Research vol. 5, pp. 3928-3941, Dec. 1999.
Newick, Kheng, et al, "Chimeric antigen receptor T-cell therapy for solid tumors", Official journal of the Amarican Society of Gene & Cell Therapy, 2016.
Katz, Steven C, et al, "Phase I Hepatic Immunotherapy for Metastases study of intra-arterial chimeric antigen receptor modified T cell therapy for CEA+ liver metastases", Clinical Cancer Research, pp. 3149-3159, Jul. 15, 2015.

(Continued)

*Primary Examiner* — Peter J Reddig
(74) *Attorney, Agent, or Firm* — Nath, Goldberg & Meyer; Tanya E. Harkins

(57) ABSTRACT

A chimeric antigen receptor (CAR) that binds to CEACAM6, an epitope or fragment thereof, or a variant thereof.

22 Claims, 18 Drawing Sheets

Specification includes a Sequence Listing.

(56) References Cited

OTHER PUBLICATIONS

Gill, Saar, et al, "Chimeric antigen receptor T cell therapy: 25 years in the making", Blood Reviews 30, pp. 157-167, 2016.

Dotti, Gianpietro, et al, "Design and Development of Therapies using Chimeric Antigen Receptor-Expressing T Cells", Immunology Review, Jan. 2014.

Beatty, Gregory L, et al, "Chimeric antigen receptor-modified T cells for the treatment of solid tumors: Defining the challenges and next steps", Pharmacology & Theraputics 166, pp. 30-39, Jun. 29, 2016.

Katz, S.C. et al., "Phase I Hepatic Immunotherapy for Metastases study of intra-arterial chimeric antigen receptor modified T cell therapy for CEA+ liver metastases", Clin Cancer Res. Jul. 15, 2015, vol. 21(14): 3149-3159.

Jensen, M.C. et al., "Design and implementation of adoptive therapy with chimeric antigen receptor-modified T cells", NIH-PA Author Manuscript, Jan. 2014, vol. 257(1): 127-144.

Tian, Baomin et al., "Production and Characterization of a Camelid Single Domain Antibody-Urease Enzyme Conjugate for the Treatment of Cancer", Bioconjungate Chemistry, Jun. 17, 2015, vol. 26(6): 1144-55.

Polish Application No. 422231 Search Report dated Jan. 8, 2018, with English translation.

Shirasu, N. et al., "Construction and Molecular Characterization of Human Chimeric T-Cell Antigen Receptors Specific for Carcinoembryonic Antigen", Anticancer Research, 2010, pp. 2731-2738, vol. 30.

Beckman, R. A., Weiner, L. M., & Davis, H. M. (Dec. 11, 2006). Antibody constructs in cancer therapy. Retrieved from https://acsjournals.onlinelibrary.wiley.com/doi/full/10.1002/cncr.22402.

Fujimori, K., Covell, D. G., Fletcher, J. E., & Weinstein, J. N. (Jul. 1990). A Modeling Analysis of Monoclonal Antibody Percolation Through Tumors: A Binding-Site Barrier. Retrieved from http://jnm.snmjournals.org/content/31/7/1191.

Thurber, G. M., Schmidt, M. M., & Wittrup, K. D. (Sep. 2008). Antibody tumor penetration: transport opposed by systemic and antigen-mediated clearance. Retrieved from https://www.ncbi.nlm.nih.gov/pmc/articles/PMC2820307/.

Shirasu, N. et al. "Construction and Molecular Characterization of Human Chimeric T-Cell Antigen Receptors Specific for Carcinoembryonic Antigen", Anticancer Research, vol. 30, p. 2731-2738, 2010.

Jin, Z. et al. "The hyperactive Sleeping Beauty transposase SB100X improves the genetic modiication of T cells to express a chimeric antigen receptor", Gene Therapy, vol. 18, p. 849-856, 2011.

\* cited by examiner

A. Injection #1

B. Injection #2

C. Injection #3

A. Injection #1

B. Injection #2

C. Injection #3

SEQUENCE LISTING

```
<160> NUMBER OF SEQ ID NOS: 11

<210> SEQ ID NO 1
<211> LENGTH: 10
<212> TYPE: PRT
<213> ORGANISM: Artificial Sequence
<220> FEATURE:
<223> OTHER INFORMATION: CDR1

<400> SEQUENCE: 1

Gly Arg Thr Asn Ser Val Tyr Thr Met Gly
1               5                   10

<210> SEQ ID NO 2
<211> LENGTH: 17
<212> TYPE: PRT
<213> ORGANISM: Artificial Sequence
<220> FEATURE:
<223> OTHER INFORMATION: CDR2

<400> SEQUENCE: 2

Ile Met Trp Gly Ala Gly Thr Asn Thr His Tyr Ala Asp Ser Val Lys
1               5                   10                  15

Gly

<210> SEQ ID NO 3
<211> LENGTH: 15
<212> TYPE: PRT
<213> ORGANISM: Artificial Sequence
<220> FEATURE:
<223> OTHER INFORMATION: CDR3

<400> SEQUENCE: 3

Ala Ala Asn Arg Gly Ile Pro Ile Ala Gly Arg Gln Tyr Asp Tyr
1               5                   10                  15

<210> SEQ ID NO 4
```

```
<211> LENGTH: 123
<212> TYPE: PRT
<213> ORGANISM: Artificial Sequence
<220> FEATURE:
<223> OTHER INFORMATION: Antibody binding domain

<400> SEQUENCE: 4

Gln Val Lys Leu Glu Glu Ser Gly Gly Gly Leu Val Gln Ala Gly Gly
1               5                   10                  15

Ser Leu Arg Leu Ser Cys Arg Thr Ser Gly Arg Thr Asn Ser Val Tyr
            20                  25                  30

Thr Met Gly Trp Phe Arg Gln Ala Pro Gly Lys Glu Arg Glu Phe Val
        35                  40                  45

Ala Gln Ile Met Trp Gly Ala Gly Thr Asn Thr His Tyr Ala Asp Ser
    50                  55                  60

Val Lys Gly Arg Phe Thr Ile Ser Arg Asp Ser Ala Glu Ser Thr Val
65                  70                  75                  80

Tyr Leu Gln Met Asn Ser Leu Lys Pro Glu Asp Thr Ala Val Tyr Tyr
                85                  90                  95

Cys Ala Ala Asn Arg Gly Ile Pro Ile Ala Gly Arg Gln Tyr Asp Tyr
            100                 105                 110

Trp Gly Gln Gly Thr Gln Val Thr Val Ser Ser
        115                 120

<210> SEQ ID NO 5
<211> LENGTH: 368
<212> TYPE: PRT
<213> ORGANISM: Artificial Sequence
<220> FEATURE:
<223> OTHER INFORMATION: CAR

<400> SEQUENCE: 5

Met Leu Leu Leu Val Thr Ser Leu Leu Leu Cys Glu Leu Pro His Pro
1               5                   10                  15

Ala Phe Leu Leu Ile Pro Ala Ser Gln Val Lys Leu Glu Glu Ser Gly
            20                  25                  30

Gly Gly Leu Val Gln Ala Gly Gly Ser Leu Arg Leu Ser Cys Arg Thr
        35                  40                  45

Ser Gly Arg Thr Asn Ser Val Tyr Thr Met Gly Trp Phe Arg Gln Ala
    50                  55                  60

Pro Gly Lys Glu Arg Glu Phe Val Ala Gln Ile Met Trp Gly Ala Gly
65                  70                  75                  80

Thr Asn Thr His Tyr Ala Asp Ser Val Lys Gly Arg Phe Thr Ile Ser
                85                  90                  95

Arg Asp Ser Ala Glu Ser Thr Val Tyr Leu Gln Met Asn Ser Leu Lys
            100                 105                 110

Pro Glu Asp Thr Ala Val Tyr Tyr Cys Ala Ala Asn Arg Gly Ile Pro
        115                 120                 125

Ile Ala Gly Arg Gln Tyr Asp Tyr Trp Gly Gln Gly Thr Gln Val Thr
    130                 135                 140

Val Ser Ser Leu Glu Ile Glu Val Met Tyr Pro Pro Pro Tyr Leu Asp
145                 150                 155                 160

Asn Glu Lys Ser Asn Gly Thr Ile Ile His Val Lys Gly Lys His Leu
                165                 170                 175

Cys Pro Ser Pro Leu Phe Pro Gly Pro Ser Lys Pro Phe Trp Val Leu
            180                 185                 190

Val Val Val Gly Gly Val Leu Ala Cys Tyr Ser Leu Leu Val Thr Val
```

```
            195                 200                 205
Ala Phe Ile Ile Phe Trp Val Arg Ser Lys Arg Ser Arg Leu Leu His
210                 215                 220

Ser Asp Tyr Met Asn Met Thr Pro Arg Arg Pro Gly Pro Thr Arg Lys
225                 230                 235                 240

His Tyr Gln Pro Tyr Ala Pro Pro Arg Asp Phe Ala Ala Tyr Arg Ser
                245                 250                 255

Arg Val Lys Phe Ser Arg Ser Ala Asp Ala Pro Ala Tyr Gln Gln Gly
                260                 265                 270

Gln Asn Gln Leu Tyr Asn Glu Leu Asn Leu Gly Arg Arg Glu Glu Tyr
            275                 280                 285

Asp Val Leu Asp Lys Arg Arg Gly Arg Asp Pro Glu Met Gly Gly Lys
    290                 295                 300

Pro Arg Arg Lys Asn Pro Gln Glu Gly Leu Tyr Asn Glu Leu Gln Lys
305                 310                 315                 320

Asp Lys Met Ala Glu Ala Tyr Ser Glu Ile Gly Met Lys Gly Glu Arg
                325                 330                 335

Arg Arg Gly Lys Gly His Asp Gly Leu Tyr Gln Gly Leu Ser Thr Ala
                340                 345                 350

Thr Lys Asp Thr Tyr Asp Ala Leu His Met Gln Ala Leu Pro Pro Arg
            355                 360                 365

<210> SEQ ID NO 6
<211> LENGTH: 10
<212> TYPE: PRT
<213> ORGANISM: Homo sapiens

<400> SEQUENCE: 6

Asn Arg Ile Gly Tyr Ser Trp Tyr Lys Gly
1               5                   10

<210> SEQ ID NO 7
<211> LENGTH: 344
<212> TYPE: PRT
<213> ORGANISM: Homo sapiens

<400> SEQUENCE: 7

Met Gly Pro Pro Ser Ala Pro Pro Cys Arg Leu His Val Pro Trp Lys
1               5                   10                  15

Glu Val Leu Leu Thr Ala Ser Leu Leu Thr Phe Trp Asn Pro Pro Thr
                20                  25                  30

Thr Ala Lys Leu Thr Ile Glu Ser Thr Pro Phe Asn Val Ala Glu Gly
            35                  40                  45

Lys Glu Val Leu Leu Leu Ala His Asn Leu Pro Gln Asn Arg Ile Gly
        50                  55                  60

Tyr Ser Trp Tyr Lys Gly Glu Arg Val Asp Gly Asn Ser Leu Ile Val
65                  70                  75                  80

Gly Tyr Val Ile Gly Thr Gln Gln Ala Thr Pro Gly Pro Ala Tyr Ser
                85                  90                  95

Gly Arg Glu Thr Ile Tyr Pro Asn Ala Ser Leu Leu Ile Gln Asn Val
                100                 105                 110

Thr Gln Asn Asp Thr Gly Phe Tyr Thr Leu Gln Val Ile Lys Ser Asp
            115                 120                 125

Leu Val Asn Glu Glu Ala Thr Gly Gln Phe His Val Tyr Pro Glu Leu
    130                 135                 140

Pro Lys Pro Ser Ile Ser Ser Asn Asn Ser Asn Pro Val Glu Asp Lys
```

```
145                 150                 155                 160
Asp Ala Val Ala Phe Thr Cys Glu Pro Glu Val Gln Asn Thr Thr Tyr
                165                 170                 175

Leu Trp Trp Val Asn Gly Gln Ser Leu Pro Val Ser Pro Arg Leu Gln
                180                 185                 190

Leu Ser Asn Gly Asn Met Thr Leu Thr Leu Ser Val Lys Arg Asn
            195                 200                 205

Asp Ala Gly Ser Tyr Glu Cys Glu Ile Gln Asn Pro Ala Ser Ala Asn
            210                 215                 220

Arg Ser Asp Pro Val Thr Leu Asn Val Leu Tyr Gly Pro Asp Gly Pro
225                 230                 235                 240

Thr Ile Ser Pro Ser Lys Ala Asn Tyr Arg Pro Gly Glu Asn Leu Asn
                245                 250                 255

Leu Ser Cys His Ala Ala Ser Asn Pro Pro Ala Gln Tyr Ser Trp Phe
                260                 265                 270

Ile Asn Gly Thr Phe Gln Gln Ser Thr Gln Glu Leu Phe Ile Pro Asn
            275                 280                 285

Ile Thr Val Asn Asn Ser Gly Ser Tyr Met Cys Gln Ala His Asn Ser
        290                 295                 300

Ala Thr Gly Leu Asn Arg Thr Thr Val Thr Met Ile Thr Val Ser Gly
305                 310                 315                 320

Ser Ala Pro Val Leu Ser Ala Val Ala Thr Val Gly Ile Thr Ile Gly
                325                 330                 335

Val Leu Ala Arg Val Ala Leu Ile
            340

<210> SEQ ID NO 8
<211> LENGTH: 340
<212> TYPE: PRT
<213> ORGANISM: Unknown
<220> FEATURE:
<223> OTHER INFORMATION: SB10 transposase

<400> SEQUENCE: 8

Met Gly Lys Ser Lys Glu Ile Ser Gln Asp Leu Arg Lys Lys Ile Val
1               5                   10                  15

Asp Leu His Lys Ser Gly Ser Ser Leu Gly Ala Ile Ser Lys Arg Leu
                20                  25                  30

Lys Val Pro Arg Ser Ser Val Gln Thr Ile Val Arg Lys Tyr Lys His
            35                  40                  45

His Gly Thr Thr Gln Pro Ser Tyr Arg Ser Gly Arg Arg Arg Val Leu
        50                  55                  60

Ser Pro Arg Asp Glu Arg Thr Leu Val Arg Lys Val Gln Ile Asn Pro
65                  70                  75                  80

Arg Thr Thr Ala Lys Asp Leu Val Lys Met Leu Glu Glu Thr Gly Thr
                85                  90                  95

Lys Val Ser Ile Ser Thr Val Lys Arg Val Leu Tyr Arg His Asn Leu
            100                 105                 110

Lys Gly Arg Ser Ala Arg Lys Lys Pro Leu Leu Gln Asn Arg His Lys
        115                 120                 125

Lys Ala Arg Leu Arg Phe Ala Thr Ala His Gly Asp Lys Asp Arg Thr
    130                 135                 140

Phe Trp Arg Asn Val Leu Trp Ser Asp Glu Thr Lys Ile Glu Leu Phe
145                 150                 155                 160

Gly His Asn Asp His Arg Tyr Val Trp Arg Lys Lys Gly Glu Ala Cys
```

```
                           165                 170                 175
Lys Pro Lys Asn Thr Ile Pro Thr Val Lys His Gly Gly Ser Ile
            180                 185                 190

Met Leu Trp Gly Cys Phe Ala Ala Gly Gly Thr Gly Ala Leu His Lys
        195                 200                 205

Ile Asp Gly Ile Met Arg Lys Glu Asn Tyr Val Asp Ile Leu Lys Gln
    210                 215                 220

His Leu Lys Thr Ser Val Arg Lys Leu Lys Leu Gly Arg Lys Trp Val
225                 230                 235                 240

Phe Gln Met Asp Asn Asp Pro Lys His Thr Ser Lys Val Val Ala Lys
                245                 250                 255

Trp Leu Lys Asp Asn Lys Val Lys Val Leu Glu Trp Pro Ser Gln Ser
            260                 265                 270

Pro Asp Leu Asn Pro Ile Glu Asn Leu Trp Ala Glu Leu Lys Lys Arg
        275                 280                 285

Val Arg Ala Arg Arg Pro Thr Asn Leu Thr Gln Leu His Gln Leu Cys
    290                 295                 300

Gln Glu Glu Trp Ala Lys Ile His Pro Thr Tyr Cys Gly Lys Leu Val
305                 310                 315                 320

Glu Gly Tyr Pro Lys Arg Leu Thr Gln Val Lys Gln Phe Lys Gly Asn
                325                 330                 335

Ala Thr Lys Tyr
            340

<210> SEQ ID NO 9
<211> LENGTH: 1167
<212> TYPE: DNA
<213> ORGANISM: Artificial Sequence
<220> FEATURE:
<223> OTHER INFORMATION: CAR

<400> SEQUENCE: 9
ggatccgccg ccaccatgct tctcctggtg acaagccttc tgctctgtga gttaccacac      60
ccagcattcc tcctgatccc acaggtaaag ctggaggagt ctgggggagg attggtgcag     120 gctggggggct ctctgagact ctcctgtaga acctctggac gcaccaacag tgtctatacc    180
atgggctggt tccgccaggc tccagggaag gagcgtgagt ttgtagcaca aattatgtgg     240
ggtgcaggta ctaacacgca ctatgcagac tccgtgaagg gccgattcac catctccaga     300
gacagcgccg agagcacggt gtacctgcaa atgaacagcc tgaaacctga ggacacggcc     360
gtttattact gtgcagcgaa tcggggaata cctattgctg ccggcaata tgactactgg      420 ggccagggga cccaggtcac cgtctcctca ggcggcggtg gttctagaga aaacctgtat     480
tttcagggca ctcacacatg cccaccgtgc ccagcacctg aactcctggg gggaccgtca     540
gtcttcctct tccccccaaa acccaaggac accctcatga tctcccggac ccctgaggtc     600
acatgcgtgg tggtggacgt gagccacgaa gaccctgagg tcaagttcaa ctggtacgtg     660
gacggcgtgg aggtgcataa tgccaagaca aagccgcggg aggagcagta caacagcacg     720
taccgtgtgg tcagcgtcct caccgtcctg caccaggact ggctgaatgg caaggagtac     780
aagtgcaagg tctccaacaa agccctccca gcccccatcg agaaaaccat ctccaaagcc     840
aaagggcagc ccgagaacc acaggtgtac accctgcccc catcccggga tgagctgacc     900
aagaaccagg tcagcctgac ctgcctggtc aaaggcttct atcccagcga catcgccgtg     960
gagtgggaga gcaatgggca gccggagaac aactacaaga ccacgcctcc cgtgctggac    1020
```

```
tccgacggct ccttcttcct ctacagcaag ctcaccgtgg acaagagcag gtggcagcag    1080
gggaacgtct tctcatgctc cgtgatgcat gaggctctgc acaaccacta cacgcagaag    1140
agcctctccc tgtctcccgg gaaatga                                        1167

<210> SEQ ID NO 10
<211> LENGTH: 1131
<212> TYPE: DNA
<213> ORGANISM: Artificial Sequence
<220> FEATURE:
<223> OTHER INFORMATION: CAR

<400> SEQUENCE: 10
tctagagccg ccaccatgct ctcctggtg acaagccttc tgctctgtga gttaccacac       60
ccagcattcc tcctgatccc agctagccag gtaaagctgg aggagtctgg gggaggattg     120
gtgcaggctg ggggctctct gagactctcc tgtagaacct ctggacgcac caacagtgtc     180
tataccatgg gctggttccg ccaggctcca gggaaggagc gtgagtttgt agcacaaatt     240
atgtggggtg caggtactaa cacgcactat gcagactccg tgaagggccg attcaccatc     300
tccagagaca cgccgagag cacggtgtac ctgcaaatga acagcctgaa acctgaggac     360
acggccgttt attactgtgc agcgaatcgg ggaataccta ttgctggccg gcaatatgac     420
tactggggcc aggggaccca ggtcaccgtc tcctcactcg agattgaagt tatgtatcct     480
cctccttacc tagacaatga aagagcaat ggaaccatta tccatgtgaa agggaaacac     540
ctttgtccaa gtccctatt tcccggacct tctaagccct tttgggtgct ggtggtggtt     600
gggggagtcc tggcttgcta tagcttgcta gtaacagtgg cctttattat tttctgggtg     660
aggagtaaga ggagcaggct cctgcacagt gactacatga acatgactcc ccgccgcccc     720
gggcccaccc gcaagcatta ccagccctat gccccaccac gcgacttcgc agcctatcgc     780
tccagagtga agttcagcag gagcgcagac gccccgcgt accagcaggg ccagaaccag     840
ctctataacg agctcaatct aggacgaaga gaggagtacg atgttttgga caagagacgt     900
ggccgggacc ctgagatggg gggaaagccg agaaggaaga accctcagga aggcctgtac     960
aatgaactgc agaaagataa gatggcggag gcctacagtg agattgggat gaaaggcgag    1020
cgccggaggg gcaaggggca cgatggcctt taccagggtc tcagtacagc caccaaggac    1080
acctacgacg cccttcacat gcaggccctg ccccctcgct aataggaatt c             1131

<210> SEQ ID NO 11
<211> LENGTH: 383
<212> TYPE: PRT
<213> ORGANISM: Artificial Sequence
<220> FEATURE:
<223> OTHER INFORMATION: CAR

<400> SEQUENCE: 11

Met Leu Leu Leu Val Thr Ser Leu Leu Cys Glu Leu Pro His Pro
 1               5                  10                  15

Ala Phe Leu Leu Ile Pro Gln Val Lys Leu Glu Glu Ser Gly Gly Gly
                20                  25                  30

Leu Val Gln Ala Gly Gly Ser Leu Arg Leu Ser Cys Arg Thr Ser Gly
            35                  40                  45

Arg Thr Asn Ser Val Tyr Thr Met Gly Trp Phe Arg Gln Ala Pro Gly
        50                  55                  60

Lys Glu Arg Glu Phe Val Ala Gln Ile Met Trp Gly Ala Gly Thr Asn
 65                  70                  75                  80
```

```
Thr His Tyr Ala Asp Ser Val Lys Gly Arg Phe Thr Ile Ser Arg Asp
                85                  90                  95

Ser Ala Glu Ser Thr Val Tyr Leu Gln Met Asn Ser Leu Lys Pro Glu
            100                 105                 110

Asp Thr Ala Val Tyr Tyr Cys Ala Ala Asn Arg Gly Ile Pro Ile Ala
            115                 120                 125

Gly Arg Gln Tyr Asp Tyr Trp Gly Gln Gly Thr Gln Val Thr Val Ser
        130                 135                 140

Ser Gly Gly Gly Gly Ser Arg Glu Asn Leu Tyr Phe Gln Gly Thr His
145                 150                 155                 160

Thr Cys Pro Pro Cys Pro Ala Pro Glu Leu Leu Gly Gly Pro Ser Val
                165                 170                 175

Phe Leu Phe Pro Pro Lys Pro Lys Asp Thr Leu Met Ile Ser Arg Thr
            180                 185                 190

Pro Glu Val Thr Cys Val Val Val Asp Val Ser His Glu Asp Pro Glu
            195                 200                 205

Val Lys Phe Asn Trp Tyr Val Asp Gly Val Glu Val His Asn Ala Lys
        210                 215                 220

Thr Lys Pro Arg Glu Glu Gln Tyr Asn Ser Thr Tyr Arg Val Val Ser
225                 230                 235                 240

Val Leu Thr Val Leu His Gln Asp Trp Leu Asn Gly Lys Glu Tyr Lys
                245                 250                 255

Cys Lys Val Ser Asn Lys Ala Leu Pro Ala Pro Ile Glu Lys Thr Ile
            260                 265                 270

Ser Lys Ala Lys Gly Gln Pro Arg Glu Pro Gln Val Tyr Thr Leu Pro
            275                 280                 285

Pro Ser Arg Asp Glu Leu Thr Lys Asn Gln Val Ser Leu Thr Cys Leu
290                 295                 300

Val Lys Gly Phe Tyr Pro Ser Asp Ile Ala Val Glu Trp Glu Ser Asn
305                 310                 315                 320

Gly Gln Pro Glu Asn Asn Tyr Lys Thr Thr Pro Pro Val Leu Asp Ser
            325                 330                 335

Asp Gly Ser Phe Phe Leu Tyr Ser Lys Leu Thr Val Asp Lys Ser Arg
            340                 345                 350

Trp Gln Gln Gly Asn Val Phe Ser Cys Ser Val Met His Glu Ala Leu
        355                 360                 365

His Asn His Tyr Thr Gln Lys Ser Leu Ser Leu Ser Pro Gly Lys
        370                 375                 380
```

CEACAM6 CAR IMMUNE CELLS TO TREAT CANCERS

RELATED APPLICATIONS

This application claims priority to U.S. 62/363,541 filed on Jul. 18, 2016 and U.S. 62/410,581 filed on Oct. 20, 2016 (both of which are incorporated herein by reference in their entirety).

"The Sequence Listing submitted in text format (.txt) filed on Jul. 17, 2017, named "Sequence Listing Jul-2017 16010-145_ST25.txt", (created on Jul. 13 2017, 17.6 KB), is incorporated herein by reference."

FIELD OF THE INVENTION

The present invention relates to cancer immunotherapy, more specifically compositions and methods for treating cancer in humans. The invention includes engineered CARs (chimeric receptor antigens) and genetically modified immune cells that express such a CAR with a high affinity for a cancer-associated antigen. More specifically, the cells are CAR-T cells recognizing solid tumor antigens, uses thereof, compositions thereof and methods of making. The invention includes therapeutic methods to treat CEACAM6 dependent cancers.

BACKGROUND OF THE INVENTION

Adoptive cell transfer (ACT) is the transfer of cells into a patient. In particular cases, this involves engineering the patients' own immune cells to recognize and attack their tumor cells. In some approaches, T cells are collected from a subject, genetically engineered to produce special receptors on their surface called chimeric antigen receptors (CARs) that allow the T cells to recognize a specific protein (antigen) on tumor cells. These engineered CAR-T cells are then expanded in the laboratory and reintroduced into the patient where they detect the tumor antigen and promptly activate, triggering their cytotoxic activity, releasing cytokines within the tumor microenvironment and further proliferating. This leads to the killing of the cancer cells that harbor the antigen on their surfaces.

To date, research has focused on the identification and use of non-solid tumor antigens for developing ACT therapies. CD19 antigen is present on the surface of nearly all B cells, both normal and cancerous, making it a good target for treatment of lymphomas. However, for a majority of solid cancers, tumor-specific antigens are not yet well defined making the selection of an antigen target difficult.

Carcinoembryonic antigen related cell adhesion molecule 6 (CEACAM6) is a glycosylphosphoinositol (GPI)-linked cell surface protein and a member of the CEACAM family proteins whose members are glycosyl phosphatidyl inositol (GPI) anchored cell surface glycoproteins. CEACAM6 expression is elevated in many solid tumors such as breast, pancreatic, ovarian, lung, hepatocellular and colon cancer (Blumenthal et al, 2007, BMC Cancer 2007; 7:2.7). Additionally, CEACAM6 over-expression in pancreatic cancer tissues promotes pancreatic cancer cell invasion, metastasis, and angiogenesis, making CEACAM6 a target for pancreatic cancer therapy.

While adoptive cell transfer utilizing CAR cell therapy appears an attractive alternative to surgery, chemotherapy and radiation therapy, treatments have been restricted to small clinical trials and there are issues with respect to the clinical applications thereof. For example, there may be limited in vivo expansion of CAR-T cells, disappearance of the CAR-T cells after infusion and side-effects such as cytokine-release syndrome. Most notably, there may be a widely varying affinity to the target cancer antigen and thus varied clinical activity. Furthermore, CAR-T cells could indiscriminately attack healthy and tumor cells alike, resulting in "on-target, off-tumor toxicity." If the on-target, off-tumor reactivity destroys or damages essential tissues or results in overwhelming cytokine secretion, the side effects of that CAR-T cell therapy may be intolerable. Thus it would be advantageous to develop CAR and CAR cells with high affinities for the target cancer antigen and thus effective treatment for a specific cancer expressing such antigen, where the clinical effectiveness is demonstrated and possible side effects tolerable.

There is an urgent need in the art for compositions, methods of making such compositions and methods for treatment of solid tumors using CARs that recognize CEACAM6 tumor antigens with a specific and desired effective clinical activity. The present invention addresses this need.

SUMMARY OF THE INVENTION

The present invention provides CARs engineered to target solid tumor antigens. The CARs described herein have high affinity for solid tumor antigens. In aspects, the CARs described herein have high affinity for CEACAM6 dependent cancers. The unique specificity of the CARs described herein comes from the use of sdAbs (single domain antibodies) in place of the scFv of an engineered CAR. This provides a higher affinity due to the small size thereof. Such antibodies also have a propensity to refold easily and biophysical stability. In addition, they may recognize epitopes that are inaccessible to conventional antibodies and can be engineered.

In aspects described herein, the sdAbs are camelid single domain antibodies specific for a solid tumor antigen. In aspects, the sdAbs are specific for a CEACAM6 tumor antigen as well as fragments or variants thereof.

In aspects, there are provided immune cells that express the CARs described herein. The immune cells are typically T cells or CIK cells.

In aspects described herein, there are provided methods for making a CAR-T specific for CEACAM6. In aspects, the methods may be viral or non-viral. More specifically, the methods in aspects are non-viral methods comprising transposons.

The present invention provides an isolated nucleic acid sequence encoding a chimeric antigen receptor (CAR), wherein the CAR comprises an antigen binding domain that binds to CEACAM6 as well as variants, fragments and specific epitopes thereof, a transmembrane domain, one or more co-stimulatory signaling region, and a CD3 zeta signaling domain. In one aspect, the nucleic acid sequence encoding a CAR comprises the nucleic acid sequence of SEQ ID NO: 5.

In one aspect, the antigen binding domain in the CAR is an antibody or an antigen-binding fragment thereof. Typically, the antigen-binding fragment is a single domain antibody or fragment thereof.

In one aspect, the antigen binding domain in the CAR binds to a tumor antigen. In one aspect, the tumor antigen is associated with a solid tumor. In yet another aspect, the tumor antigen is selected from the group consisting of CEACAM6, fragments thereof, variants thereof and epitopes thereof.

In one aspect, the co-stimulatory signaling region in the CAR comprises the intracellular domain of a co-stimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, a ligand that specifically binds with CD83, and any combination thereof.

The invention also provides an isolated CAR comprising an antigen binding domain, a transmembrane domain, a co-stimulatory signaling region, and a CD3 zeta signaling domain.

The invention also provides a cell comprising a nucleic acid sequence encoding a CAR, wherein the CAR comprises an antigen binding domain, a transmembrane domain, a costimulatory signaling region, and a CD3 zeta signaling domain.

In one aspect, the immune cell comprising the CAR is selected from the group consisting of a T cell, a Natural Killer (NK) cell, a CIK cell, a cytotoxic T lymphocyte (CTL), and a regulatory T cell.

The invention also provides a vector comprising a nucleic acid sequence encoding a CAR, wherein the CAR comprises an antigen binding domain, a co-stimulatory signaling region, and a CD3 zeta signaling domain.

The invention also provides a method for stimulating a T cell-mediated immune response to a target tissue in a mammal. In one aspect, the method comprises administering to a mammal an effective amount of a cell genetically modified to express a CAR wherein the CAR comprises an antigen binding domain, a co-stimulatory signaling region, and a CD3 zeta signaling domain, wherein the antigen binding domain is selected to specifically recognize the target cell population or tissue.

The invention also includes a method of treating a mammal having a disease, disorder or condition associated with an elevated expression of a CEACAM6 antigen. In one aspect, the method comprises administering to a mammal an effective amount of a cell genetically modified to express a CAR wherein the CAR comprises an antigen binding domain specific for CEACAM6, a co-stimulatory signaling region, and a CD3 zeta signaling domain, thereby treating the mammal.

In one aspect, the cell is an autologous T cell.

In another aspect, the cell is an allogeneic T cell.

In one aspect, the tumor antigen is CEACAM6, variants thereof, fragments thereof and any combination thereof.

The invention also includes a method of generating a persisting population of genetically engineered T cells in a human diagnosed with cancer. In one aspect, the method comprises administering to a human a T cell genetically engineered to express a CAR wherein the CAR comprises an antigen binding domain, a co-stimulatory signaling region, and a CD3 zeta signaling domain, wherein the persisting population of genetically engineered T cells persists in the human for at least one month after administration.

In one aspect, the persisting population of genetically engineered T cells comprises at least one cell selected from the group consisting of a T cell that was administered to the human, a progeny of a T cell that was administered to the human, and a combination thereof.

In one aspect, the persisting population of genetically engineered T cells comprises a memory T cell.

In one aspect, the persisting population of genetically engineered T cells persists in the human for at least three months after administration. In another aspect, the persisting population of genetically engineered T cells persists in the human for at least four months, five months, six months, seven months, eight months, nine months, ten months, eleven months, twelve months, two years, or three years after administration.

The invention also provides a method of expanding a population of genetically engineered T cells in a human diagnosed with cancer. In one aspect, the method comprises administering to a human a T cell genetically engineered to express a CAR wherein the CAR comprises an antigen binding domain specific for CEACAM6, a co-stimulatory signaling region, and a CD3 zeta signaling domain, wherein the administered genetically engineered T cell produces a population of progeny T cells in the human.

In one aspect, the progeny T cells in the human comprise a memory T cell.

In one aspect, the T cell is an autologous T cell or an allogeneic T cell.

In one aspects, the immune cell is a CIK cell, which can be autologous or allogeneic.

In another aspect, the human is resistant to at least one chemotherapeutic agent.

In one aspect, the cancer is any cancer that expresses CEACAM6 as well as variants or epitopes thereof. Such cancers include but may not be limited to pancreas, breast, colorectal, lung, gastric, ovary and bladder.

In one aspect, the population of progeny T cells persists in the human for at least three months after administration. In another aspect, the population of progeny T cells persist in the human for at least four months, five months, six months, seven months, eight months, nine months, ten months, eleven months, twelve months, two years, or three years after administration.

In aspects of the invention is a chimeric antigen receptor (CAR) that binds to CEACAM6, an epitope or fragment thereof, or a variant thereof.

In aspects, the CAR comprises a single domain antibody or a fragment thereof for binding to CEACAM6.

In aspects, the single domain antibody or fragment thereof is of the species Camelidae.

In aspects, the CAR binds to an epitope of CEACAM6 comprising or consisting of the sequence NRIGYSWYKG (SEQ ID NO: 6).

In aspects the CAR comprises a complementarity determining region (CDR) 1 comprising the sequence of GRTNSVYTMG (SEQ ID NO:1); a CDR2 comprising the sequence of IMWGAGTNTHYADSVKG (SEQ ID NO:2); and/or a CDR3 comprising the sequence of AANRGIPIAGRQYDY (SEQ ID NO:3) for binding to CEACAM6.

In aspects the CAR comprises the sequence:
QVKLEESGGGLVQAGGSLRLSCRTSGRTNSVYTMGWFRQAPGKEREFVAQ IMWGAGTNTHYADSVKGRFTISRDSAESTVYLQMNSLKPEDTAVYYCAAN RGIPIAGRQYDYWGQGTQVTVSS (SEQ ID NO: 4), or a sequence at least 90% identical thereto.

In aspects the CAR comprises a spacer molecule, a transmembrane region and one or more cell signaling domains selected from the group consisting of a human CD8-alpha protein, a human CD28 protein, a human CD3-zeta protein, a human FcRy protein, a CD27 protein, an OX40 protein, a human 4-IBB protein, modified versions of any of the foregoing, and any combination of the foregoing.

In aspects the CAR comprises or consists of the sequence:

(SEQ ID NO: 5)
MLLLVTSLLLCELPHPAFLLIPASQVKLEESGGGLVQAGGSLRLSCRTSG

RTNSVYTMGWFRQAPGKEREFVAQIMWGAGTNTHYADSVKGRFTISRDSA

ESTVYLQMNSLKPEDTAVYYCAANRGIPIAGRQYDYWGQGTQVTVSSLEI

EVMYPPPYLDNEKSNGTIIHVKGKHLCPSPLFPGPSKPFWVLVVVGGVLA

-continued

CYSLLVTVAFIIFWVRSKRSRLLHSDYMNMTPRRPGPTRKHYQPYAPPRD

FAAYRSRVKFSRSADAPAYQQGQNQLYNELNLGRREEYDVLDKRRGRDPE

MGGKPRRKNPQEGLYNELQKDKMAEAYSEIGMKGERRRGKGHDGLYQGLS

TATKDTYDALHMQALPPR.

In aspects is an immune cell comprising a CAR as described herein. The cell may be a T cell or a cytokine induced killer (CIK) cell. In aspects the immune cell may further comprise at least a second CAR.

In aspects the immune cell comprises a transposon/transposase system that is optionally hyperactive. In aspects the transposon/transposase system is a Sleeping Beauty transposon/transposase system. In further aspects the transposon/transposase system is the SB100× transposon/transposase system.

In further aspects the CAR immune cell may further comprise a suicide gene.

In further aspects the CAR immune cell is provided as a composition comprising a pharmaceutically carrier, diluent, and/or excipient. The composition may be refrigerated, frozen or thawed.

In aspects of the invention is a nucleic acid molecule encoding a chimeric antigen receptor (CAR), wherein the CAR comprises a CEACAM6 binding moiety and an immune cell activation moiety, wherein the CEACAM6 binding moiety binds to CEACAM6 or a variant or fragment thereof.

In aspects the CEACAM6 binding moiety comprises a monoclonal antibody or an antigen binding portion thereof directed against CEACAM6 or a variant or fragment thereof. In aspects the CEACAM6 binding moiety comprises a variable region of the monoclonal antibody.

In aspects the immune cell activation moiety comprises a T-cell signaling domain of any one or more of the following proteins: a human CD8-alpha protein, a human CD28 protein, a human CD3-zeta protein, a human FcRy protein, a CD27 protein, an OX40 protein, a human 4-1BB protein, and variants or fragments thereof.

In aspects the nucleic acid molecule of the invention comprises the nucleic acid sequence of at least one of SEQ ID NO: 1, SEQ ID NO: 2, SEQ ID NO: 3, SEQ ID NO: 4, and SEQ ID NO:5; and/or which binds to the sequence of SEQ ID NO: 6.

In aspects is a nucleic acid molecule comprising a nucleotide sequence encoding one or both polypeptide chains of a chimeric antigen receptor (CAR), wherein the CAR comprises, in order from N-terminus to C-terminus:

i) an antigen-binding single domain antibody specific for CEACAM6;

ii) a transmembrane domain;

iii) a costimulatory polypeptide, wherein the co-stimulatory polypeptide is a 4-1BB polypeptide and/or an OX-40 polypeptide; and iv) an intracellular signaling domain.

In aspects the first polypeptide comprises a hinge region interposed between the single domain antibody and the transmembrane domain.

In aspects the hinge region is an immunoglobulin IgG hinge region or a hinge derived from CD8.

In aspects the intracellular signaling domain comprises an immunoreceptor tyrosine-based activation motif (ITAM).

In aspects the intracellular signaling domain comprising an ITAM is selected from CD3-zeta and ZAP70.

In aspects the nucleotide sequence is operably linked to a T-cell-specific promoter.

In aspects the nucleotide sequence is operably linked to an NK cell-specific promoter.

In aspects of the invention is a chimeric antigen receptor (CAR) encoded by the nucleic acid sequence as disclosed herein, in aspects the CAR is specific for CEACAM6.

In aspects the CAR of the invention comprises the amino acid sequence of SEQ ID NO: 1, SEQ ID NO: 1, SEQ ID NO: 3, SEQ ID NO: 4, or SEQ ID NO: 5.

In aspects is a vector comprising the nucleic acid molecule as described herein.

In aspects is a host cell expressing the nucleic acid molecule or the CAR as described herein, in aspects the host cell is an immune cell.

In aspects the host cell is selected from the group consisting of a T-cell and a cytokine induced killer CIK cell, and in aspects may further comprise at least a second CAR.

In aspects the host cell may further comprising a transposon/transposase system that is optionally hyperactive, in aspects the transposon/transposase system is the Sleeping Beauty transposon/transposase system. In further aspects the transposon/transposase system is the SB100× transposon/transposase system.

In aspects the host cell may further comprise a suicide gene.

In aspects is a population of cells comprising at least one host cell as described herein.

In aspects is a pharmaceutical composition comprising the immune cell or the host cell as described herein.

In aspects is a method of treating or preventing a CEACAM6-expressing cancer in a mammal, the method comprising administering the immune cell or the host cell as described herein to the mammal in an amount effective to treat or prevent cancer in the mammal. In aspects the tumor is a solid tumor. In aspects the cancer is pancreatic cancer, breast cancer, colorectal cancer, lung cancer, gastric cancer, hepatocellular cancer, ovarian cancer or bladder cancer.

In aspects is a method for decreasing growth or reducing the size of a CEACAM6-expressing tumor in a subject, where the method comprises administering a composition comprising a CAR-T specific for the CEACAM6 antigen.

1. A chimeric antigen receptor (CAR) that binds to CEACAM6, an epitope or fragment thereof, or a variant thereof.

2. The CAR of claim 1, wherein said CAR comprises a single domain antibody or a fragment thereof for binding to CEACAM6.

3. The CAR of claim 2, wherein said single domain antibody or fragment thereof is of the species Camelidae.

4. The CAR of any one of claims 1 to 3, wherein said CAR binds to an epitope of CEACAM6 comprising or consisting of the sequence NRIGYSWYKG (SEQ ID NO: 6).

5. The CAR of any one of claims 1 to 4, wherein said CAR comprises at least one complementarity determining region (CDR) for binding to CEACAM6 selected from CDR1, CDR2 and CDR3, CDR1 comprising the sequence of GRTNSVYTMG (SEQ ID NO:1); CDR2 comprising the sequence of IMWGAGTNTHYADSVKG (SEQ ID NO:2); CDR3 comprising the sequence of AANRGIPIAGRQYDY (SEQ ID NO:3).

6. The CAR of any one of claims 1 to 5, comprising the sequence: QVKLEESGGGLVQAGGSLRLSCRTSGRTNSVYTMGWFRQAPGKEREFVAQ IMWGAGTNTHYADSVKGRFTISRDSAESTVYLQMNSLKPEDTAVYYCAAN RGIPIAGRQYDYWGQGTQVTVSS (SEQ ID NO: 4), or a sequence at least 90% identical thereto.

7. The CAR of any one of claims 1 to 6, comprising a spacer molecule, a transmembrane region and one or more cell signaling domains selected from the group consisting of a human CD8-alpha protein, a human CD28 protein, a human CD3-zeta protein, a human FcRy protein, a CD27 protein, an OX40 protein, a human 4-1BB protein, modified versions of any of the foregoing, and any combination of the foregoing.

8. The CAR of any one of claims 1 to 7, comprising or consisting of the sequence:

```
                                          (SEQ ID NO: 5)
MLLLVTSLLLCELPHPAFLLIPASQVKLEESGGGLVQAGGSLRLSCRTSG

RTNSVYTMGWFRQAPGKEREFVAQIMWGAGTNTHYADSVKGRFTISRDSA

ESTVYLQMNSLKPEDTAVYYCAANRGIPIAGRQYDYWGQGTQVTVSSLEI

EVMYPPPYLDNEKSNGTIIHVKGKHLCPSPLFPGPSKPFWVLVVVGGVLA

CYSLLVTVAFIIFWVRSKRSRLLHSDYMNMTPRRPGPTRKHYQPYAPPRD

FAAYRSRVKFSRSADAPAYQQGQNQLYNELNLGRREEYDVLDKRRGRDPE

MGGKPRRKNPQEGLYNELQKDKMAEAYSEIGMKGERRRGKGHDGLYQGLS

TATKDTYDALHMQALPPR.
```

9. The CAR of any one of claims 1 to 8, wherein the CAR is humanized.

10. An immune cell comprising the CAR of any one of claims 1 to 9.

11. The immune cell of claim 10, wherein said cell is a T cell or a cytokine induced killer (CIK) cell.

12. The immune cell of claim 10 or 11, further comprising at least a second CAR.

13. The immune cell of any one of claims 10 to 12, further comprising a transposon/transposase system that is optionally hyperactive.

14. The immune cell of claim 13, wherein the transposon/transposase system is a Sleeping Beauty transposon/transposase system.

15. The immune cell of claim 13 or 14, wherein the transposon/transposase system is the SB100× transposon/transposase system.

16. The immune cell of any one of claims 10 to 15, further comprising a suicide gene.

17. The immune cell of any one of claims 10 to 16, formulated into a composition comprising a pharmaceutically carrier, diluent, and/or excipient.

18. A nucleic acid molecule encoding a chimeric antigen receptor (CAR), wherein the CAR comprises a CEACAM6 binding moiety and an immune cell activation moiety, wherein the CEACAM6 binding moiety binds to CEACAM6 or a variant or fragment thereof.

19. The nucleic acid molecule of claim 18, wherein the CEACAM6 binding moiety comprises a monoclonal antibody or an antigen binding portion thereof directed against CEACAM6 or a variant or fragment thereof.

20. The nucleic acid molecule of claim 19, wherein the CEACAM6 binding moiety comprises a variable region of the monoclonal antibody.

21. The nucleic acid molecule of any one of claims 18 to 20, wherein the immune cell activation moiety comprises a T-cell signaling domain of any one or more of the following proteins: a human CD8-alpha protein, a human CD28 protein, a human CD3-zeta protein, a human FcRy protein, a CD27 protein, an OX40 protein, a human 4-1BB protein, and variants or fragments thereof.

22. The nucleic acid molecule of any one of claims 18 to 21, which comprises the nucleic acid sequence of at least one of SEQ ID NO: 1, SEQ ID NO: 2, SEQ ID NO: 3, SEQ ID NO: 4, and SEQ ID NO:5; and/or which binds to the sequence of SEQ ID NO: 6.

23. A nucleic acid molecule comprising a nucleotide sequence encoding one or both polypeptide chains of a chimeric antigen receptor (CAR), wherein the CAR comprises, in order from N-terminus to C-terminus:
  i) an antigen-binding single domain antibody specific for CEACAM6;
  ii) a transmembrane domain;
  iii) a costimulatory polypeptide, wherein the co-stimulatory polypeptide is a 4-1BB polypeptide and/or an OX-40 polypeptide; and
  iv) an intracellular signaling domain.

24. The nucleic acid molecule of claim 23, wherein the first polypeptide comprises a hinge region interposed between the single domain antibody and the transmembrane domain.

25. The nucleic acid molecule of claim 24, wherein the hinge region is an immunoglobulin IgG hinge region or a hinge derived from CD8.

26. The nucleic acid of any one of claims 23 to 26, wherein the intracellular signaling domain comprises an immunoreceptor tyrosine-based activation motif (ITAM).

27. The nucleic acid molecule of claim 26, wherein the intracellular signaling domain comprising an ITAM is selected from CD3-zeta and ZAP70.

28. The nucleic acid molecule of any one of claims 23 to 27, wherein the nucleotide sequence is operably linked to a T-cell-specific promoter.

29. The nucleic acid molecule of any one of claims 23 to 28, wherein the nucleotide sequence is operably linked to an NK cell-specific promoter.

30. A chimeric antigen receptor (CAR) encoded by the nucleic acid sequence of any one of claims 20 to 29.

31. The CAR of claim 30, comprising the amino acid sequence of SEQ ID NO: 1, SEQ ID NO: 1, SEQ ID NO: 3, SEQ ID NO: 4, or SEQ ID NO: 5.

32. A vector comprising the nucleic acid molecule of any one of claims 20 to 29.

33. A host cell expressing the nucleic acid molecule of any one of claims 20 to 29 or the CAR of claim 30 or 31.

34. The host cell of claim 33, wherein the host cell is an immune cell.

35. The host cell of claim 34, where the host cell is selected from the group consisting of a T-cell and a cytokine induced killer CIK cell.

36. The host cell of any one of claims 33 to 35, further comprising at least a second CAR.

37. The host cell of any one of claims 33 to 36, further comprising a transposon/transposase system that is optionally hyperactive.

38. The host cell of claim 37, wherein the transposon/transposase system is the Sleeping Beauty transposon/transposase system.

39. The host cell of claim 37 or 38, wherein the transposon/transposase system is the SB100× transposon/transposase system.

40. The host cell of any one of claims 33 to 39, further comprising a suicide gene.

41. A population of cells comprising at least one host cell of any one of claims 33 to 40.

42. A pharmaceutical composition comprising the immune cell of any one of claims 10 to 17 or the host cell of any one of claims 33 to 38.

43. A method of treating or preventing cancer in a mammal, the method comprising administering the immune cell of any one of claims 10 to 17 or the host cell of any one of claims 33 to 40 to the mammal in an amount effective to treat or prevent cancer in the mammal.

44. The method of claim 43, wherein the cancer is a CEACAM6-expressing cancer.

45. The method of claim 43 or 44, wherein the cancer is pancreatic cancer, breast cancer, colorectal cancer, lung cancer, gastric cancer, hepatocellular cancer, ovarian cancer or bladder cancer.

46. The method of any one of claims 43 to 45, further comprising administration of a chemotherapeutic agent.

47. The pharmaceutical composition of claim 42, further comprising a chemotherapeutic agent.

BRIEF DESCRIPTION OF THE DRAWINGS

The following detailed description of typical aspects described herein will be better understood when read in conjunction with the appended drawings. For the purpose of illustrating the invention, there are shown in the drawings aspects which are presently typical. It should be understood, however, that the invention is not limited to the precise arrangements and instrumentalities of the aspects shown in the drawings.

DETAILED DESCRIPTION

Definitions

Figure 1:
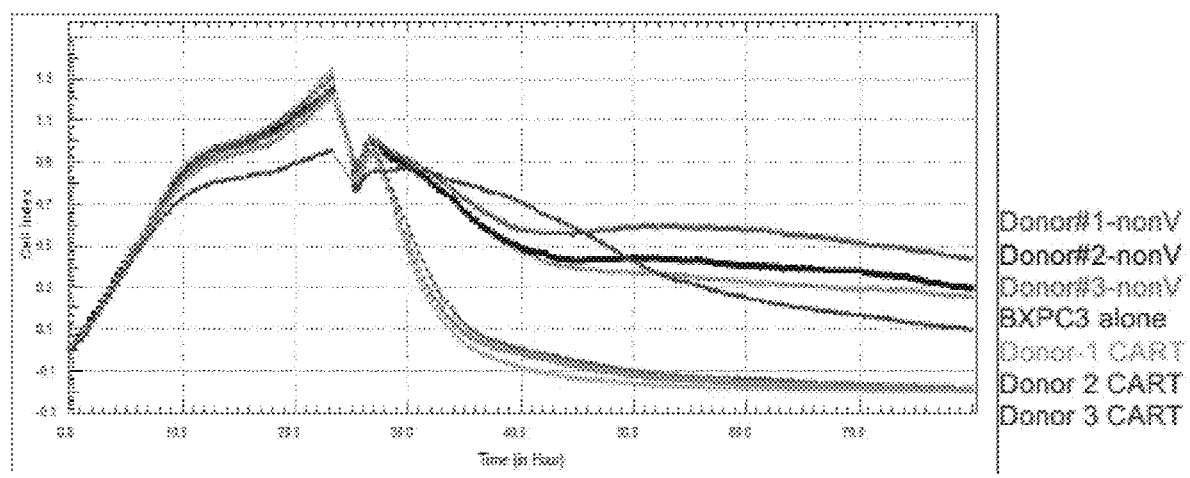
FIG. 1 is a graph showing the increased killing of target cells in the presence of CAR-T cells. RTCA using BXPC3 (CEACAM6 positive) target cells. Effector to target cell ratio was 10:1. Following introduction of effector cells, RTCA data collection proceeded for an additional 56 hours.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the typical materials and methods are described herein. In describing and claiming the present invention, the following terminology will be used.

It is also to be understood that the terminology used herein is for the purpose of describing particular aspects only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more typically±5%, even more typically±1%, and still more typically±0.1% from the specified value, as such variations are appropriate to perform the disclosed methods.

"Activation", as used herein, refers to the state of an immune cell, such as a CIK cell or T cell, that has been sufficiently stimulated to induce detectable cellular proliferation. Activation can also be associated with induced cytokine production, and detectable effector functions. The term "activated T cells" refers to, among other things, T cells that are undergoing cell division.

The term "antibody", also referred to in the art as "immunoglobulin" (Ig), used herein refers to a protein constructed from paired heavy and light polypeptide chains; various Ig isotypes exist, including IgA, IgD, IgE, IgG, and IgM. When an antibody is correctly folded, each chain folds into a number of distinct globular domains joined by more linear polypeptide sequences. For example, the immunoglobulin light chain folds into a variable ($V_L$) and a constant (CO domain, while the heavy chain folds into a variable ($V_H$) and three constant ($C_H$, $C_{H2}$, $C_{H3}$) domains. Interaction of the heavy and light chain variable domains ($V_H$ and $V_L$) results in the formation of an antigen binding region (Fv). Each domain has a well-established structure familiar to those of skill in the art.

The light and heavy chain variable regions are responsible for binding the target antigen and can therefore show significant sequence diversity between antibodies. The constant regions show less sequence diversity, and are responsible for binding a number of natural proteins to elicit important immunological events. The variable region of an antibody contains the antigen binding determinants of the molecule, and thus determines the specificity of an antibody for its target antigen. The majority of sequence variability occurs in six hypervariable regions, three each per variable heavy and light chain; the hypervariable regions combine to form the antigen-binding site, and contribute to binding and recognition of an antigenic determinant. The specificity and affinity of an antibody for its antigen is determined by the structure of the hypervariable regions, as well as their size, shape and chemistry of the surface they present to the antigen. Various schemes exist for identification of the regions of hypervariability, the two most common being those of Kabat and of Chothia and Lesk. Kabat et al (1991a; 1991b) define the "complementarity-determining regions" (CDR) based on sequence variability at the antigen-binding regions of the VH and VL domains. Chothia and Lesk (1987) define the "hypervariable loops" (H or L) based on the location of the structural loop regions in the VH and VL domains. As these individual schemes define CDR and hypervariable loop regions that are adjacent or overlapping, those of skill in the antibody art often utilize the terms "CDR" and "hypervariable loop" interchangeably, and they may be so used herein. For this reason, the regions forming the antigen-binding site are referred to as CDR L1, CDR L2, CDR L3, CDR H1, CDR H2, CDR H3 in the case of antibodies comprising a VH and a VL domain; or as CDR1, CDR2, CDR3 in the case of the antigen-binding regions of either a heavy chain or a light chain. The CDR/loops are referred to herein according to the IMGT numbering system (Lefranc et al., 2003), which was developed to facilitate comparison of variable domains. In this system, conserved amino acids (such as Cys23, Trp41, Cys 104, Phe/Trp 118, and a hydrophobic residue at position 89) always have the same position. Additionally, a standardized delimitation of the framework regions (FR1: positions 1 to 26; FR2: 39 to 55; FR3: 66 to 104; and FR4: 118 to 128) and of the CDR (CDR1: 27 to 38, CDR2: 56 to 65; and CDR3: 105 to 117) is provided.

An "antibody fragment" as referred to herein may include any suitable antigen-binding antibody fragment known in the art. The antibody fragment may be a naturally-occurring antibody fragment, or may be obtained by manipulation of a naturally-occurring antibody or by using recombinant methods. For example, an antibody fragment may include, but is not limited to a Fv, single-chain Fv (scFv; a molecule consisting of $V_L$ and $V_H$ connected with a peptide linker), Fab, F(ab')$_2$, single domain antibody (sdAb; a fragment composed of a single $V_L$ or $V_H$), and multivalent presentations of any of these.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

In a non-limiting example, the antibody fragment may be an sdAb derived from naturally-occurring sources. Heavy chain antibodies of camelid origin (Hamers-Casterman et al, 1993) lack light chains and thus their antigen binding sites consist of one domain, termed $V_{HH}$. sdAb have also been observed in shark and are termed $V_{NAR}$ (Nuttall et al, 2003). Other sdAb may be engineered based on human Ig heavy and light chain sequences (Jespers et al, 2004; To et al, 2005). As used herein, the term "sdAb" includes those sdAb directly isolated from $V_H$, $V_{HH}$, $V_L$, or $V_{NAR}$ reservoir of any origin through phage display or other technologies, sdAb derived from the aforementioned sdAb, recombinantly produced sdAb, as well as those sdAb generated through further modification of such sdAb by humanization, affinity maturation, stabilization, solubilization, e.g., camelization, or other methods of antibody engineering. Also encompassed by the present invention are homologues, derivatives, or fragments that retain the antigen-binding function and specificity of the sdAb.

SdAbs are excellent building blocks for novel antibody molecules due to their high thermostability, high detergent resistance, relatively high resistance to proteases (Dumoulin et al, 2002) and high production yield (Arbabi-Ghahroudi et al, 1997); they can also be engineered to have very high affinity by isolation from an immune library (Li et al, 2009) or by in vitro affinity maturation (Davies & Riechmann, 1996).

A person of skill in the art would be well-acquainted with the structure of a single-domain antibody (see, for example, 3DWT, 2P42 in Protein Data Bank). A sdAb comprises a single immunoglobulin domain that retains the immunoglobulin fold; most notably, only three CDR form the antigen-binding site. However, and as would be understood by those of skill in the art, not all CDR may be required for binding the antigen. For example, and without wishing to be limiting, one, two, or three of the CDR may contribute to binding and recognition of the antigen by the sdAb of the present invention. The CDR of the sdAb or variable domain are referred to herein as CDR1, CDR2, and CDR3, and numbered as defined by Kabat et al (1991b).

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be synthesized or can be derived from a biological sample. Such a biological sample can include, but is not limited to a tissue sample, a tumor sample, a cell or a biological fluid.

The term "anti-tumor effect" or "treatment of cancer" as used herein, refers to a biological effect which can be manifested by a decrease in tumor volume, a decrease in the number of tumor cells, a decrease in the rate of tumor growth, a decrease in the number of metastases, stabilized disease, an increase in life expectancy, or amelioration of various physiological symptoms associated with the cancerous condition. An "anti-tumor effect" can also be manifested by the ability of the peptides, polynucleotides, cells and antibodies described herein in prevention of the occurrence of tumor in the first place.

The term "auto-antigen" means, in accordance with the present invention, any self-antigen which is mistakenly recognized by the immune system as being foreign. Auto-antigens comprise, but are not limited to, cellular proteins, phosphoproteins, cellular surface proteins, cellular lipids, nucleic acids, glycoproteins, including cell surface receptors.

As used herein, the term "autologous" is meant to refer to any material derived from the same individual to which it is later to be re-introduced into the individual.

"Allogeneic" refers to a graft derived from a different animal of the same species.

"Xenogeneic" refers to a graft derived from a different species.

"Syngeneic" refers to a graft derived from an identical individual.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

"Co-stimulatory ligand," as the term is used herein, includes a molecule on an antigen presenting cell (e.g., an aAPC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class I molecule, BTLA and a Toll ligand receptor.

A "co-stimulatory signal", as used herein, refers to a signal, which in combination with a primary signal, such as TCR/CD3 ligation, leads to T cell proliferation and/or upregulation or downregulation of key molecules.

An "effective amount" as used herein, means an amount which provides a therapeutic or prophylactic benefit.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (e.g., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e g, naked or contained in liposomes) and viruses (e.g., lentiviruses, retroviruses, adenoviruses, and adeno-associated viruses) that incorporate the recombinant polynucleotide.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared-.times.100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

A "transposon" or "transposable element" is a DNA sequence that can change its position within a genome, sometimes creating or reversing mutations and altering the cell's genome size. Transposition often results in duplication of the transposon. There are two distinct types of transposon: class II transposons, which consist of DNA that moves directly from place to place; and class I transposons, which are retrotransposons that first transcribe the DNA into RNA and then use reverse transcriptase to make a DNA copy of the RNA to insert in a new location. Transposons typically interact with a transposase, which mediates the movement of the transposon. Non-limiting examples of transposon/transposase systems include Sleeping Beauty, Piggybac, Frog Prince, and Prince Charming.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, typically, a human.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

The term "overexpressed" tumor antigen or "overexpression" of the tumor antigen is intended to indicate an abnormal level of expression of the tumor antigen in a cell from a disease area like a solid tumor within a specific tissue or organ of the patient relative to the level of expression in a normal cell from that tissue or organ. Patients having solid tumors or a hematological malignancy characterized by overexpression of the tumor antigen can be determined by standard assays known in the art.

"Parenteral" administration of an immunogenic composition includes, e.g., subcutaneous (s.c.), intravenous (i.v.), intramuscular (i.m.), or intrasternal injection, or infusion techniques.

The terms "patient," "subject," "individual," and the like are used interchangeably herein, and refer to any animal, or cells thereof whether in vitro or in situ, amenable to the methods described herein.

Moreover, the terms "patient", "subject" and "individual" includes living organisms in which an immune response can be elicited (e.g., mammals). In certain non-limiting aspects, the patient, subject or individual is a mammal and includes humans, dogs, cats, mice, rats, and transgenic species thereof.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-$\beta$, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some aspects, the cells are cultured in vitro. In other aspects, the cells are not cultured in vitro.

As used herein, "treatment" or "therapy" is an approach for obtaining beneficial or desired clinical results. For the purposes described herein, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" and "therapy" can also mean prolonging survival as compared to expected survival if not receiving treatment or therapy. Thus, "treatment" or "therapy" is an intervention performed with the intention of altering the pathology of a disorder. Specifically, the treatment or therapy may directly prevent, slow down or otherwise decrease the pathology of a disease or disorder such as cancer, or may render the cells more susceptible to treatment or therapy by other therapeutic agents.

The term "therapeutic" as used herein means a treatment and/or prophylaxis. A therapeutic effect is obtained by suppression, remission, or eradication of a disease state.

The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

To "treat" a disease as the term is used herein, means to reduce the frequency or severity of at least one sign or symptom of a disease or disorder experienced by a subject.

Moreover, a treatment regime of a subject with a therapeutically effective amount may consist of a single administration, or alternatively comprise a series of applications. The length of the treatment period depends on a variety of factors, such as the severity of the disease, the age of the subject, the concentration of the agent, the responsiveness of the patient to the agent, or a combination thereof. It will also be appreciated that the effective dosage of the agent used for the treatment may increase or decrease over the course of a particular treatment regime. Changes in dosage may result and become apparent by standard diagnostic assays known in the art. The antibodies described herein may, in aspects, be administered before, during or after treatment with conventional therapies for the disease or disorder in question, such as cancer.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

Ranges: throughout this disclosure, various aspects described herein can be presented in a range format. It should be understood that the description in range format is merely for convenience and brevity and should not be construed as an inflexible limitation on the scope described herein. Accordingly, the description of a range should be considered to have specifically disclosed all the possible subranges as well as individual numerical values within that range. For example, description of a range such as from 1 to 6 should be considered to have specifically disclosed subranges such as from 1 to 2, 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

It will be understood that any aspects described as "comprising" certain components may also "consist of" or "consist essentially of," wherein "consisting of" has a closed-ended or restrictive meaning and "consisting essentially of" means including the components specified but excluding other components except for materials present as impurities, unavoidable materials present as a result of processes used to provide the components, and components added for a purpose other than achieving the technical effect described herein. For example, a composition defined using the phrase "consisting essentially of" encompasses any known pharmaceutically acceptable additive, excipient, diluent, carrier, and the like. Typically, a composition consisting essentially of a set of components will comprise less than 5% by weight, typically less than 3% by weight, more typically less than 1% by weight of non-specified components.

It will be understood that any component defined herein as being included may be explicitly excluded from the claimed invention by way of proviso or negative limitation.

Administration "in combination with" one or more further therapeutic agents includes simultaneous (concurrent) and consecutive administration in any order.

The term "pharmaceutically acceptable" means that the compound or combination of compounds is compatible with the remaining ingredients of a formulation for pharmaceutical use, and that it is generally safe for administering to humans according to established governmental standards, including those promulgated by the United States Food and Drug Administration.

The term "pharmaceutically acceptable carrier" includes, but is not limited to solvents, dispersion media, coatings, antibacterial agents, antifungal agents, isotonic and/or absorption delaying agents and the like. The use of pharmaceutically acceptable carriers is well known.

Isolated: An "isolated" biological component (such as a protein) has been substantially separated or purified away from other biological components in the cell of the organism in which the component naturally occurs, i.e., chromosomal and extra-chromosomal DNA and RNA, other proteins and organelles. Proteins and peptides that have been "isolated" include proteins and peptides purified by standard purification methods. The term also includes proteins and peptides prepared by recombinant expression in a host cell, as well as chemically synthesized proteins and peptides.

"Tumour", as used herein, refers to all neoplastic cell growth and proliferation, whether malignant or benign, and all pre-cancerous and cancerous cells and tissues.

The terms "cancer" and "cancerous" refer to or describe the physiological condition in mammals that is typically characterized by unregulated cell growth. The cancer to be treated may be any type of malignancy and, in an aspect, is lung cancer, including small cell lung cancer and non-small cell lung cancer (e.g. adenocarcinoma), pancreatic cancer, colon cancer (e.g. colorectal carcinoma, such as, for example, colon adenocarcinoma and colon adenoma), oesophageal cancer, oral squamous carcinoma, tongue carcinoma, gastric carcinoma, liver cancer, nasopharyngeal cancer, hematopoietic tumours of lymphoid lineage (e.g. acute lymphocytic leukemia, B-cell lymphoma, Burkitt's lymphoma), non-Hodgkin's lymphoma (e.g. mantle cell lymphoma), Hodgkin's disease, myeloid leukemia (for example, acute myelogenous leukemia (AML) or chronic myelogenous leukemia (CML)), acute lymphoblastic leukemia, chronic lymphocytic leukemia (CLL), thyroid follicular cancer, myelodysplastic syndrome (MDS), tumours of mesenchymal origin, soft tissue sarcoma, liposarcoma, gastrointestinal stromal sarcoma, malignant peripheral nerve sheath tumour (MPNST), Ewing sarcoma, leiomyosarcoma, mesenchymal chondrosarcoma, lymphosarcoma, fibrosarcoma, rhabdomyosarcoma, melanoma, teratocarcinoma, neuroblastoma, brain tumours, medulloblastoma, glioma, benign tumour of the skin (e.g. keratoacanthoma), breast carcinoma (e.g. advanced breast cancer), kidney carcinoma, nephroblastoma, ovary carcinoma, cervical carcinoma, endometrial carcinoma, bladder carcinoma, prostate cancer, including advanced disease and hormone refractory prostate cancer, testicular cancer, osteosarcoma, head and neck cancer, epidermal carcinoma, multiple myeloma (e.g. refractory multiple myeloma), or mesothelioma. In an aspect, the cancer cells are derived from a solid tumour. Typically, the cancer cells are derived from a breast cancer, colorectal cancer, melanoma, ovarian cancer, pancreatic cancer, gastric cancer, lung cancer, or prostate cancer. More typically, the cancer cells are derived from a prostate cancer, a lung cancer, a breast cancer, or a melanoma.

A "chemotherapeutic agent" is a chemical compound useful in the treatment of cancer. Examples of chemotherapeutic agents include alkylating agents such as thiotepa, CYTOXAN™ cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins such as bullatacin and bullatacinone; camptothecins such as topotecan; bryostatin; callystatin; CC-1065 and its adozelesin, carzelesin and bizelesin synthetic analogues; cryptophycins such as cryptophycin 1 and cryptophycin 8; dolastatin; duocarmycins such as the synthetic analogues KW-2189 and CB1-TM1; eleutherobin; pancratistatin; sarcodictyins; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimustine; antibiotics such as the enediyne antibiotics, for example calicheamicin, especially calicheamicin gammall and calicheamicin omegall, dynemicin, including dynemicin A, bisphosphonates, such as clodronate, esperamicins, neocarzinostatin chromophore and related chromoprotein enediyne antibiotic chromophores; aclacinomysins; actinomycin; authramycin; azaserine; bleomycins; cactinomycin; carabicin; carminomycin; carzinophilin; chromomycins; dactinomycin; daunorubicin; detorubicin; 6-diazo-5-oxo-L-norleucine; ADRIAMYCIN™ doxorubicin, including morpholino-doxorubicin, cyanomorpholino-doxorubicin, 2-pyrrolino-doxorubicin and deoxydoxorubicin; epirubicin; esorubicin; idarubicin; marcellomycin; mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, and zorubicin; antimetabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, and thioguanine; pyrimidine analogs such as ancitabine, azacitidine, 6-azauridine, carmofur, cytarabine, dideoxyuridine, doxifluridine, enocitabine, and floxuridine; androgens such as calusterone, dromostanolone propionate, epitiostanol, mepitiostane, and testolactone; anti-adrenals such as aminoglutethimide, mitotane, and trilostane; folic acid replenishers such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; epothilones; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK™ polysaccharide complex; razoxane; rhizoxin; sizofiran; spirogermanium; tenuazonic acid; triaziquone; 2,2',2"-trichlorotriethylamine; trichothecenes such as T-2 toxin, verracurin A, roridin A and anguidine; urethan; vindesine; dacarbazine; mannomustine; mitobronitol; mitolactol; pipobroman; gacytosine; arabinoside ("Ara-C"); taxoids, such as TAXOL™ paclitaxel, ABRAXANE™ Cremophor-free, albumin-engineered nanoparticle formulation of paclitaxel, TAXOTERE™ and doxetaxel; chloranbucil; GEMZAR™ gemcitabine; 6-thioguanine; mercaptopurine; methotrexate; platinum coordination complexes such as cisplatin, oxaliplatin and carboplatin; vinblastine; platinum; etoposide (VP-16); ifosfamide; vincristine; NAVELBINE™ vinorelbine; novantrone; teniposide; edatrexate; daunomycin; aminopterin; xeloda; ibandronate; irinotecans such as CPT-11; topoisomerase inhibitors such as RFS 2000; difluoromethylornithine (DMFO); retinoids such as retinoic acid; capecitabine; and pharmaceutically acceptable salts, acids or derivatives of any of the above.

Also included in this definition are anti-hormonal agents that act to regulate or inhibit hormone action on tumours such as anti-estrogens and selective estrogen receptor modulators (SERMs), including, for example, tamoxifen (including NOLVADEX™ tamoxifen), raloxifene, droloxifene, 4-hydroxytamoxifen, trioxifene, keoxifene, LY117018, onapristone, and FARESTON toremifene; aromatase inhibitors that inhibit the enzyme aromatase, which regulates estrogen production in the adrenal glands, such as, for example, 4(5)-imidazoles, aminoglutethimide, MEGASE™ megestrol acetate, AROMASIN™ exemestane, formestane, fadrozole, RIVISOR™ vorozole, FEMARA™ letrozole, and ARIMIDEX™ anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those that inhibit expression of genes in signalling pathways implicated in aberrant cell proliferation, such as, for example, PKC-alpha, Ralf and H-Ras; ribozymes such as a VEGF expression inhibitor (e.g., ANGIOZYME™ ribozyme) and a HER2 expression inhibitor; antibodies such as an anti-VEGF antibody (e.g., AVASTIN™ antibody); vaccines such as gene therapy vaccines, for example, ALLOVECTIN™ vaccine, LEUVECTIN™ vaccine, and VAXID™ vaccine; PROLEUKIN™ rIL-2; LURTOTECAN™ topoisomerase 1 inhibitor; ABARELIX™ rmRH; and pharmaceutically acceptable salts, acids or derivatives of any of the above.

In aspects, the antibodies described herein act additively or synergistically with other conventional anti-cancer treatments.

Many patent applications, patents, and publications are referred to herein to assist in understanding the aspects described. Each of these references are incorporated herein by reference in their entirety.

The invention relates to compositions and methods for treating cancer, in aspects solid tumors. The present invention relates to a strategy of adoptive cell transfer of immune cells transduced to express a chimeric antigen receptor (CAR). CARs are molecules that combine antibody-based specificity for a desired antigen (e.g., tumor antigen) with a T cell receptor-activating intracellular domain to generate a chimeric protein that exhibits a specific anti-tumor cellular immune activity. The gene-modified T cell therapy comprises introducing a nucleic acid encoding a chimeric antigen receptor (CAR) into a T cell, wherein the CAR has specificity for a surface antigen of a tumor cell and ability to activate a T cell, growing ex vivo the gene-introduced T cell thus obtained, and then transfusing the cell into a patient.

The present invention relates generally to the use of such T cells genetically modified to stably express a CAR specific for solid tumor antigens, more specifically, solid tumors expressing the CEACAM6 antigen, fragments, and/or epitopes thereof and variants of these. T cells expressing a CAR are referred to herein as CAR-T cells or CAR modified T cells. In aspects of the present invention, the T cell is genetically modified to stably express a CAR that combines an antigen recognition domain of a sdAb specific for CEACAM6 with one or more intracellular costimulatory domains and signalling domains into a single chimeric protein.

Chimeric Antigen Receptor (CAR)

In one aspect, engineered CARs are described herein. The CAR comprises a CEACAM6 binding moiety that binds to CEACAM6, an epitope thereof, a fragment thereof, or variants of the aforementioned and further comprises an immune cell activation domain. When expressed by an immune cell, the CEACAM6 binding moiety is or is part of an extracellular domain and the immune cell activation domain is or is part of an intracellular signaling domain, typically of the T cell antigen receptor complex zeta chain (e.g., CD3 zeta). Co-stimulatory signaling regions may also be included in the intracellular domain and are cell surface molecules other than antigens receptors or their ligands that are required for an efficient response of lymphocytes to antigen. A spacer moiety (also referred to as a hinge moiety) is typically included in the extracellular domain to allow the CEACAM6 binding moiety to efficiently bind to its epitope. The intracellular and extracellular domains are linked through a transmembrane domain that crosses the cytoplasmic membrane.

A representative non-limiting structure of the CAR of the invention comprises a single domain antibody recognizing a CEACAM6 surface antigen of a tumor cell, a transmembrane domain, and an intracellular domain of a TCR complex CD3 that activates a T cell (called a first generation CAR). The nucleic acid sequence of such a single domain antibody may be obtained by a variety of methods as is understood by one of skill in the art. A T cell expressing a CAR directly recognizes a surface antigen of a tumor cell independently of the expression of major histocompatibility antigen class I on the tumor cell, and at the same time, activates the T cell, and thereby the CAR-expressing T cell can efficiently kill the tumor cell.

For enhancing the ability of the first generation CAR to activate a T cell, a second generation CAR can be made whereby an intracellular domain of CD28 which is a co-stimulatory molecule of a T cell is linked to the first generation CAR. A third generation CAR may also be made whereby an intracellular domain derived from (for example) CD137 (4-1BB) or CD134 (OX40) which is a tumor necrosis factor (TNF) receptor superfamily is tandemly linked to a first generation CAR. Thus, many CAR molecules targeting CEACAM6 are included in the present invention.

CEACAM6 Binding Moiety

In typical aspects, the CAR described herein is specific for carcinoembryonic antigen related cell adhesion molecule 6 (CEACAM6), fragments thereof, epitopes thereof and variants of any of the foregoing. CEACAM6 is also known in the art as non-specific cross-reacting antigen (NCA) or CD66c. The CEACAM6 binding moiety of the invention is such that it binds with a desired affinity to CEACAM6 harbored on a cell/tumor surface leading to activation of the immune cell in which it is provided, to trigger cytotoxic activity and release cytokines within the tumor microenvironment ad further proliferating.

The sequence of CEACAM6 may be, but is not limited to SEQ ID NO: 7, or a sequence substantially identical thereto. Sequences sharing 80% or more identity may also be encompassed.

SEQ ID NO: 7:
MGPPSAPPCRLHVPWKEVLLTASLLTFWNPPTTAKLTIESTPFNVAEGKE

VLLLAHNLPQNRIGYSWYKGERVDGNSLIVGYVIGTQQATPGPAYSGRET

IYPNASLLIQNVTQNDTGFYTLQVIKSDLVNEEATGQFHVYPELPKPSIS

SNNSNPVEDKDAVAFTCEPEVQNTTYLWWVNGQSLPVSPRLQLSNGNMTL

TLLSVKRNDAGSYECEIQNPASANRSDPVTLNVLYGPDGPTISPSKANYR

PGENLNLSCHAASNPPAQYSWFINGTFQQSTQELFIPNITVNNSGSYMCQ

AHNSATGLNRTTVTMITVSGSAPVLSAVATVGITIGVLARVALL

In particular aspects, the antibody and/or epitope may be that described in U.S. Pat. No. 9,066,986, which is incorporated herein by reference in its entirety. Specifically, the CEACAM6 binding domain may comprise the 2A3 anti-CEACAM6 antibody or a fragment or variant thereof. Without wishing to be bound by theory, it is believed that this antibody/epitope interaction has an advantageous level of affinity (not too high and not too low), such that the antibody can bind the epitope on a first cell and activate cell killing, then move on to bind a further epitope on a second or further cell and activate further cell killing.

Thus, also described herein is a CAR comprising, within the CEACAM6 binding moiety a complementarity determining region (CDR) 1 comprising the sequence of GRTNSVYTMG (SEQ ID NO:1); a CDR2 comprising the sequence of IMWGAGTNTHYADSVKG (SEQ ID NO:2); and a CDR3 comprising the sequence of AANRGIPIAGRQYDY (SEQ ID NO:3), wherein the antibody or fragment thereof is specific for CEACAM6. The CEACAM6 binding moiety as just described may recognize and bind to an epitope comprising or consisting of the sequence NRIGYSWYKG (SEQ ID NO:6).

In a specific, non-limiting example, the antibody or fragment thereof may comprise the sequence of SEQ ID NO: 4 or a sequence substantially identical thereto.

SEQ ID NO: 4:
QVKLEESGGGLVQAGGSLRLSCRTSGRTNSVYTMGWFRQAPGKEREFVAQ

IMWGAGTNTHYADSVKGRFTISRDSAESTVYLQMNSLKPEDTAVYYCAAN

RGIPIAGRQYDYWGQGTQVTVSS.

The terms "antibody" and "antibody fragment" ("fragment thereof") are as defined above. As previously stated, the antibody or fragment thereof may be an sdAb. The sdAb may be of camelid origin (e.g., from the species Camelidae) or be derived from a camelid $V_{HH}$, and thus may be based on camelid framework regions; alternatively, the CDR described above may be grafted onto $V_{NAR}$, $V_{HH}$ or $V_L$ framework regions. In yet another alternative, the hypervariable loops described above may be grafted onto the framework regions of other types of antibody fragments (Fv, scFv, Fab).

The present aspect further encompasses an antibody fragment that is "humanized" using any suitable method known in the art, for example, but not limited to CDR grafting and veneering. Humanization of an antibody or antibody fragment comprises replacing an amino acid in the sequence with its human counterpart, as found in the human consensus sequence, without loss of antigen-binding ability or specificity; this approach reduces immunogenicity of the antibody or fragment thereof when introduced into human subjects. In the process of CDR grafting, one or more than one of the heavy chain CDR defined herein may be fused or grafted to a human variable region ($V_H$, or $V_L$), or to other human antibody fragment framework regions (Fv, scFv, Fab). In such a case, the conformation of said one or more than one hypervariable loop is preserved, and the affinity and specificity of the sdAb for its target (i.e., toxins A and B) is also preserved.

CDR grafting is described in at least the following: U.S. Pat. Nos. 6,180,370, 5,693,761, 6,054,297, 5,859,205, and European Patent No. 626390 (the disclosures of which are hereby incorporated by reference in their entirety). Veneering, also referred to in the art as "variable region resurfacing", involves humanizing solvent-exposed positions of the antibody or fragment; thus, buried non-humanized residues, which may be important for CDR conformation, are preserved while the potential for immunological reaction against solvent-exposed regions is minimized. Veneering is described in at least the following: U.S. Pat. Nos. 5,869,619, 5,766,886, 5,821,123, and European Patent No. 519596 (the disclosures of which are hereby incorporated by reference in their entirety). Persons of skill in the art would be amply familiar with methods of preparing such humanized antibody fragments.

A substantially identical sequence may comprise one or more conservative amino acid mutations. It is known in the art that one or more conservative amino acid mutations to a reference sequence may yield a mutant peptide with no substantial change in physiological, chemical, or functional properties compared to the reference sequence; in such a case, the reference and mutant sequences would be considered "substantially identical" polypeptides. Conservative amino acid mutation may include addition, deletion, or substitution of an amino acid; a conservative amino acid substitution is defined herein as the substitution of an amino acid residue for another amino acid residue with similar chemical properties (e.g. size, charge, or polarity).

In a non-limiting example, a conservative mutation may be an amino acid substitution. Such a conservative amino acid substitution may substitute a basic, neutral, hydrophobic, or acidic amino acid for another of the same group. By the term "basic amino acid" it is meant hydrophilic amino acids having a side chain pK value of greater than 7, which are typically positively charged at physiological pH. Basic amino acids include histidine (His or H), arginine (Arg or R), and lysine (Lys or K). By the term "neutral amino acid" (also "polar amino acid"), it is meant hydrophilic amino acids having a side chain that is uncharged at physiological pH, but which has at least one bond in which the pair of electrons shared in common by two atoms is held more closely by one of the atoms. Polar amino acids include serine (Ser or S), threonine (Thr or T), cysteine (Cys or C), tyrosine (Tyr or Y), asparagine (Asn or N), and glutamine (Gln or Q). The term "hydrophobic amino acid" (also "non-polar amino acid") is meant to include amino acids exhibiting a hydrophobicity of greater than zero according to the normalized consensus hydrophobicity scale of Eisenberg (1984). Hydrophobic amino acids include proline (Pro or P), isoleucine (Ile or I), phenylalanine (Phe or F), valine (Val or V), leucine (Leu or L), tryptophan (Trp or W), methionine (Met or M), alanine (Ala or A), and glycine (Gly or G). "Acidic amino acid" refers to hydrophilic amino acids having a side chain pK value of less than 7, which are typically negatively charged at physiological pH. Acidic amino acids include glutamate (Glu or E), and aspartate (Asp or D).

Sequence identity is used to evaluate the similarity of two sequences; it is determined by calculating the percent of residues that are the same when the two sequences are aligned for maximum correspondence between residue positions. Any known method may be used to calculate sequence identity; for example, computer software is available to calculate sequence identity. Without wishing to be limiting, sequence identity can be calculated by software such as NCBI BLAST2 service maintained by the Swiss Institute of Bioinformatics (and as found at ca.expasy.org/tools/blast/), BLAST-P, Blast-N, or FASTA-N, or any other appropriate software that is known in the art.

The substantially identical sequences of the present invention may be at least 85% identical; in another example, the substantially identical sequences may be at least 70, 75, 80, 85, 90, 95, 96, 97, 98, 99, or 100% (or any percentage therebetween) identical at the amino acid level to sequences described herein. Importantly, the substantially identical sequences retain the activity and specificity of the reference sequence. In a non-limiting aspect, the difference in sequence identity may be due to conservative amino acid mutation(s).

The single domain antibody or fragment thereof of the present invention may also comprise additional sequences to aid in expression, detection or purification of a recombinant antibody or fragment thereof. Any such sequences or tags known to those of skill in the art may be used. For example, and without wishing to be limiting, the antibody or fragment thereof may comprise a targeting or signal sequence (for example, but not limited to ompA), a detection tag, exemplary tag cassettes include Strep tag, or any variant thereof; see, e.g., U.S. Pat. No. 7,981,632, His tag, Flag tag having the sequence motif DYKDDDDK, Xpress tag, Avi tag, Calmodulin tag, Polyglutamate tag, HA tag, Myc tag, Nus tag, S tag, SBP tag, Softag 1, Softag 3, V5 tag, CREB-binding protein (CBP), glutathione S-transferase (GST), maltose binding protein (MBP), green fluorescent protein (GFP), Thioredoxin tag, or any combination thereof; a purification tag (for example, but not limited to a $His_5$ or $His_6$), or a combination thereof.

In another example, the additional sequence may be a biotin recognition site such as that described by Cronan et al in WO 95/04069 or Voges et al in WO/2004/076670. As is also known to those of skill in the art, linker sequences may be used in conjunction with the additional sequences or tags.

More specifically, a tag cassette may comprises an extracellular component that can specifically bind to an antibody with high affinity or avidity. Within a single chain fusion protein structure, a tag cassette may be located (a) immediately amino-terminal to a connector region, (b) interposed between and connecting linker modules, (c) immediately carboxy-terminal to a binding domain, (d) interposed between and connecting a binding domain (e.g., scFv) to an effector domain, (e) interposed between and connecting subunits of a binding domain, or (f) at the amino-terminus of a single chain fusion protein. In certain embodiments, one or more junction amino acids may be disposed between and connecting a tag cassette with a hydrophobic portion, or disposed between and connecting a tag cassette with a connector region, or disposed between and connecting a tag cassette with a linker module, or disposed between and connecting a tag cassette with a binding domain.

Transmembrane Domain

In particular aspects, the CAR comprises a transmembrane domain that is fused to the extracellular domain and intracellular domain of the CAR. In one aspect, the transmembrane domain that naturally is associated with one of the domains in the CAR is used. In some instances, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein. Transmembrane regions of particular use in this invention may be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154. Typically, the transmembrane domain in the CAR described herein is the CD28 transmembrane domain.

Alternatively the transmembrane domain may be synthetic, in which case it will comprise predominantly hydrophobic residues such as leucine and valine. Typically a triplet of phenylalanine, tryptophan and valine will be found at each end of a synthetic transmembrane domain. Optionally, a short oligo- or polypeptide linker, typically between 2 and 10 amino acids in length may form the linkage between the transmembrane domain and the cytoplasmic signaling domain of the CAR. A glycine-serine doublet provides a particularly suitable linker.

Spacer Domain

Between the extracellular domain and the transmembrane domain of the CAR, or between the cytoplasmic domain and the transmembrane domain of the CAR, there may be incorporated a spacer domain, also referred to as a hinge domain. As used herein, the term "spacer domain" generally means any oligo- or polypeptide that functions to link the transmembrane domain to, either the extracellular domain or, the cytoplasmic domain in the polypeptide chain and elevate the CEACAM6 binding domain from the cell surface. A spacer domain may comprise up to 300 amino acids, typically 10 to 100 amino acids and most typically 25 to 50 amino acids. The spacer may comprise one of the following, for example: a human an IgG1 Fc domain; an IgG1 hinge; an IgG1 hinge-CD8 stalk; a CD8 stalk; IgG1 hinge-CD28 stalk; and a CD28 stalk.

Cytoplasmic Domain

The cytoplasmic domain or otherwise the intracellular signaling domain of the CAR described herein is responsible for activation of at least one of the normal effector functions of the immune cell in which the CAR has been placed in. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Typical examples of intracellular signaling domains for use in the CAR described herein include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs.

Examples of ITAM containing primary cytoplasmic signaling sequences that are of particular use in the invention include those derived from TCR zeta, FcR gamma, FcR beta, CD3 gamma, CD3 delta, CD3 epsilon, CD5, CD22, CD79a, CD79b, and CD66d. It is particularly typical that cytoplasmic signaling molecule in the CAR described herein comprises a cytoplasmic signaling sequence derived from CD3 zeta.

In a typical aspect, the cytoplasmic domain of the CAR can be designed to comprise the CD3-zeta signaling domain by itself or combined with any other desired cytoplasmic domain(s) useful in the context of the CAR described herein. For example, the cytoplasmic domain of the CAR can comprise a CD3 zeta chain portion and one or more costimulatory signaling regions. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like.

The cytoplasmic signaling sequences within the cytoplasmic signaling portion of the CAR described herein may be linked to each other in a random or specified order. Optionally, a short oligo- or polypeptide linker, typically between 2 and 10 amino acids in length may form the linkage. A glycine-serine doublet provides a particularly suitable linker.

In one aspect, the cytoplasmic domain is designed to comprise the signaling domain of CD3-zeta and the signaling domain of CD28. In another aspect, the cytoplasmic domain is designed to comprise the signaling domain of CD3-zeta and the signaling domain of 4-1BB. In yet another aspect, the cytoplasmic domain is designed to comprise the signaling domain of CD3-zeta and the signaling domain of CD28 and 4-1BB.

In one aspect, the cytoplasmic domain in the CAR described herein is designed to comprise the signaling domain of CD28 and/or 4-1BB and the signaling domain of CD3-zeta.

Vectors

Described herein are vectors in which a DNA of the present invention is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

In brief summary, the expression of natural or synthetic nucleic acids encoding CARs is typically achieved by operably linking a nucleic acid encoding the CAR polypeptide or portions thereof to a promoter, and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

The expression constructs of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another aspect, the invention provides a gene therapy vector.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193 the disclosures of which are hereby incorporated by reference in their entirety).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some aspects, adenovirus vectors are used. A number of adenovirus vectors are known in the art. In one aspect, lentivirus vectors are used.

Additional promoter elements, e g, enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1a (EF-1a). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part described herein. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York). A typical method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about –20.degree. C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope described herein.

Transposon/Transposase System

Typical methods for introducing DNA into a cell include DNA condensing reagents such as calcium phosphate, polyethylene glycol, and the like, lipid-containing reagents, such as liposomes, multi-lamellar vesicles, and the like, as well as virus-mediated strategies.

However, all of these methods have their limitations. For example, there are size constraints associated with DNA condensing reagents and virus-mediated strategies. Further, the amount of nucleic acid that can be transfected into a cell is limited in virus strategies. Not all methods facilitate insertion of the delivered nucleic acid into cellular nucleic acid and while DNA condensing methods and lipid-containing reagents are relatively easy to prepare, the insertion of nucleic acid into viral vectors can be labor intensive. Moreover, virus-mediated strategies can be cell-type or tissue-type specific and the use of virus-mediated strategies can create immunologic problems when used in vivo.

One suitable tool in order to overcome these problems are transposons. Transposons or transposable elements include a (short) nucleic acid sequence with terminal repeat sequences upstream and downstream thereof. Active transposons encode enzymes that facilitate the excision and insertion of the nucleic acid into target DNA sequences.

At present, two classes of transposons are known, i.e. class I and class II transposons.

Class I transposons, also called retrotransposons or retroposons, include retroviral-like retrotransposons and non-retroviral-like retrotransposons. They work by copying themselves and pasting copies back into the genome in multiple places. Initially, retrotransposons copy themselves to RNA (transcription) but, instead of being translated, the RNA is copied into DNA by a reverse transcriptase (often coded by the transposon itself) and inserted back into the genome. Typical representatives of class I transposons include e.g. Copia (*Drosophila*), Ty1 (yeast), THE-1 (human), Bs1 (maize), the F-element, L1 (human) or Cin4 (maize).

As a first step Class II transposons have to be transfected to the cells using standard methods like virus infection etc. Following that Class 11 transposons, also called "DNA-only transposons", move by a cut and paste mechanism, rather than by copy and paste, and use the transposase enzyme in this mechanism. Different types of transposases may work in different ways. Some can bind to any part of the DNA molecule, and the target site can be located at any position, while others bind to specific sequences. The transposase then cuts the target site to produce sticky ends, releases the transposon and ligates it into the target site. Typical class I1 representatives include the P element (*Drosophila*), Ac-Ds (maize), TN3 and IS1 (*E. coli*), Tam3 (snapdragon) etc.

Particularly, with class II transposons, the element-encoded transposase catalyzes the excision of the transposon from its original location and promotes its insertion elsewhere in the genome (Plasterk, 1996 Curr. Top. Microbiol. Immunol. 204, 125-143). Autonomous members of a transposon family can express an active transposase, the trans-acting factor for transposition, and thus are capable of transposing on their own. Non-autonomous elements have mutated transposase genes but may retain cis-acting DNA sequences. These cis-acting DNA sequences are also referred to as inverted terminal repeats (IR). Some inverted repeat sequences may include one or more direct repeat sequences. These sequences usually are embedded in the terminal inverted repeats (IRs) of the elements, which are required for mobilization in the presence of a complementary transposase from another element. Not a single autonomous element has been isolated from vertebrates so far with the exception of To12 (see below); all transposon-like sequences are defective, apparently as a result of a process called "vertical inactivation" (Lohe et al., 1995 Mol. Biol. Evol. 12, 62-72). According to one phylogenetic model (Hartl et al., 1997 Trends Genet. 13, 197-201), the ratio of non-autonomous to autonomous elements in eukaryotic genomes increases as a result of the trans-complementary nature of transposition. This process leads to a state where the ultimate disappearance of active, transposase-producing copies in a genome is inevitable. Consequently, DNA-transposons can be viewed as transitory components of genomes which, in order to avoid extinction, must find ways to establish themselves in a new host. Indeed, horizontal gene transmission between species is thought to be one of the important processes in the evolution of transposons (Lohe et al., 1995 supra and Kidwell, 1992. Curr. Opin. Genet Dev. 2, 868-873).

The natural process of horizontal gene transfer can be mimicked under laboratory conditions. In plants, transposons of the Ac/Ds and Spm families have been routinely transfected into heterologous species (Osborne and Baker, 1995 Curr. Opin. Cell Biol. 7, 406-413). In animals, however, a major obstacle to the transfer of an active transposon system from one species to another has been that of species-specificity of transposition due to the requirement for factors produced by the natural host.

Transposon systems as discussed above may occur in vertebrate and invertebrate systems. In vertebrates, the discovery of DNA-transposons, mobile elements that move via a DNA intermediate, is relatively recent (Radice, A. D., et al., 1994. Mol. Gen. Genet. 244, 606-612). Since then, inactive, highly mutated members of the Td/mariner as well as the hAT (hobo/Ac/Tam) superfamilies of eukaryotic transposons have been isolated from different fish species, Xenopus and human genomes (Oosumi et al., 1995. Nature 378, 873; Ivies et al. 1995. Mol. Gen. Genet. 247, 312-322; Koga et al., 1996. Nature 383, 30; Lam et al., 1996. J. Mol. Biol. 257, 359-366 and Lam, W. L., et al. Proc. Natl. Acad Sci. USA 93, 10870-10875).

Both invertebrate and vertebrate transposons hold potential for transgenesis and insertional mutagenesis in model organisms. Particularly, the availability of alternative transposon systems in the same species opens up new possibilities for genetic analyses. For example, piggyβac transposons can be mobilized in Drosophila in the presence of stably inserted P elements (Hacker et al., (2003), Proc Natl Acad Sci USA 100, 7720-5.). Because P element- and piggyBac-based systems show different insertion site preferences (Spradling et al. (1995), Proc Natl Acad Sci USA 92, 10824-30, Hacker et al., (2003), Proc Natl Acad Sci USA 100, 7720-5), the number of fly genes that can be insertionally inactivated by transposons can greatly be increased. P element vectors have also been used to insert components of the mariner transposon into the D. melanogaster genome by stable germline transformation. In these transgenic flies, mariner transposition can be studied without accidental mobilization of P elements (Lohe and Hartl, (2002), Genetics 160, 519-26).

In vertebrates, three active transposons are currently known and used: the To12 element in medaka, and the reconstructed transposons Sleeping Beauty (SB) and Frog Prince (FP). A further interesting transposon system in vertebrates is the PiggyBac transposon system (Ding et al., Cell, 2005).

The To12 element is an active member of the hAT transposon family in medaka. It was discovered by a recessive mutation causing an albino phenotype of the Japanese medaka (Oryzias latipes), a small freshwater fish of East Asia. It was found that the mutation is due to a 4.7-kb long TE insertion into the fifth exon of the tyrosinase gene. The DNA sequence of the element, named To/2, is similar to transposons of the hAT family, including hobo of Drosophila, Acoi maize and Tam3 of snapdragon.

Sleeping Beauty (SB) is a Tc1/mariner-like element from fish and exhibits high transpositional activity in a variety of vertebrate cultured cell lines, embryonic stem cells and in both somatic and germ line cells of the mouse in vivo.

Also Frog Prince (FP) is a Tc1/mariner-like element that was recently reactivated from genomic transposon copies of the Northern Leopard Frog (Rana pipiens). An open reading frame trapping method was used to identify uninterrupted transposase coding regions, and the majority rule consensus of these sequences revealed an active transposase gene. Thus, in contrast to the "resurrection" procedure of SB, the relatively young state of genomic elements in Rana pipiens made it possible to ground the majority rule consensus on transposon copies derived from a single species. The SB and FP transposons are clearly distinct, sharing only −50% identity in their transposase sequences.

Transposons as the above, particularly To12, SB and FP, as well as piggyback (Ding et al., Cell 2005), do not interact and thus may be used as a genetic tool in the presence of others, which considerably broadens the utility of these elements. The preferences of these transposons to insert into expressed genes versus non-coding DNA, and preferences for insertion sites within genes may be substantially different. If so, different patterns of insertion of these transposon systems can be exploited in a complementary fashion. For instance, one could use different transposon systems to transfect several transgenes into cells sequentially, without accidental and unwanted mobilization of already inserted transgenes. In addition, the number of target loci that can be mutagenized by transposon vectors could dramatically increase by combining different transposon systems in genome-wide screens.

In addition to the variation in transpositional activity in hosts, and differences in target site specificity, distinct structural properties of various elements could also be advantageous in certain applications. For example, transposon insertions can be utilized to misexpress genes and to look for gain-of-function phenotypes Roth, P. (1996, A modular misexpression screen in Drosophila detecting tissue-specific phenotypes. Proc Natl Acad Sci USA 93, 12418-22.) used a modified P element transposon that carried an inducible promoter directed out from the element to force expression of host genes near to transposon insertion sites and detected tissue specific phenotypes. A prerequisite of such an experimental setup is that the transposon IRs allow read through transcription/translation across the IRs.

As was already explained above DNA transposons have been developed as gene transfer vectors in invertebrate model organisms and more recently, in vertebrates too. They also rose to be strong rivals of the retroviral systems in human gene therapy. As said before the most useful transposable elements (TEs) for genetic analyses and for therapeutic approaches are the Class II TEs moving in the host genome via a "cut-and-paste" mechanism, due to their easy laboratory handling and controllable nature. Sleeping Beauty (hereinafter abbreviated as "SB") belongs to the TcI/mariner family of the "cut-and-paste" transposons. These mobile DNA elements are simply organized, encoding a transposase protein in their genome flanked by the inverted terminal repeats (ITR). The ITRs carry the transposase binding sites necessary for transposition. Their activities can easily be controlled by separating the transposase source from the transposable DNA harboring the ITRs, thereby creating a non-autonomous TE. In such a two-component system, the transposon can only move by fr3/75 supplementing the transposase protein. Practically any sequence of interest can be positioned between the ITR elements according to experimental needs. The transposition will result in excision of the element from the vector DNA and subsequent single copy integration into a new sequence environment.

In general the transposon mediated chromosomal entry seems to be advantageous over viral approaches because on one hand transposons if compared to viral systems do not favour so much the active genes and 5' regulatory regions and thus are not so prone to mutagenesis, and on the other hand due to their special mechanism of chromosomal entry into of the gene of interest are more physiologically controlled.

SB already proved to be a valuable tool for functional genomics in several vertebrate model organisms (Miskey, C, Izsvak, Z., Kawakami, K. and Ivies, Z. (2005); DNA transposons in vertebrate functional genomics. Cell Mol. Life. Sci. 62: 629-641) and shows promise for human gene therapeutic applications (Ivies, Z. and Izsvak, Z. (2006). Transposons for gene therapy; Curr. Gene Ther. 6: 593-607). However for all of these applications the transpositional activity of the system is a key issue of usability and efficiency. Even though functional and valuable as commonly known and described as of today the transposase activity is likely to be one of the factors that still causes the SB system to reach its limits. Thus, a remarkable improvement of transpositional activity could breach current experimental barriers in both directions.

In aspects, a hyperactive variant of the SB10 transposase is used in the methods described herein. In particular aspects, the hyperactive variant may be that described by WO 2009/003671, incorporated herein by reference in its entirety. For example, a polypeptide selected from variants of SB10 transposase comprising an amino acid sequence differing from the sequence of native SB10 transposase according to SEQ ID No. 8 by 1 to 20 amino acids including at least one of the following mutations or groups of mutations selected from K14R, K13D, K13A, K30R, K33A, T83A, I100L, R115H, R143L, R147E, A205K/H207V/K208R/D210E; H207V/K208R/D210E; R214D/K215A/E216V/N217Q; M243H; M243Q; E267D; T314N; and G317E.

SEQ ID NO: 8 is as follows:

MGKSKEISQDLRKKIVDLHKSGSSLGAISKRLKVPRSSVQTIVRKYKHHG

TTQPSYRSGRRRVLSPRDERTLVRKVQINPRTTAKDLVKMLEETGTKVSI

STVKRVLYRHNLKGRSARKKPLLQNRHKKARLRFATAHGDKDRTFWRNVL

WSDETKIELFGHNDHRYVWRKKGEACKPKNTIPTVKHGGGSIMLWGCFAA

GGTGALHKIDGIMRKENYVDILKQHLKTSVRKLKLGRKWVFQMDNDPKHT

SKVVAKWLKDNKVKVLEWPSQSPDLNPIENLWAELKKRVRARRPTNLTQL

HQLCQEEWAKIFIPTYCGKLVEGYPKRLTQVKQFKGNATKY

"Mutation" or "mutations" is defined herein as the exchange of 1 or more amino acids of a known amino acid sequence by 1 or more other amino acids, respectively, and might—if specifically indicated—also a "group of mutations" or "groups of mutations". A "group of mutations" or "groups of mutations" are defined herein as the exchange of groups, e.g. 3 or 4, of amino acids from the original sequence by 3 or 4 other amino acids at the indicated positions, respectively. As a definition the following code is used to identify the above mutations. "XNo. Z" means that the amino acid "X" of the original amino acid sequence at position "No." is exchanged for amino acid "Z", whereas "XNo.Y/X'No.'Z'/X"No. "Z"" is intended to mean that in this mutation amino acids "X" at position "No.", "X'" in position "No.'" and "X"" in position "No."" are simultaneously exchanged for amino acid "Z", "Z'" and "Z"" respectively. If a "combination of mutations" is defined "//" is used to separate and indicate "simultaneous mutations" in this combination but otherwise is identical to a single slash "/".

In another typical aspect, the variants differ by at least 2, or by at least 1 to 8, typically by 2 to 7 of the above-listed mutations or groups of mutations, even more typically by at least 4 to 7 of the above-listed mutations or groups of mutations.

In another the variants of SB10 transposase are selected from variants comprising the following combination of mutations:

Variant 1: K14R//R214D/K215A/E216V/N217Q;
Variant 2: K33A/R115H//R214D/K215A/E216V/N217Q//M243H;
Variant 3: K14R/K30R//A205K/H207V/K208R/D210E//R214D/K215A/E216V/N217Q//M243H;
Variant 4: K13D/K33A/T83A//H207V/K208R/D210E//M243Q;
Variant 5: K13A/K33A//R214D/K215A/E216V/N217Q;
Variant 6: K33A/T83A//R214D/K215A/E216V/N217Q//G317E;
Variant 7: K14R/T83A/M243Q;
Variant 8: K14R/T83A/I100L/M243Q;
Variant 9: K14R/T83A/R143L/M243Q;
Variant 10: K14R/T83A/R147E/M243Q;
Variant 11: K14R/T83A/M243Q/E267D;
Variant 12: K14R/T83A/M243Q/T314N;
Variant 13: K14R/K30R/I100I7/A205K/H207V/K208R/D210E//R214D/K215A/E216V/N217Q//M243H;
Variant 14: K14R/K30R/R143I7/A205K/H207V/K208R/D210E//R214D/K215A/E216V/N217Q//M243H;
Variant 15: K14R/K30R/R147E//A205K/H207V/K208R/D210E//R214D/K215A/E216V/N217Q//M243H;
Variant 16: K14R/K30R//A205K/H207V/K208R/D210E//R214D/K215A/E216V/N217Q//M243H/E267D;
Variant 17: K14R/K30R//A205K/H207V/K208R/D210E//R214D/K215A/E216V/N217Q//M243H/T314N;
Variant 18: K14R/K30R//A205K/H207V/K208R/D210E//R214D/K215A/E216V/N217Q//M243H/G317E;

Variant 19: K14R/K33A/R115H//R214D/K215A/E216V/N217Q//M243H;
Variant 20: K14R/K30R/R147E//A205K/H207V/K208R/D210E//R214D/K215A/E216V/N217Q//M243H/T314N;
Variant 21: K14R/K30R/R143L//A205K/H207V/K208R/D210E//R214D/K215A/E216V/N217Q//M243H/E267D;
Variant 22: K14R/K30R/R143L//A205K/H207V/K208R/D210E//R214D/K215A/E216V/N217Q//M243H/T314N;
Variant 23: K14R/K30R/R143L//A205K/H207V/K208R/D210E//R214D/K215A/E216V/N217Q//M243H/G317E;
Variant 24: K14R/K33A/R115H/R143L//R214D/K215A/E216V/N217Q//M243H;
Variant 25: K14R/K33A/R115H/R147E//R214D/K215A/E216V/N217Q//M243H;
Variant 26: K14R/K33A/R115H//R214D/K215A/E216V/N217Q//M243H/E267D;
Variant 27: K14R/K33A/R115H//R214D/K215A/E216V/N217Q//M243H/T314N;
Variant 28: K14R/K33A/R115H//R214D/K215A/E216V/N217Q//M243H/G317E;
Variant 29: K14R/T83A/M243Q/G317E;
Variant 30: K13A/K33A/T83A//R214D/K215A/E216V/N217Q In a typical aspect, the transposase is the SB100× transposase, which is noted as Variant 27 in the list above.

Immune Cells

Prior to expansion and genetic modification of the immune cells described herein, a source of the immune cells is obtained from a subject. It will be understood that any source of immune cells may be used, and they may be autologous, allogeneic, syngeneic, or xenogeneic. In typical aspects, the immune cells are autologous or allogeneic.

For example, PBMCs can be obtained by any known method and then stimulated to become CIK cells, as described in, for example, WO 2016/071513, which is incorporated by reference in its entirety. The CIK cells can then be made into CIK CAR cells. Alternatively, T cells can be obtained by any known method and subsequently used to produce CAR-T cells.

Whether prior to or after genetic modification of the immune cells to express a CAR as described herein, the immune cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; U.S. Patent Application Publication No. 20060121005; and WO 2016/071513, incorporated herein by reference in their entirety.

Therapeutic Application

The CAR described herein and immune cells expressing the CAR can block the CEACAM6 antigen and decrease its invasiveness. Binding also activates the CAR-T cell or CIK CAR cell and stimulate immune-cell killing of the cancer cells. An advantage of these antibodies over drugs used for chemotherapy is that they are more specific for tumors that over-express CEACAM6 antigen. Therefore, this might result in reduced general cell toxicity and cancer cell chemoresistance. Additionally, the CAR described herein has tissue penetration ability due to their small size.

The present invention encompasses a cell (e.g., T cell) transduced with a lentiviral vector (LV) or transfected with a transposon. For example, the LV or transposon encodes a CAR that combines an antigen recognition domain of a specific antibody with an intracellular domain of CD3-zeta, CD28, 4-1BB, or any combinations thereof. Therefore the transduced T cell elicits a CAR-mediated T-cell response, thus may aid in reducing tumor growth and inducing cell killing.

The invention provides the use of a CAR to redirect the specificity of a primary T cell to a tumor antigen. Thus, the present invention also provides a method for stimulating a T cell-mediated immune response to a target cell population or tissue in a mammal comprising the step of administering to the mammal a T cell that expresses a CAR, wherein the CAR comprises a binding moiety that specifically interacts with a predetermined target, a zeta chain portion comprising for example the intracellular domain of human CD3zeta, and a co-stimulatory signaling region.

In one aspect, the present invention includes a type of cellular therapy where T cells or CIK cells are genetically modified to express a CAR and the CAR-T or CIK-CAR cell is infused to a recipient in need thereof. The infused cell is able to kill tumor cells in the recipient. Unlike antibody therapies, CAR-T and CIK-CAR cells are able to replicate in vivo resulting in long-term persistence that can lead to sustained tumor control.

In one aspect, the CAR-T or CIK-CAR cells described herein can undergo robust in vivo cell expansion and can persist for an extended amount of time. In another aspect, the CAR-T cells described herein evolve into specific memory T cells that can be reactivated to inhibit any additional tumor formation or growth. Without wishing to be bound by any particular theory, CAR-T cells may differentiate in vivo into a central memory-like state upon encounter and subsequent elimination of target cells expressing the surrogate antigen.

Further, the anti-tumor immunity response elicited by the CAR-modified T or CIK cells may be an active or a passive immune response. In addition, the CAR mediated immune response may be part of an adoptive immunotherapy approach in which CAR-modified T cells induce an immune response specific to the antigen binding moiety in the CAR. For example, CEACAM6-specific CAR-T or CIK cells elicit an immune response specific against cells expressing CEACAM6.

In one aspect, the antigen binding moiety portion of the CAR described herein is designed to treat a particular cancer expressing a particular antigen. For example, the CAR described herein is typically specific for CEACAM6 and can be used to treat cancers and disorders associated with CEACAM6, such as pancreatic cancer, ovarian cancer, bladder cancer, breast cancer, lung cancer, hepatocellular cancer, and colon cancer The CAR-modified T cells described herein may also serve as a type of vaccine for ex vivo immunization and/or in vivo therapy in a mammal. Typically, the mammal is a human.

With respect to ex vivo immunization, at least one of the following occurs in vitro prior to administering the cell into a mammal: i) expansion of the cells, ii) introducing a nucleic acid encoding a CAR to the cells, and/or iii) cryopreservation of the cells.

Ex vivo procedures are well known in the art and are discussed more fully below. Briefly, cells are isolated from a mammal (typically a human) and genetically modified (i.e., transduced or transfected in vitro) with a vector expressing a CAR disclosed herein. The CAR-modified cell can be administered to a mammalian recipient to provide a therapeutic benefit. The mammalian recipient may be a human and the CAR-modified cell can be autologous with respect to the recipient. Alternatively, the cells can be allogeneic, syngeneic or xenogeneic with respect to the recipient.

The procedure for ex vivo expansion of hematopoietic stem and progenitor cells is described in U.S. Pat. No. 5,199,942, incorporated herein by reference, can be applied to the cells described herein. Other suitable methods are known in the art, therefore the present invention is not limited to any particular method of ex vivo expansion of the cells. Briefly, ex vivo culture and expansion of T cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

In addition to using a cell-based vaccine in terms of ex vivo immunization, the present invention also provides compositions and methods for in vivo immunization to elicit an immune response directed against an antigen in a patient.

In particular, the CAR-modified T cells described herein are used in the treatment of a CEACAM6 expressing cancer. In certain aspects, the cells described herein are used in the treatment of patients at risk for developing a CEACAM6 expressing cancer. Thus, the present invention provides methods for the treatment or prevention of a CEACAM6 expressing cancer comprising administering to a subject in need thereof, a therapeutically effective amount of the CAR-modified T cells described herein.

The CAR-modified T cells of the present invention may be administered either alone, or as a pharmaceutical composition in combination with diluents and/or with other components such as IL-2 or other cytokines or cell populations. Briefly, pharmaceutical compositions of the present invention may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are typically formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount", "an anti-tumor effective amount", "an tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, typically $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain aspects, it may be desired to administer activated T cells to a subject and then subsequently redraw blood (or have an apheresis performed), activate T cells therefrom according to the present invention, and reinfuse the patient with these activated and expanded T cells. This process can be carried out multiple times every few weeks. In certain aspects, T cells can be activated from blood draws of from 10 cc to 400 cc. In certain aspects, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocol may serve to select out certain populations of T cells.

The administration of the subject compositions may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i.v.) injection, or intraperitoneally. In one aspect, the T cell compositions of the present invention are administered to a patient by intradermal or subcutaneous injection. In another aspect, the T cell compositions of the present invention are typically administered by i.v. injection. The compositions of T cells may be injected directly into a tumor, lymph node, or site of infection.

In certain aspects of the present invention, cells activated and expanded using the methods described herein, or other methods known in the art where T cells are expanded to therapeutic levels, are administered to a patient in conjunction with (e.g., before, simultaneously or following) any number of relevant treatment modalities, including but not limited to chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1991; Henderson et al., Immun 73:316-321, 1991; Bierer et al., Curr. Opin. Immun 5:763-773, 1993). In a further aspect, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another aspect, the cell compositions of the present invention are administered following B-cell ablative therapy such as agents that react with CD20, e.g., Rituxan. For example, in one aspect, subjects may undergo standard treatment with high dose chemotherapy followed by peripheral blood stem cell transplantation. In certain aspects, following the transplant, subjects receive an infusion of the expanded immune cells described herein. In an additional aspect, expanded cells are administered before or following surgery.

The dosage of the above treatments to be administered to a patient will vary with the precise nature of the condition being treated and the recipient of the treatment. The scaling of dosages for human administration can be performed according to art-accepted practices. The dose for CAMPATH, for example, will generally be in the range 1 to about 100 mg for an adult patient, usually administered daily for a period between 1 and 30 days. The typical daily dose is 1 to 10 mg per day although in some instances larger doses of up to 40 mg per day may be used (described in U.S. Pat. No. 6,120,766).

In aspects of the invention the compositions comprising the CAR-T of the invention may be stored refrigerated until use or frozen (then thawed) until required for use. The compositions may be formulated and provided as a "bank" of CAR-T cells for therapeutic treatment of CEACAM6 cancers.

In embodiments of the invention, cells that are to be used for cell therapy are provided in a kit, and in some cases the cells are essentially the sole component of the kit. The kit may comprise reagents and materials to make the desired cell. In specific embodiments, the reagents and materials include primers for amplifying desired sequences, nucleotides, suitable buffers or buffer reagents, salt, and so forth, and in some cases the reagents include vectors and/or DNA that encodes a CAR as described herein and/or regulatory elements therefor.

In particular embodiments, there are one or more apparatuses in the kit suitable for extracting one or more samples from an individual. The apparatus may be a syringe, scalpel, and so forth.

In some cases of the invention, the kit, in addition to cell therapy embodiments, also includes a second cancer therapy, such as chemotherapy, hormone therapy, and/or immunotherapy, for example. The kit(s) may be tailored to a particular cancer for an individual and comprise respective second cancer therapies for the individual.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the typical aspects of the present invention, and are not to be construed as limiting in any way the remainder of the disclosure.

Summary of Findings

CEACAM6 is overexpressed in many types of human cancers such as breast, pancreatic, colorectal, and non-small-cell lung adenocarcinoma, and is an independent predictor of overall survival and disease free survival. Targeting this molecule by antibodies has slowed tumor progression in certain animal models. 2A3 is a camelid single domain antibody isolated from a whole cancer cell immunized llama library. The antibody binds specifically to the CEACAM6 antigen with high affinity (5 nM as measured by SPR) and inhibits the proliferation of CEACAM6-expressing cancer cells in vitro. In this study, Chimeric-Antigen Receptor (CAR) T cells were engineered to target human CEACAM6 antigen by transducing the 2A3 antibody sequence to generate a modified chimeric CD28 signaling domain fused to chimeric CD3-zeta. Transduction efficiency and expression of 2A3 antibody were verified by flow cytometry. Co-incubation of CEACAM6-specific CAR-T (CEACAM6-CAR-T) cells with the CEACAM6-expressing pancreatic cell line BxPC-3 resulted in augmented cytotoxicity and cytokines (IL-2 and IFN-γ) release, suggesting potential anti-cancer activity of the CAR-T cells. Data from real-time cell analysis showed a significant increase in BxPC-3 cell cytotoxicity by CEACAM6-CAR-T cells, as compared to native T cells. However, CEACAM6-CAR-T cells showed much lower cytotoxic activity on negative control cell lines. The efficacy of CEACAM6-CAR-T cells in xenograft model was examined in vivo. BxPC3 cells were inoculated subcutaneously into the hind flank of CIEA NOG mice. Three groups of mice then received intravenous injection of either PBS, native T cells, or CEACAM6-CAR-T cells, respectively, at day 1, 8, and 15. The data demonstrated very high efficacy of CEACAM6-CAR-T cells against the pancreatic cancer xenograft. CEACAM6-CAR-T cells significantly decreased the growth of the BxPC-3 xenograft as compared to that of native T cells (p-value=0.00025) and PBS (p-value=7.91×10$^6$). No toxic effect was observed based on body weight measurement. The results strongly support that CEACAM6-CAR-T cells can be used as an effective immunotherapy agent against CEACAM6-expressing cancers, and that camelid single domain antibodies can be adopted for CAR-T type therapies.

Example 1

The CAR was cloned into the Xbal and EcoRI cloning sites of the lentiviral plasmid Lenti CMV-MCS-EF1a-puro (Alstem, Richmond, Calif.). All plasmid inserts were sequence verified following synthesis and cloning. Each CAR plasmid was transformed into *E. coli* BL21 cells for production and isolation of transfection-ready DNA prior to generating lentiviral stock. The viral titer was detected by the qRT-PCR analysis of genomic lentiviral RNA. The source of human T cells to be transduced were peripheral blood mononuclear cells (PBMC), isolated from whole blood by Ficoll-Paque gradient Real-Time Cell Assay (RTCA) Protocol Day 1:

A. Preparing the (Adherent) Target Cells:

1. Aspirate the old medium from the flask

2. Add 5-10 mL of regular medium (without serum) to the flask to rinse off any serum residue. Then, aspirate the medium.

3. Add 0.5 mL-1 mL of 0.05% Trypsin-EDTA to the flask to detach the cells.

4. Add 4.5 mL-9.5 mL of medium (with FBS) to the flask and pipet the medium up and down to the bottom of the flask to disrupt the cells into single cell solution.

5. Transfer the suspended cell suspension into a 15 mL tube.

6. Take out 10 uL of the cell suspension and count, using a hemacytometer, to determine the cell concentration.

7. Centrifuge the cell suspension at 1000 rpm (or 300× g) for 5 mins at 25° C.

8. After centrifugation, aspirate the supernatant and re-suspend the cell pellet in medium (with FBS) until concentration is $1\times10^5$ cells/mL B. Preparing the RTCA Plate:

1. Add 50 uL of medium only (the same medium used for the cell suspension) to the wells that will be measured.

2. Place the E-Plate (ACEA Biosciences, Inc, Catalog #: JL-10-156010-1A) back on the station.

3. Start the RTCA 2.0 software
 a. Enter Layout information:
  i. At the very least, select all wells and click "Apply". This activates the wells
 b. Enter Schedule:
  i. Step 1=Background measurement. Do not change.
  ii. Step 2=Monitoring of cells
  iii. Step 3=Short term cytotoxicity
  iv. Step 4=Long term cytotoxicity (check the "Auto" box)
You can change the amount of cycles for each step and the interval between each cycle

4. Click "Step 1" and press Start to name the experiment and measure the background from media 5. After "Step 1" is complete, remove the E-Plate from the station.

6. Add 100 uL of cells suspension from Part A to the wells (Do not remove the prior media. There should be a final of 150 uL total in each well)

7. Let the cells settle for 5 minutes in the hood

8. Place the E-Plate back on the station

9. Click "Step 2" and press Start to resume the recordings

Day 2—Treatment:

A. Preparing the CAR-T Effector Cells:

1. Take all the suspended CAR-T cells from the 6-well plate and mix well.

2. Take 10 uL of the cell suspension and determine the cell concentration using a hematocytometer 3. Centrifuge the cell suspension at 1000 rpm (or 300×g) for 5 mins @25° C.

4. Aspirate the supernatant and resuspend the cell pellet in 2 mL of Cytotoxicity Buffer (RPMI 1640 Phenol Free (Invitrogen)+1% P/S (Invitrogen)+5% Human AB Serum (Gemini Bioproducts; 100-318))

5. Repeat step 3

6. Aspirate the supernatant and resuspend the cell pellet in Cytotoxicity media (Phenol red-free RPMI1640 (Invitrogen) plus 5% AB serum (Gemini Bioproducts; 100-318)) to obtain a final concentration at $1\times10^6$ cells/mL B. Preparing the RTCA Plate:

1. After Part A is complete, press fast-forward to step 3.

2. Remove the E-Plate from the station

3. Aspirate the supernatant carefully from each well

4. Add 100 uL of Cytotoxicity media to each well

5. Repeat step 3

6. Add 50 uL of Cytotoxicity media to each well

7. Dispense 100 uL of the CAR-T cell suspension ($1\times10^5$ cells) from Part A to the desired wells per design.

8. Return the E-Plate to the station

9. Click "Step 3" and press Start to resume the recordings

Sequence of CAR: second generation CEACAM-6 scFv-CD28-CD3 (SEQ ID NO: 5):

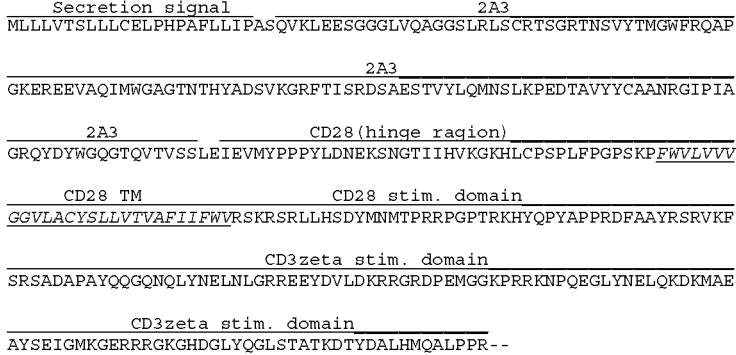

Protocol for Flow Cytometry

Cells are washed and suspended in FACS buffer (Phosphate-buffered saline (PBS) plus 0.1% sodium azide and 0.4% BSA). Cells are then divided them $1\times10^6$ aliquots.

Fc receptors are blocked with normal goat IgG (LifeTechnologies). Add 100 μl of 1:1000 diluted normal goat IgG to each tube and incubate in ice for 10 min.

Add 1.0 ml FACs buffer to each tube, mix well and spin down at 300×g for 5 min.

Add biotin-labeled polyclonal goat anti-mouse-F(ab)2 antibodies (Life Technologies) to detect CD19 scFv; biotin-labeled normal polyclonal goat IgG antibodies (Life Technologies) is added to serve as an isotype control. (1:200 dilution, reaction volume of 100 μl).

Cells are incubated at 4° C. for 25 minutes and washed once with FACS buffer.

Suspend cells in FACs buffer and block with normal mouse IgG (Invitrogen) by adding 100 μl 1:1000 diluted normal mouse IgG to each tube. Incubate in ice for 10 min. Wash cells with FACS buffer and re-suspend in 100 μl FACS buffer.

The cells are then stained with phycoerythrin (PE)-labeled streptavidin (BD Pharmingen, San Diego, Calif.) and allophycocyanin (APC)-labeled CD3 (eBioscience, San Diego, Calif.). Add 1.0 μl PE and APC each to tube 2 and 3.

Flow cytometry acquisition was performed with a BD FacsCalibur (BD Biosciences), and analysis was performed with FlowJo (Treestar, Inc. Ashland, Oreg.).

|  | G1 PBS | | | G2 Mock | | | G3 CAR T | | |
|---|---|---|---|---|---|---|---|---|---|
| DAYS | MEAN | SD | N | MEAN | SD | N | MEAN | SD | N |
| 0 | 0 | 0 | 5 | 0 | 0 | 5 | 0 | 0 | 5 |
| 2 | 31.84 | 19.04 | 5 | 49.00 | 32.07 | 5 | 45.17 | 7.09 | 5 |
| 6 | 73.45 | 30.43 | 5 | 95.01 | 48.69 | 5 | 42.48 | 13.83 | 5 |
| 9 | 93.37 | 27.30 | 5 | 114.74 | 29.56 | 5 | 68.11 | 18.75 | 5 |
| 13 | 107.78 | 26.14 | 5 | 112.59 | 24.73 | 5 | 62.95 | 12.48 | 5 |

2A3, cloned into a mammalian expression vector as a huFc fusion protein (C-terminal Fe) (SEQ ID NO: 9):

(SEQ ID NO: 11)

ggatccgccgccacc*ATGCTTCTCCTGGTGACAAGCCTTCTGCTCTGTGAGTTACCACACCCAGCATTCC*

*TCCTGATCCC*ACAGGTAAAGCTGGAGGAGTCTGGGGGAGGATTGGTGCAGGCTGGGGGCTCTCTGAGACT

CTCTGGACGCACCAACAGTGTCTATACCATGGGCTGGTTCCGCCAGGCTCCAGGGAAG

GAGCGTGAGTTTGTAGCACAAATTATGTGGGGTGCAGGTACTAACACGCACTATGCAGACTCCGTGAAGG

GCCGATTCACCATCTCCAGAGACAGCGCCGAGAGCACGGTGTACCTGCAAATGAACAGCCTGAAACCTGA

GGACACGGCCGTTTATTACTGTGCAGCGAATCGGGGAATACCTATTGCTGGCCGGCAATATGACTACTGG

GGCCAGGGGACCCAGGTCACCGTCTCCTCAggcggcggtggttctagaGAAAACCTGTATTTTCAGGGCACTC

ACACATGCCCACCGTGCCCAGCACCTGAACTCCTGGGGGGACCGTCAGTCTTCCTCTTCCCCCCAAAACCCAAGGAC

ACCCTCATGATCTCCCGGACCCCTGAGGTCACATGCGTGGTGGTGGACGTGAGCCACGAAGACCCTGAGGTCAAGTT

CAACTGGTACGTGGACGGCGTGGAGGTGCATAATGCCAAGACAAAGCCGCGGGAGGAGCAGTACAACAGCACGTACC

GTGTGGTCAGCGTCCTCACCGTCCTGCACCAGGACTGGCTGAATGGCAAGGAGTACAAGTGCAAGGTCTCCAACAAA

GCCCTCCCAGCCCCCATCGAGAAAACCATCTCCAAAGCCAAAGGGCAGCCCCGAGAACCACAGGTGTACACCCTGCC

CCCATCCCGGGATGAGCTGACCAAGAACCAGGTCAGCCTGACCTGCCTGGTCAAAGGCTTCTATCCCAGCGACATCG

CCGTGGAGTGGGAGAGCAATGGGCAGCCGGAGAACAACTACAAGACCACGCCTCCCGTGCTGGACTCCGACGGCTCC

TTCTTCCTCTACAGCAAGCTCACCGTGGACAAGAGCAGGTGGCAGCAGGGGAACGTCTTCTCATGCTCCGTGATGCA

TGAGGCTCTGCACAACCACTACACGCAGAAGAGCCTCTCCCTGTCTCCCGGGAAATGA

MLLLVTSLLLCELPHPAFLLIPQVKLEESGGGLVQAGGSLRLSCRTSGRTNSVYTMGWFRQAPGKEREFV

AQIMWGAGTNTHYADSVKGRFTISRDSAESTVYLQMNSLKPEDTAVYYCAANRGIPIAGRQYDYWGQGTQ

VTVSSGGGGSRENLYFQGTHTCPPCPAPELLGGPSVFLFPPKPKDTLMISRTPEVTCVVVDVSHEDPEVK

FNWYVDGVEVHNAKTKPREEQYNSTYRVVSVLTVLHQDWLNGKEYKCKVSNKALPAPIEKTISKAKGQPR

EPQVYTLPPSRDELTKNQVSLTCLVKGFYPSDIAVEWESNGQPENNYKTTPPVLDSDGSFFLYSKLTVDK

SRWQQGNVFSCSVMHEALHNHYTQKSLSLSPGK

2A3[2nd] generation CAR construct, "pCD510-FMC63-2A3-hu28z": 2A3 with C-terminal CD28 (hinge, transmembrane (TM), stimulatory domain) and CD3zeta (stimulatory domain) fusion (SEQ ID NO: 10):

difficulties in expanding following activation and transduction. Only two of the three additional donors were therefore used for subsequent experiments, and include "Donor 2" and "Donor 3" discussed within this report. Viral stock A there-

```
tctagagccgccaccATGCTTCTCCTGGTGACAAGCCTTCTGCTCTGTGAGTTACCACACCCAGCATTCC

TCCTGATCCCAgctagcCAGGTAAAGCTGGAGGAGTCTGGGGGAGGATTGGTGCAGGCTGGGGGCTCTCT

GAGACTCTCCTGTAGAACCTCTGGACGCACCAACAGTGTCTATACCATGGGCTGGTTCCGCCAGGCTCCA

GGGAAGGAGCGTGAGTTTCTAGCACAAATTATGTGGGGTGCAGGTACTAACACGCACTATGCAGACTCCG

TGAAGGGCCGATTCACCATCTCCAGAGACAGCGCCGAGAGCACGGTGTACCTGCAAATGAACAGCCTGAA

ACCTGAGACACGGCCGTTTATTACTGTGCAGCGAATCGGGGAATACCTATTGCTGGCCGGCAATATGAC

TACTGGGGCCAGGGGACCCACCTCACCGTCTTCCTCActcgagATTGAAGTTATGTATCCTCCTCCTTACC

TAGACAATGAGAAGAGCAATGGAACCATTATCCATGTGAAAGGGAAACACCTTTGTCCAAGTCCCCTATT

TCCCGGACCTTCTAAGCCCTTTTGGGTGCTGGTGGTGGTTGGGGAGTCCTGGCTTGCTATAGCTTGCTA

GTAACAGTGGCCTTTATTATTTTCTGGGTGAGGAGTAAGAGGAGCAGGCTCCTGCACAGTGACTACATGA

ACATGACTCCCCGCCGCCCCGGGCCCACCCGCAAGCATTACCAGCCCTATGCCCCACCACGCGACTTCGC

AGCCTATCGCTCCAGAGTGAAGTTCAGCAGGAGCGCAGACGCCCCCGCGTACCAGCAGGGCCAGAACCAG

CTCTATAACGAGCTCAATCTAGGACGAAGAGAGGAGTACGATGTTTTGGACAAGAGACGTGGCCGGGACC

CRGAGATGGGGGAAAGCCGAGAAGGAAGAACCCTCAGGAAGGCCTGTACAATGAACTGCAGAAAGATAA

GATGGCGGAGGCCTACAGTGAGATTGGGATGAAAGGCGAGCGCCGGAGGGGCAAGGGGCACGATGGCCTT

TACCAGGGTCTCAGTACAGCCACCAAGGACACCTACGACGCCCTTCACATGCAGGCCCTGCCCCCTCGCT

AATAGGAATTC
```

Example 2

Chimeric-Antigen Receptor T-cells (CAR-T cells) were generated using an Anti-camelid specific antibody against human CEACAM6. These CAR-T were initially shown to demonstrate potent cytotoxic activity against cells displaying CEACAM6 target antigen, and additional studies were initiated to observe the variability of the cytotoxic effect against multiple PBMC-donors.

Data suggest that the anti-CEACAM6 CAR-T is effective across a range of human donors of T cells.

Anti-CEACAM6 CAR Lentivirus Production:

| Viral Stock | CAR Construct | Viral Titer (IFU/mL) |
|---|---|---|
| A | Anti-CEACAM6 | 2.86 ± 0.19 × 10$^8$ (for donor 1) |
| B | Anti-CEACAM6 | 3.08 ± 0.13 × 10$^8$ (for donor 2 and 3) |

Excess viral stocks made to accommodate the transduction of multiple independent T cell populations, and virus not immediately used were stored at −80° C. Transduction occurred with a multiplicity of infection (MOI) of 5:1 (Virus to cell ratio).

Donor 1 PBMC were used in generating initial anti-CEACAM6 data. Three additional donors were examined, but PBMC from one of the additional donors had repeated fore was used to transduce donor 1 PBMC, and viral stock B used for the transduction of PBMC from donor 2 and donor 3 respectively.

Real-Time Cell Assay (RTCA), CAR-T Cell Cytotoxicity

Figure 2:
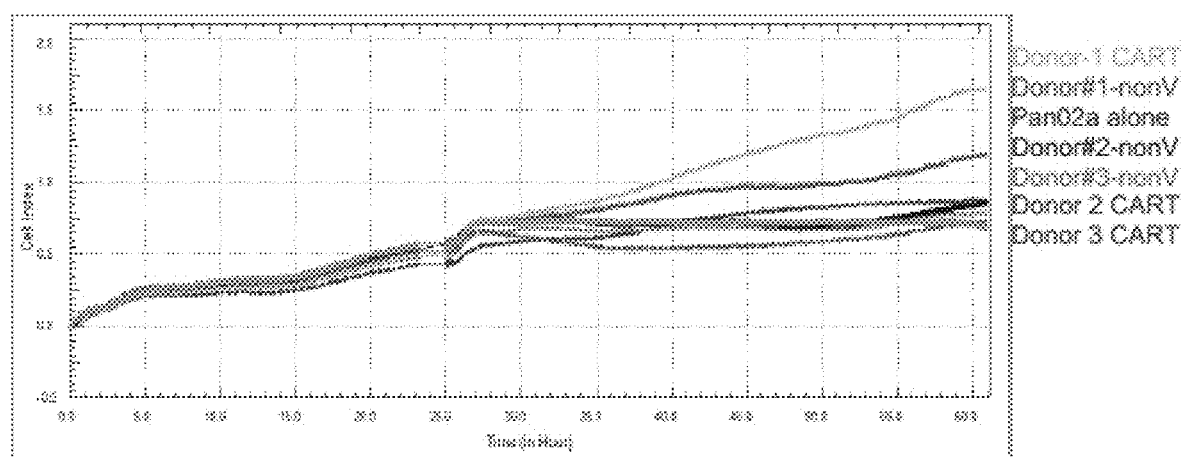
FIG. 2 is a graph showing that CEACAM6-negative cells are not killed in the present of CAR-T cells. RTCA using Pan02a (negative for CEACAM6) target cells. Effector to target cell ratio was 10:1. Following introduction of effector cells, RTCA data collection proceeded for an additional 36 hours.

Cells used for the cytotoxicity assays in FIGS. 1 and 2 were expanded to 14-15 days before use (Cells from Donor 1 were expanded to day 14 while cells from Donors 2 and 3 were expanded to day 15). BXPC3 was used as the positive target cell line while Pan02a cells were used as the negative target cell line. Target cells were plated at 1×10$^4$ cells per well (of a 96 well plate), and incubated for 24 hr. Anti-CEACAM6 CAR-T cells were used as effector cells, along with non-transduced CAR-T cells as a negative control. Anti-CEACAM6 CAR-T cells were introduced from frozen stocks following transduction with Anti-CEACAM6 CAR and expansion. CAR-T cells were added to appropriate wells, containing target cells, at a ratio of 10:1.

BXPC3 data suggest a specific, and virtually identical cytotoxic profile as displayed by RTCA Cell Index values, and confirm initial anti-CEACAM6 CAR-T cytotoxicity data. Pan02a cells, a mouse pancreatic line that is negative for human CEACAM 6 expression, are not affected by CEACAM6 CAR-T cells.

Cytokine Secretion Assay

Figure 3A:
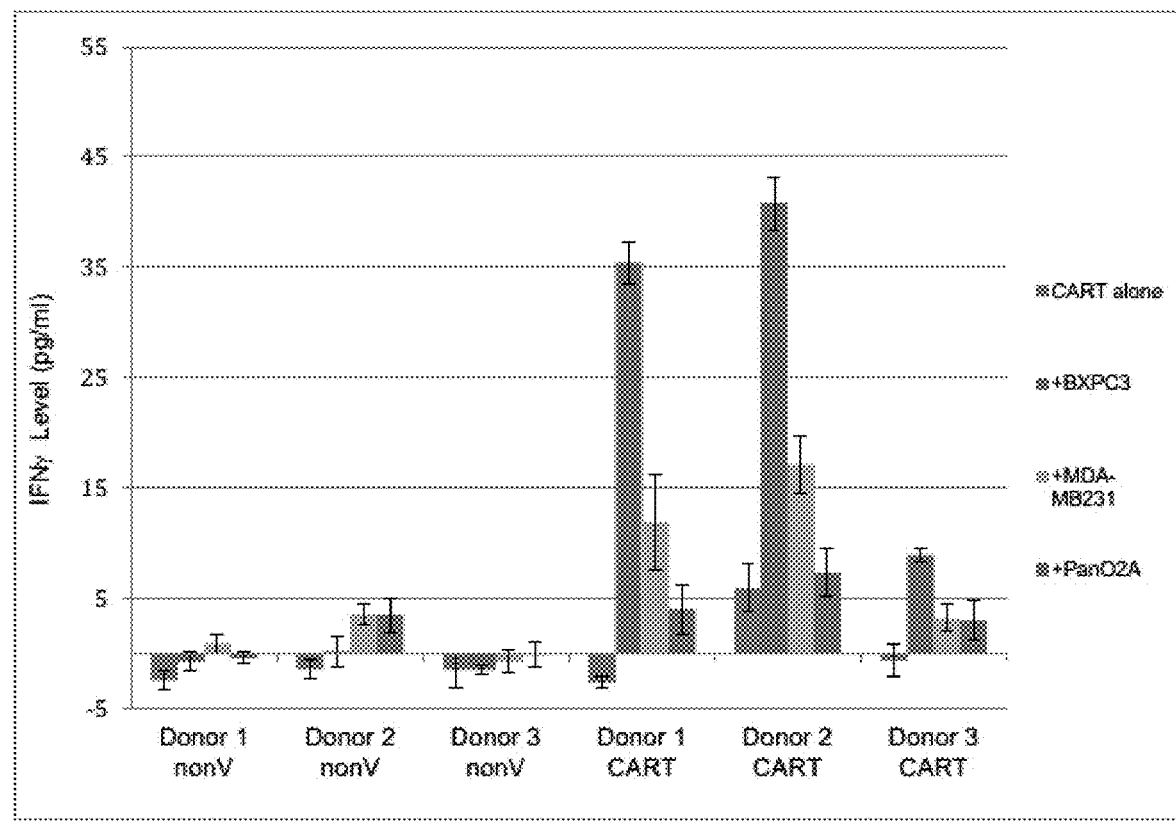
FIG. 3A is a graph showing interferon gamma secretion levels are increased in a significant and CAR-T specific manner. 3B shows a standard-curve generated for the IFN-gamma secretion assay.
Figure 3B:
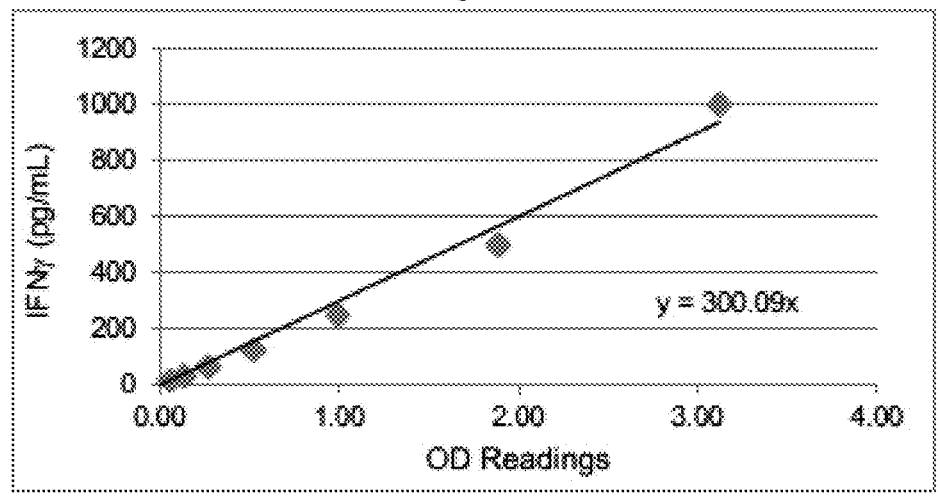
Figure 4A:
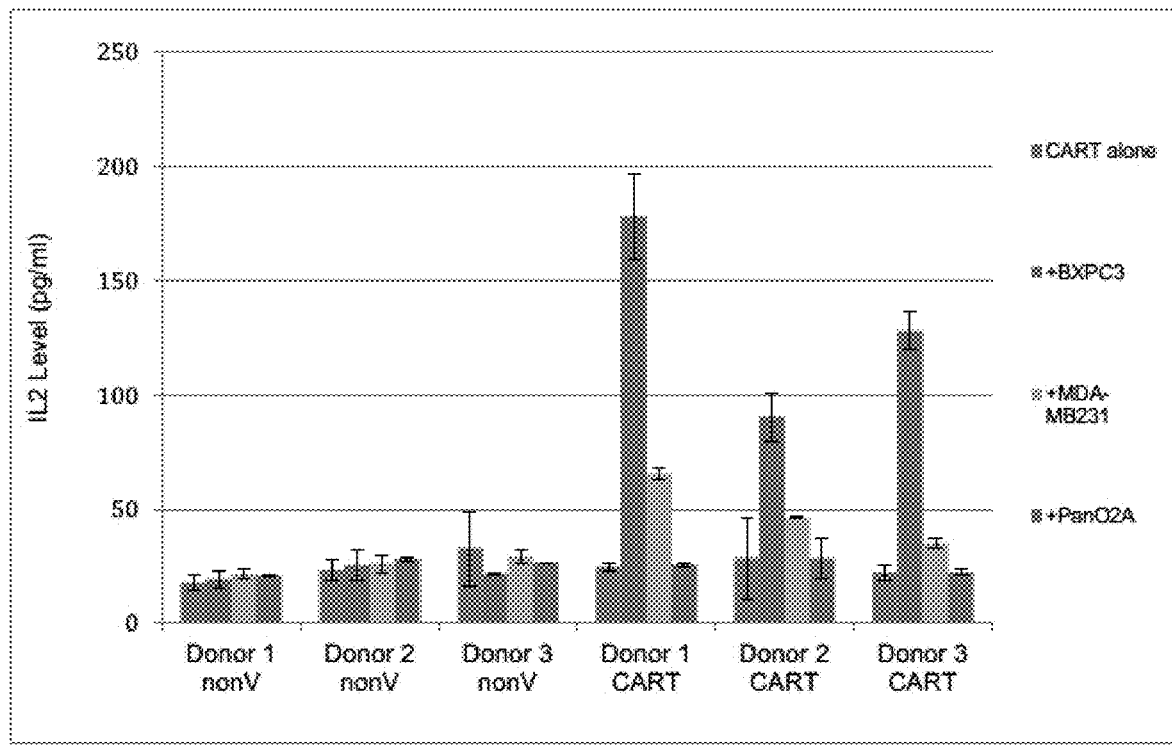
FIG. 4A is a graph showing IL-2 secretion levels are increased in a significant CAR-T specific manner. 4B is a graph showing a standard-curve generated for the IL-2 secretion assay.
Figure 4B:
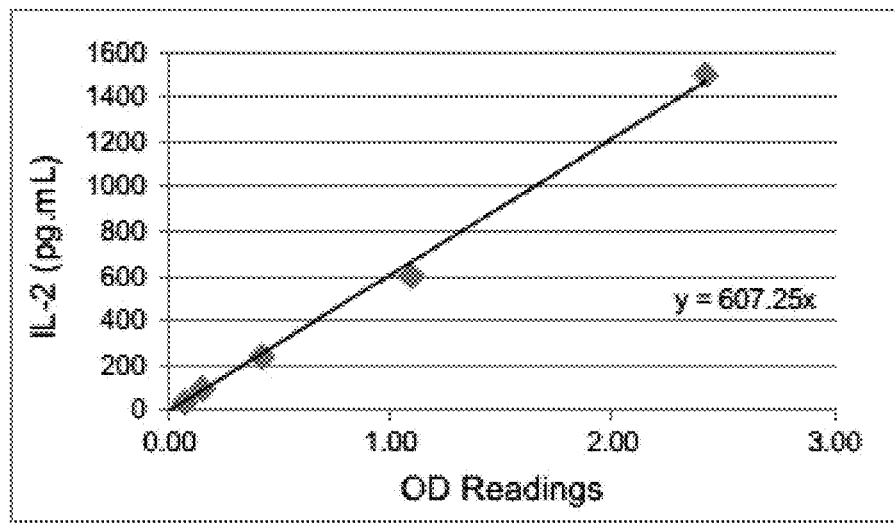

Cells used for the cytokine secretion assay were expanded to 15 days. With 1×10$^4$ target cells plated per well (of a 96 well plate) effector cells were added at an effector to target cell ratio of 1:1, and incubated together for approximately 18 hr before removal of supernatant for assay for IFN-gamma, and IL-2 concentrations, FIGS. 3A and 4A respectively. Standard curves are shown in FIGS. 3B and 4B.

Example 3

The efficacy of CEACAM-6-CAR-T cells in pancreatic cancer cell, BxPC3 xenografts was tested in vivo. In a previous experiment high cytotoxicity of CEACAM-6-CAR-T cells against BxPC3 cells in vitro has been demonstrated. In this example CIEA-NOG mice (Taconic) were injected subcutaneously with BxPC3 cells into the hind flank ($2\times10^6$ cells/mice). The three groups of mice: PBS, Mock (T cells) and CEACAM-6 CAR-T cells (5 mice per group) received at day 1, 8 and 15 intravenous (i.v) injection of either PBS or $1\times10^7$ T cells or CAR-T cells.

The data demonstrate very high efficacy of CEACAM-6 CAR-T cells using xenograft mice model. CEACAM-6 CAR-T cells significantly decreased pancreatic cell BcPC3 xenograft tumor growth versus Mock T cells (p-value=0.00025) and versus PBS group (p-value=7.90984E-06). The data suggest high therapeutic potential of CEACAM-6 CAR-T cells against pancreatic cancer.

Verification of Transduction Efficiency Following T-Cell Activation, Transduction, and Expansion of CEACAM-6 CAR-T Cells In Vitro.

The source of human T cells to be transduced were peripheral blood mononuclear cells (PBMC), isolated from whole blood by Ficoll-Paque gradient (see Appendix).

Cells were suspended at $1\times10^6$ cells/mL with IL-2 (300 IU/mL), activated with CD28/CD3 microbeads, and transduced with respective stocks of recombinant lentivirus 24 hr following activation. Cells were then passaged at 2-3 day intervals with huIL-2 concentrations maintained at 300 IU/m. The fresh CEACAM-6 CAR-T cells were prepared each week with new lentivirus transduction. Fresh lentivirus was prepared from the same DNA (titer was determined with PCR and equal to $3.40+/-0.31*10^8$ IFU/mL) and used for transduction each week during 3 weeks to generate CAR-T cells for 3 intravenous (i.v) injections into mice at concentration $1\times10^7$ cells per mice at days 1, 8 and 15 after BxPC3 pancreatic cancer cell injection ($2\times10^6$ cells/mice subcutaneously). The control T cells were also cultivated for Mock control injection into mice at the same concentration at the same days of injection.

Figure 5:
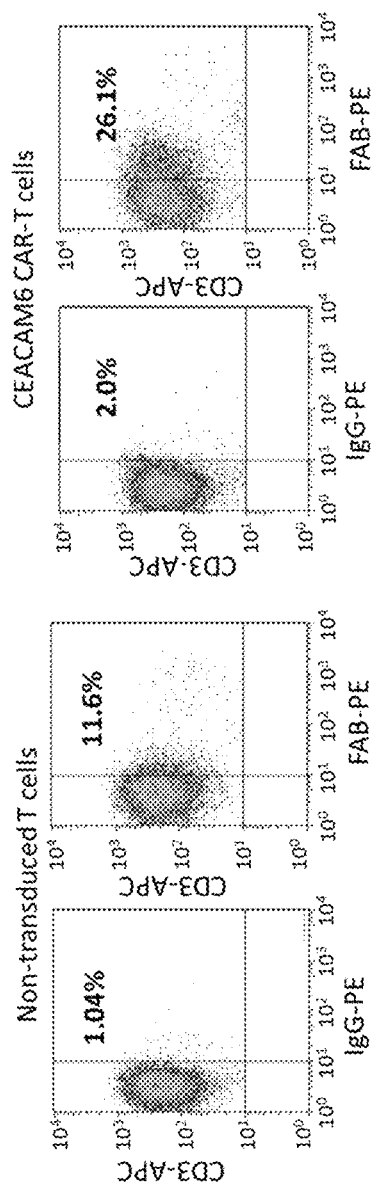
FIG. 5 shows anti-Fab antibody binding to CAR-T cells indicating a transduction efficiency of >26%.

Expression of CEACAM-6 in CAR-T cells was detected by flow cytometry, using an anti-mouse Fab antibody to detect the CEACAM-6 scFv. The non-transduced T cells were used as a negative control. Anti-CD3 antibodies were also used to examine the overall distribution of CD3-positive cells within the population. The flow cytometry data are shown in FIG. 5 and demonstrate transduction efficiency of >26%.

High CEACAM-6 CAR-T Cytotoxicity Against BxPC3 Cells

RTCA Assay

Figure 6:
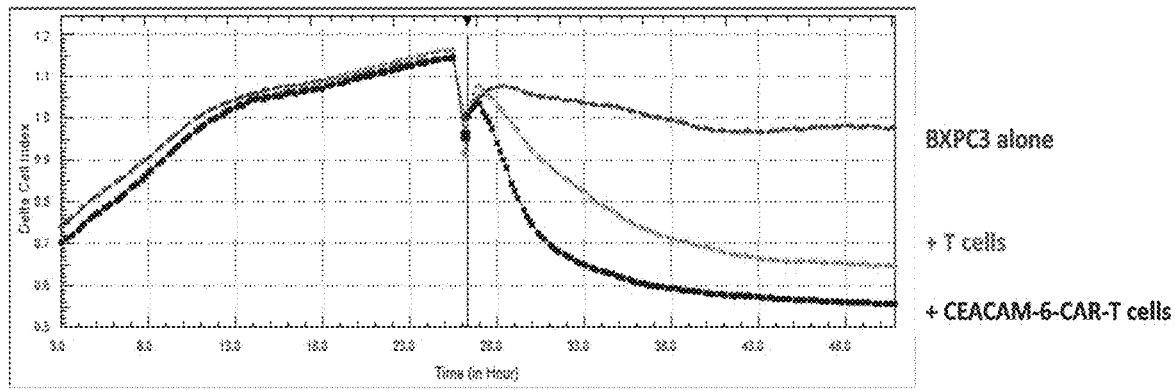
FIG. 6 shows the RTCA Indicating an Enhanced Cytotoxic Effect of CEACAM-6 CAR-T cells versus target BxPC-3 cells. Ratio of Effector:Target cells=10:1. A. CAR-T cells for injection #1 at Day 1; B. CAR-T cells used for injection #2, Day 8. C. CAR-T cells used for injection #3, Day 15.
Figure 6:
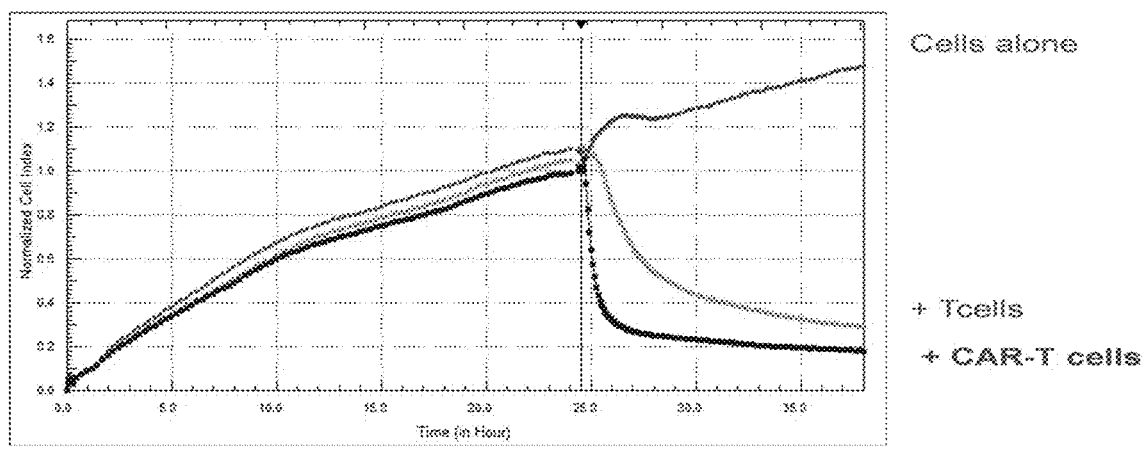
Figure 6:
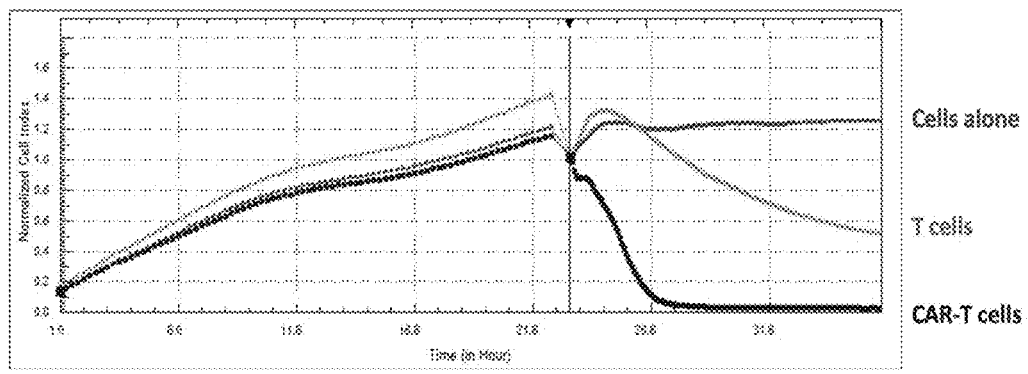

Cytotoxicity of CEACAM-6-CAR-T cells against BxPC3 target cells was measured by Real-time cell analysis (RTCA) for each batch of CAR-T cells (#1, 2 and 3) (FIG. 6 A,B,C).

The RTCA to date provides reliable data when using adherent cell lines. Our target cells were BxPC3 cells and effector cells were CAR-T cells at a ratio of 1:10.

RTCA experimental samples include the following:
(i) Target BxPC3
(ii) Normal, non-transduced CAR-T cells (negative effector cell control)
(iii) CEACAM-6-CAR-T cells, human T-cells transduced with CEACAM-6 CAR lentivirus (Positive Effector cells).

In brief, cells were plated at $1\times10^4$ cells per well 24 hr prior to the introduction of CEACAM-6 CAR-T effector cells. Impedance values across the E-plate were recorded from this point on. Once cells were confluent, wells were washed and appropriate number of CAR-T cells were added, depending on the effector:target cell ratio desired.

Data (FIG. 6) clearly show a significant increase in BxPC3 cell cytotoxicity by CEACAM-6-CAR-T, as compared to the negative control T cells. T cells have some cytotoxic activity that was seen previously in some donors. CEACAM-6 CAR-T Cells Significantly Decreased BxPC3 Xenograft Tumor Growth In Vivo.

CIEA NOG (NOD.Cg-Prkdcscid Il2rgtm1Sug/JicTac) female mice 5 weeks of age were obtained from Taconic Bioscience (Hudson, N.Y.). Pancreatic BxPC3 cancer cells, ($2\times10^6$ cells/mice) were injected subcutaneously into the hind flank of NOG mice subcutaneously. The next day after BxPC3 cell injection PBS, T cells or CEACAM-6-CAR-T cells were injected into mice ($1\times10^7$)/mice) intravenously into mice vein tail. The tumor size and mice body weight was measured twice a week with calipers, and tumor volume was calculated using the following formula: length×width$^2$/2.

Figure 7:
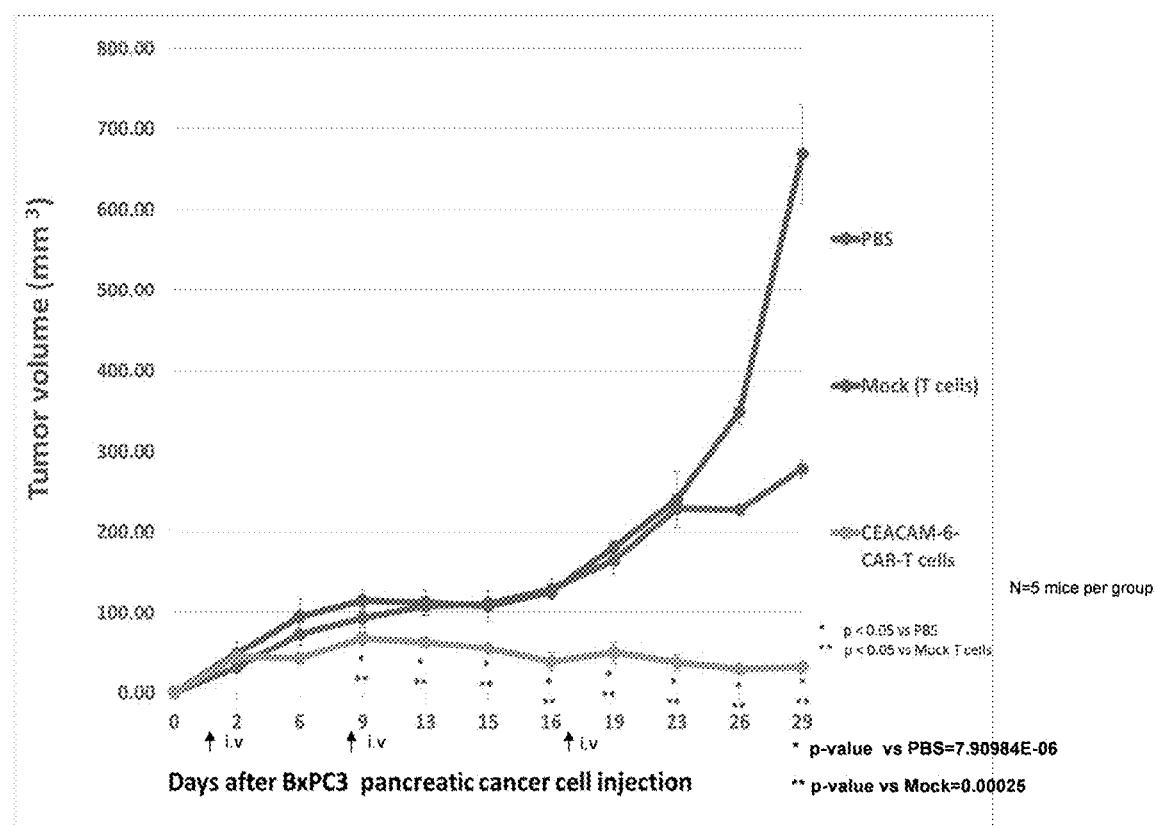
FIG. 7 is a graph showing CEACAM-6 CAR-T cells significantly decreased BxPC3 xenograft tumor growth in vivo. N=5 mice per group. Arrow indicate day of injection (days 1, 8, 15). Mean+/− standard errors are shown. The p-values were calculated and at day 29, the difference was significant with p<0.001 in CAR-T group versus PBS and Control Mock T cell group.

CEACAM-6 CAR-T cells significantly decreased xenograft BxPC3 tumor growth in vivo (p-value versus PBS=7.9E-06; p-value versus Mock control T cells=0.00025, Student's t-test) (FIG. 7).

CEACAM-6 CAR-T Cells Did not Affect Mice Body Weight.

Figure 8:
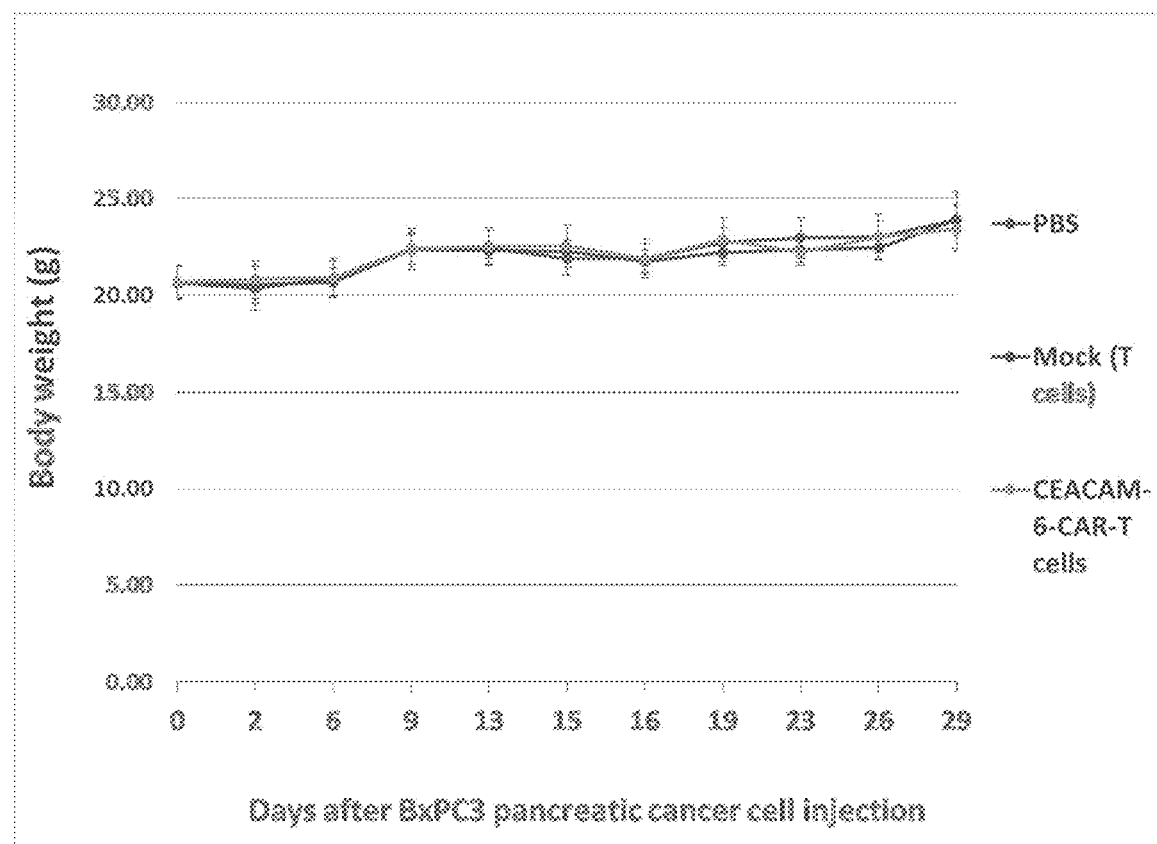
FIG. 8 shows the body weight of mice after injection of CEACAM-6-CAR-T and T cells.

FIG. 8 demonstrates no toxic effect of CEACAM-6-CAR-T cells on mice body weight and all mice were alive after 3 injections of CEACAM-6-CAR-T cells (total $3\times10^7$ cells injected during 3 injections that is equal to $3\times10^{10}$ human dose).

At the end of experiment xenograft tumors were collected for biochemical and genetic analyses.

Figure 9:
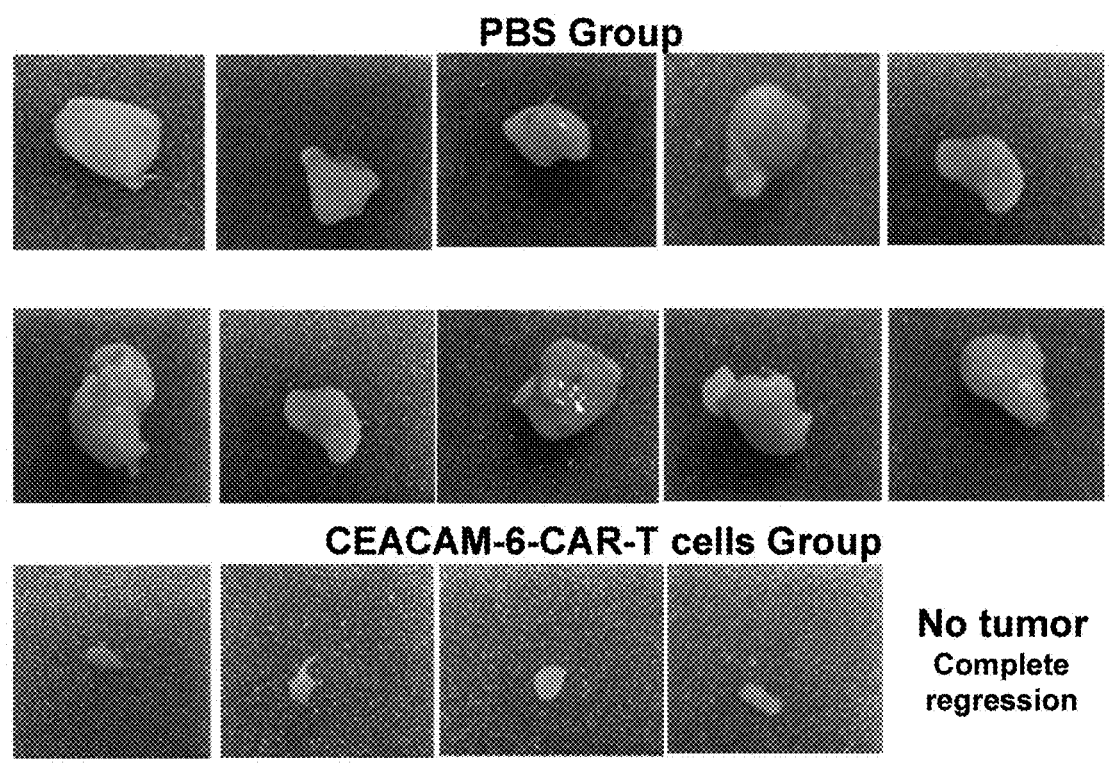
FIG. 9 shows tumors collected at day 30 after BxPC3 cell injection. CEACAM-6-treated mice had significantly decreased tumor sizes and one tumor was completely eliminated.

FIG. 9 demonstrates decreased tumor weight and elimination of one tumor completely in CEACAM-6-treated mice.

CONCLUSION

CEACAM-6-CAR-T cells significantly decrease BxPC3 pancreatic cancer cell growth in vitro and significantly decrease BxPC3 pancreatic cancer xenograft tumor growth in vivo.

The results strongly support that CEACAM-6 can be used as a novel and effective immunotherapy treatment against pancreatic tumors.

Appendix A

A1. Xenograft Tumor Growth in NOG Mice.

TABLE

Study design

| Gp # | Cell line Day 0 | # mice | Treatment Day 1, 8 and 15 | Evaluation |
|---|---|---|---|---|
| 1 | BxPC3 $2\times10^6$ cells in 200 µL, s.c. | 5 | PBS 200 µL by IV, | Daily cage side observations, Tumor measurement and Body Weights twice a week. Tumor burden threshold at |
| 2 | BxPC3 $2\times10^6$ cells in 200 µL, s.c. | 5 | Mock T-cell $1\times10^7$ cells in 200 µL by IV | |

TABLE-continued

Study design

| Gp # | Cell line Day 0 | # mice | Treatment Day 1, 8 and 15 | Evaluation |
|---|---|---|---|---|
| 3 | BxPC3 $2 \times 10^6$ cells in 200 µL, s.c. | 5 | CAR-T1 cells $1 \times 10^7$ cells in 200 µL by IV | 600-1000 mm³. |

Procedure
1) Female, CIEA NOG Mouse® (NOD.Cg-Prkdcscid Il2rgtm1Sug/JicTac) mice 5 weeks of age were obtained from Taconic Bioscience (Hudson, N.Y.).
2) Upon receipt, the mice will be acclimated in the animal facility for 5 days.
3) The BxPC3 cell line is used for injection.
   On the day of implantation (Day 0), BxPC3 cells will be spun down, washed one time with PBS and resuspended in PBS at $2 \times 10^7$ cells per mL.
   Two million cells ($2 \times 10^6$) in 0.10 mL volume are injected s.c.
4) On the day following implantation (Day 1, 8, and 15), PBS, Mock-T, and CAR-T cells are injected vein tail by iv.
   On the day of treatment, Mock-T and CAR-T cells are spun down, washed one time, and resuspended in PBS at $5 \times 10^7$ cells per mL.
   Ten million cells ($1 \times 10^7$) in 0.20 mL volume are injected intravenously via the tail vein.
   i. Group 1 receives PBS.
   ii. Group 2 receives Mock T cell
   iii. Group 3 receives CAR-T cell
5) All animals are observed daily for general activity levels and clinical symptoms of morbidity and ambulatory discomfort. Body weights and tumor measurement are recorded twice a week.
   Tumor volume is calculated in mm³ using the following formula:

(length×width)/2

6) When tumor volume reaches to the endpoint tumor volume (600-1000 mm³), animals are euthanized and tumor is harvested. Upon euthanasia, whole tumor is harvested, stored into tissue cassette, flash frozen, and stored at −80° C.
A2. Statistical Analysis.
The Students t-test was done to measure significant differences between groups. P-value<0.05 was considered significant. At the end of experiment at day 29 of xenograft tumor growth, the significant difference was considered with p-value was <0.001.

Example 4

Figure 10:
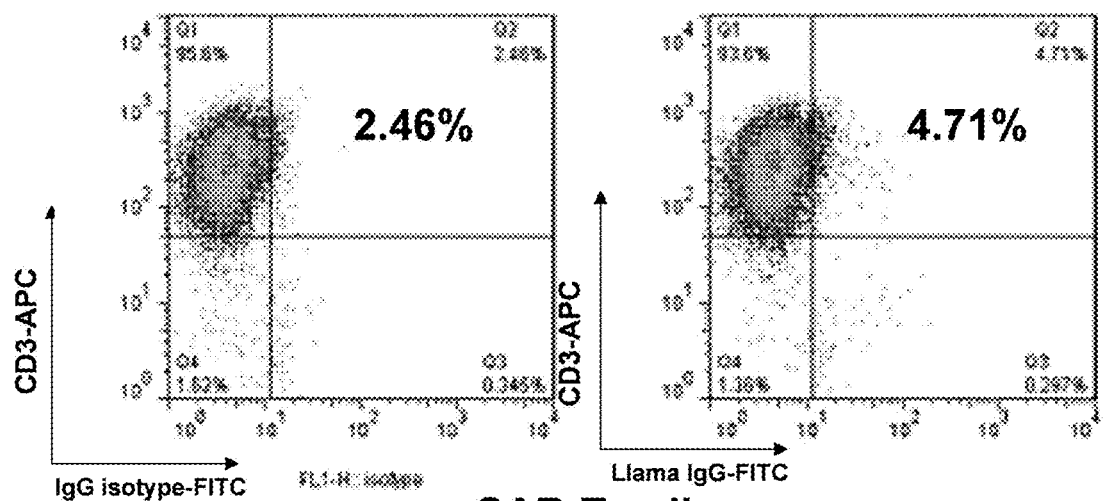
FIG. 10 shows flow cytometry analysis indicating effective transduction of T cells with lentiviral CAR and expression of CEACAM-6 scFv. CD3-APC staining detected a high percent of T cells.
Figure 10:
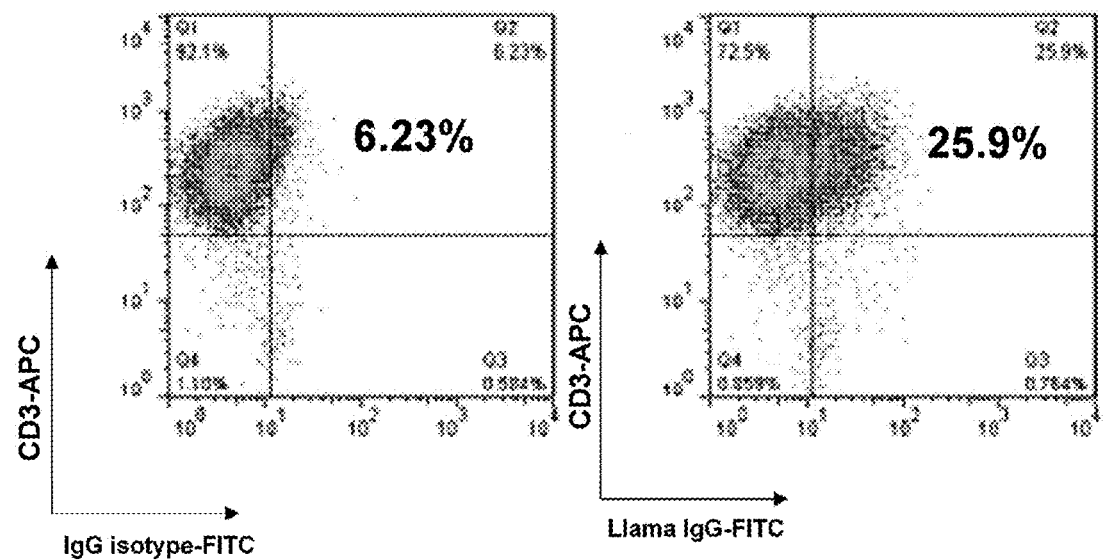

CEACAM6 CAR-T cells were tested against the breast ductal carcinoma HCC1954 cell line, the colon adenocarcinoma LS-174T cell line, and the lung carcinoma A549 cell line in a RTCA (real-time cytotoxic assay) analysis. The BxPC3 pancreatic cancer cell line was used as a positive control. Data show that the anti-CEACAM6 CAR-T is highly effective in all three cell lines analyzed.
CAR-T Cell Generation, Expression of CAR by Flow Cytometry
Freshly prepared CEACAM6 CAR-T cells were expanded for 13 days and used for flow cytometry with anti-llama-antibody, and secondary anti-rabbit-FITC antibody. As shown in FIG. 10, flow cytometry analysis with primary rabbit anti-llama-antibody and isotype IgG negative control, followed by anti-rabbit-FITC antibody staining, showed effective transduction of T cells with lentiviral CAR and expression of CEACAM-6 scFv. CD3-APC staining detected high percent of T cells.
Real-Time Cell Assay (RTCA), CAR-T Cell Cytotoxicity The freshly prepared CAR-T cells expanded for 13 days were used in the RTCA assay. BXPC3 was used as the positive target cell line. Target cells were plated at $1 \times 10^4$ cells per well (of a 96 well plate), and incubated for 24 hr. Anti-CEACAM6 CAR-T cells were used as effector cells, along with non-transduced CAR-T cells as a negative control. CAR-T cells and non-transduced T cells were added to appropriate wells, containing target cells, at a ratio of 10:1 (effector to target cells).

Figure 11:
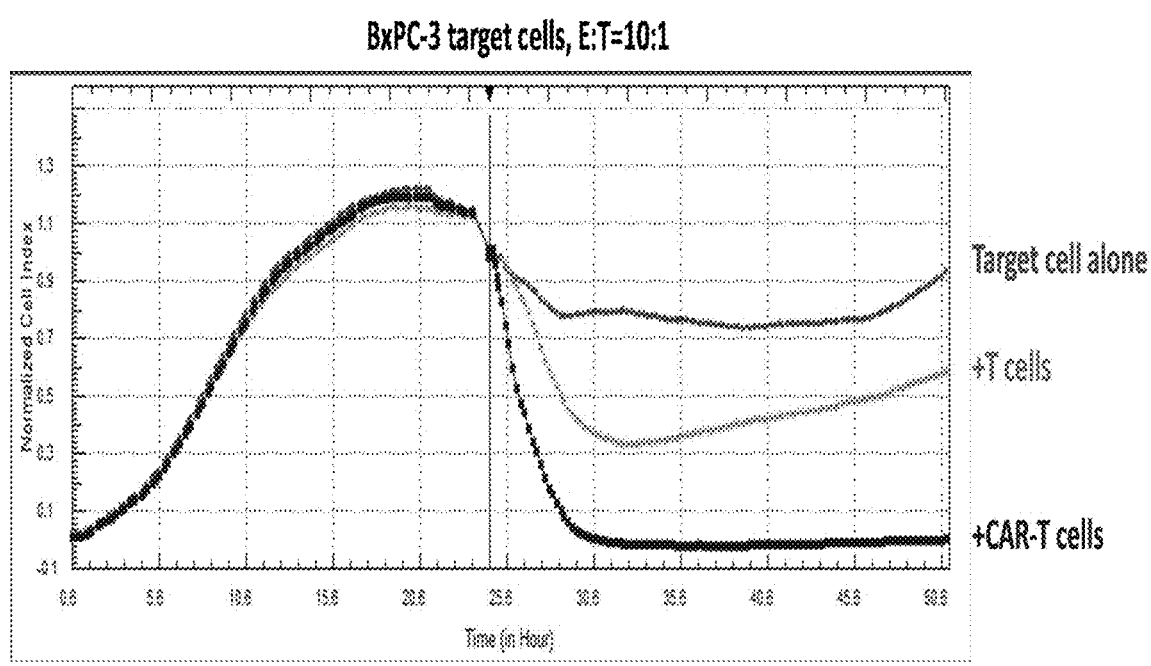
FIG. 11 shows the results of RTCA using pancreatic cancer BXPC3 (CEACAM6 positive) target cells. Effector to target cell ratio was 10:1. Following introduction of effector cells, RTCA data collection proceeded for an additional 26 hours. Data show increased killing of target cells in the presence of CEACAM-6 CAR-T cells.
Figure 12:
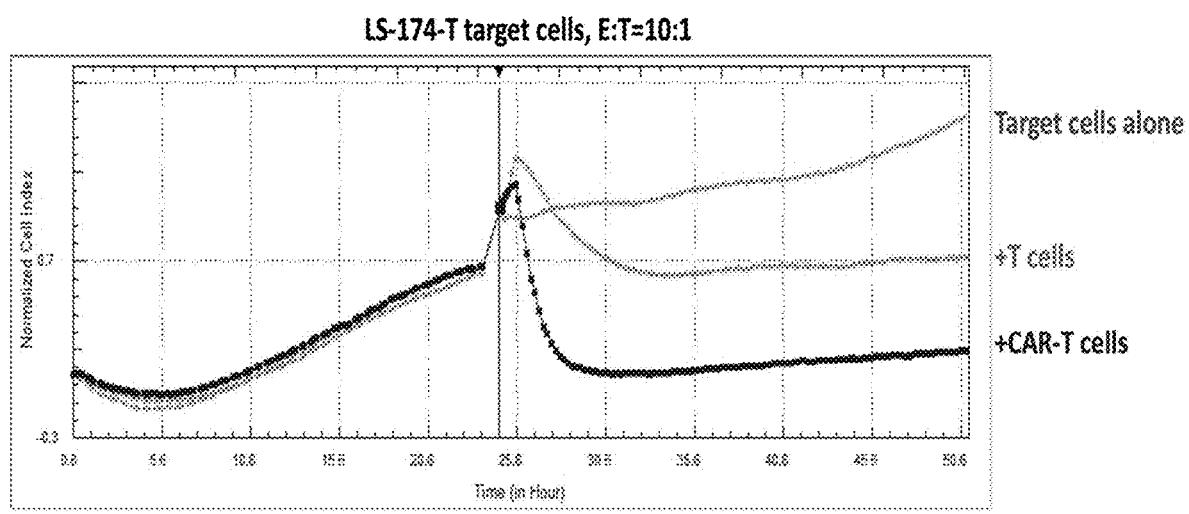
FIG. 12 shows the results of RTCA using colon cancer S174-T (CEACAM6 positive) target cells. Effector to target cell ratio was 10:1. Following introduction of effector cells, RTCA data collection proceeded for an additional 26 hours. Data show increased killing of target cells in the presence of CEACAM-6 CAR-T cells.
Figure 13:
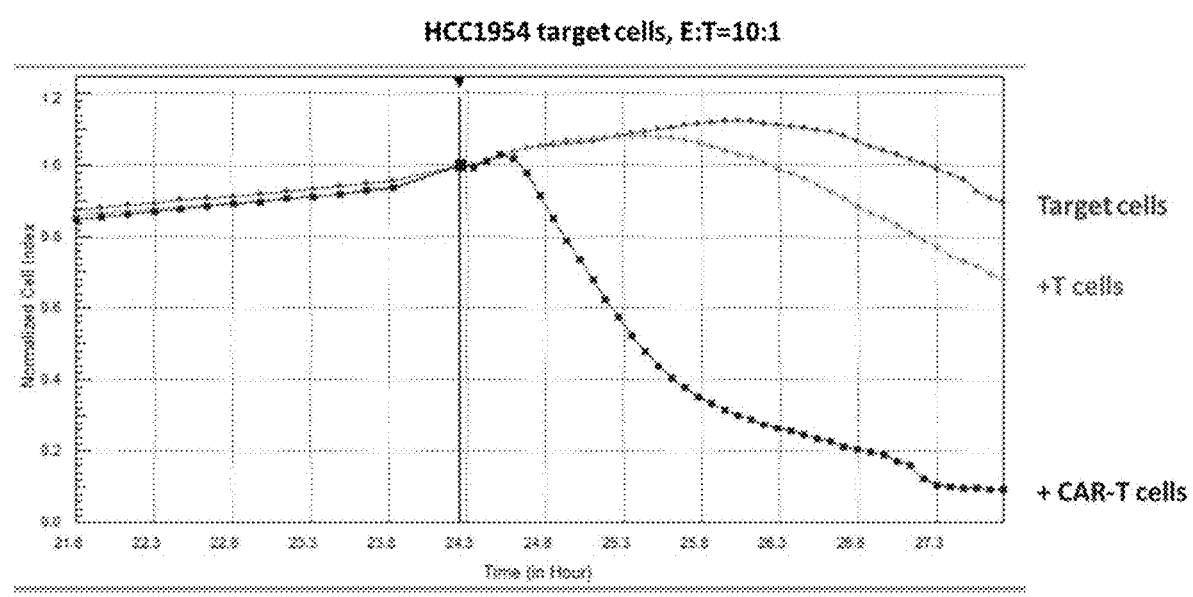
FIG. 13 shows the results of RTCA using breast ductal carcinoma HCC-1954 (CEACAM6 positive) target cells. Effector to target cell ratio was 10:1. Following introduction of effector cells, RTCA data collection proceeded for an additional 26 hours. Data show increased killing of target cells in the presence of CEACAM-6 CAR-T cells.
Figure 14:
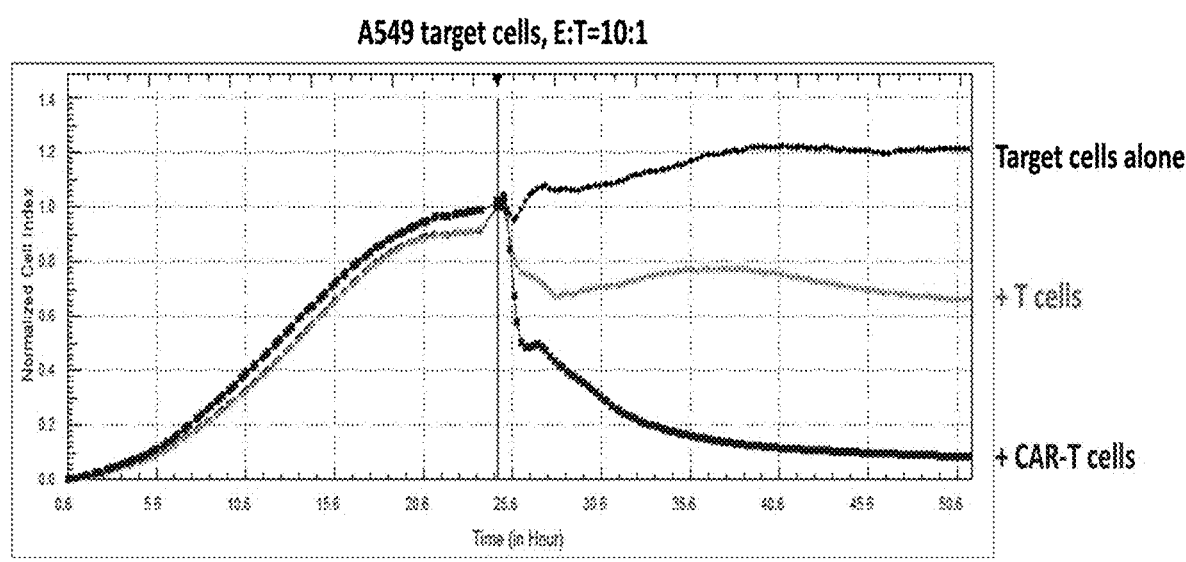
FIG. 14 shows the results of RTCA using lung carcinoma A549 (CEACAM6 positive) target cells. Effector to target cell ratio was 10:1. Following introduction of effector cells, RTCA data collection proceeded for an additional 26 hours. Data show increased killing of target cells in the presence of CEACAM-6 CAR-T cells.

The results for BxPC-3 cells are shown in FIG. 11, the results for LS-174-T cells are shown in FIG. 12, the results for HCC1954 cells are shown in FIG. 13, and the results for A549 cells are shown in FIG. 14. In each instance, it is evident that the CEACAM6 CAR-T cells had a high cytotoxic activity against the cancer cells.

These data show specific and high CEACAM-CAR-T cytotoxic activity against all four cell lines: pancreatic cancer BxPC3; breast cancer HCC1954; colon cancer LS174T and lung cancer A549 cells. All these cancer cell lines can be used as model cells for in vivo studies with CEACAM-CAR-T cells. These data suggest that CEACAM6 CAR-T cells would have cytotoxic activity against any CEACAM6-expressing cancer.

Example 5

The efficacy of CEACAM-6-CAR-T cells in established pancreatic cancer BxPC3 xenografts was tested in vivo. In the examples above, high cytotoxicity of CEACAM-6-CAR-T cells against BxPC3 cells in vitro and in vivo was demonstrated when CAR-T cells were injected for the first time the day after tumor cell injections. In this example, CIEA-NOG mice (Taconic) were used and injected subcutaneously with BxPC3 cells into the hind flank ($2 \times 10^6$ cells/mice). The three groups of mice: PBS; Mock (T cells); and CEACAM-6 CAR-T cells (5 mice per group) were treated at days 12 (when xenograft tumors reached volume 100 mm³), 20, and 26 with intravenous (i.v) injections of either 1×PBS or $1 \times 10^7$ T cells or CAR-T cells.

Figure 15:
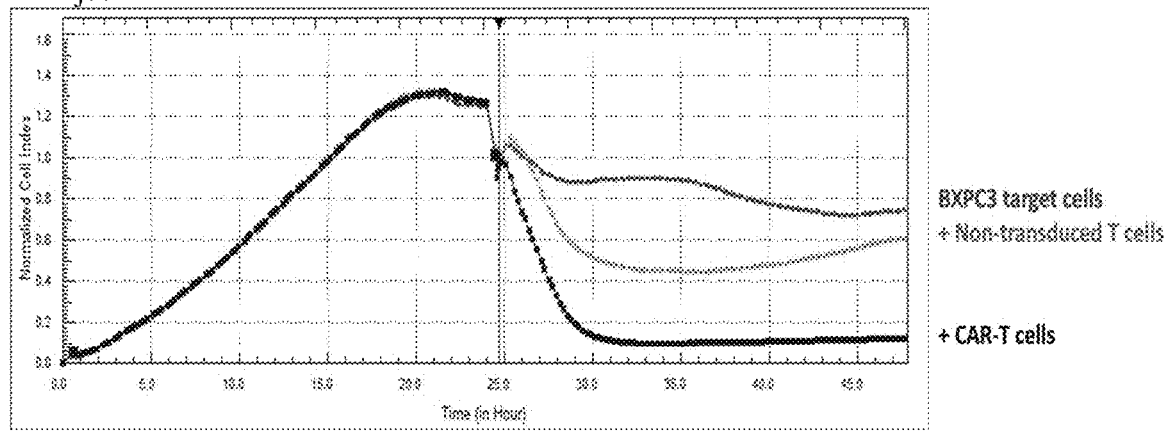
FIG. 15 shows the results of RTCA indicating an enhanced cytotoxic effect of CEACAM-6 CAR-T cells versus target BxPC-3 cells. Ratio of effector:target cells=10:1. T cells and CAR-T cells were added at day 13. A. CAR-T cells used for injection #1. B. CAR-T cells used for injection #2. C. CAR-T cells used for injection #3.
Figure 15:
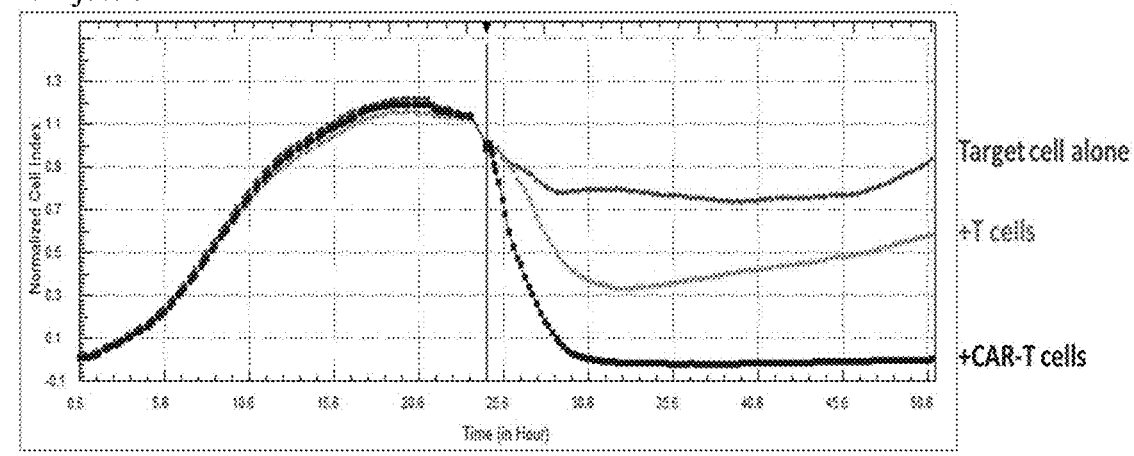
Figure 15:
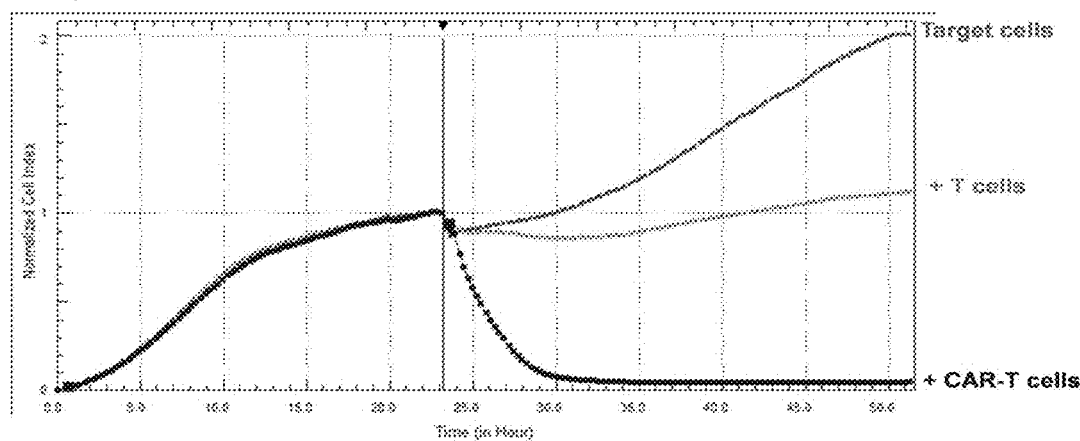
Figure 16:
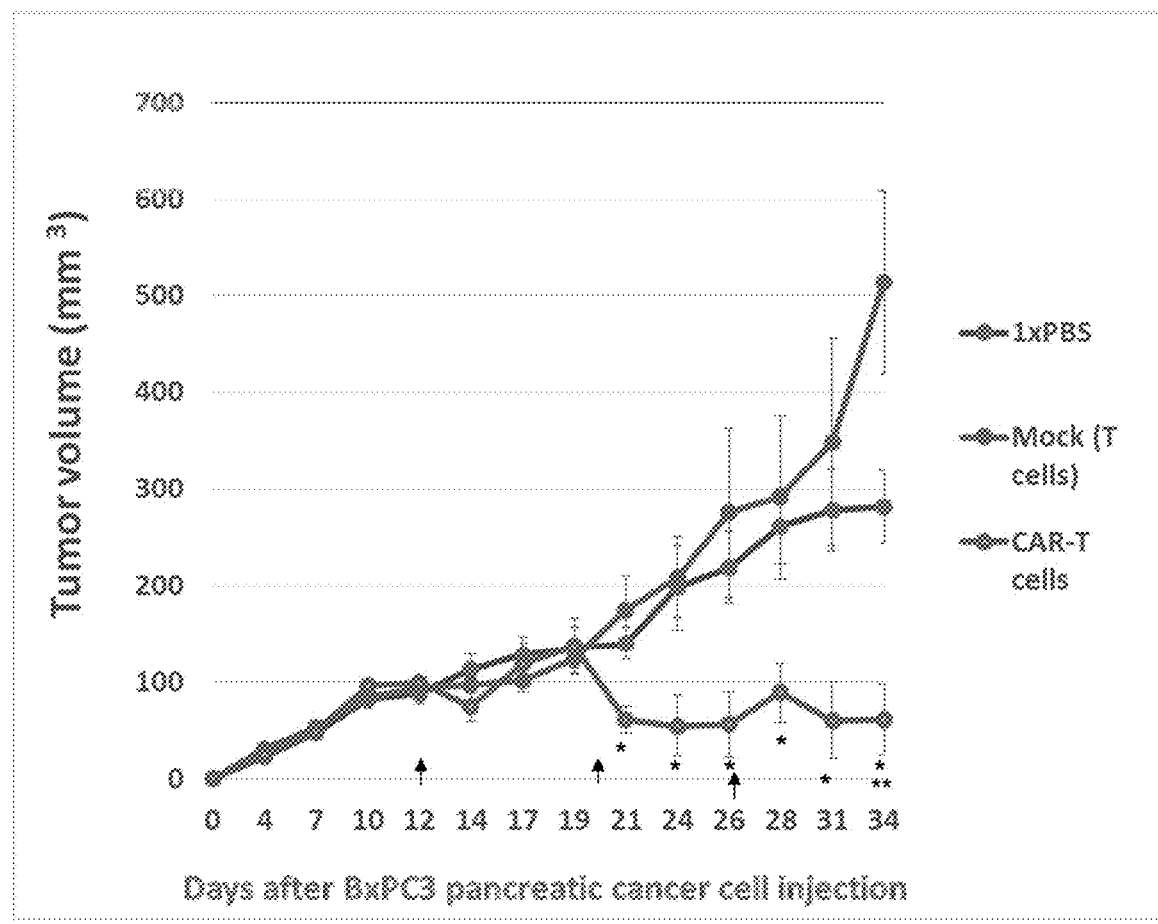
FIG. 16 shows that CEACAM-6 CAR-T cells significantly decreased established BxPC3 xenograft tumor growth in vivo. N=5 mice per group. Arrows indicate day of injection. Mean+/− standard errors are shown.
Figure 17:
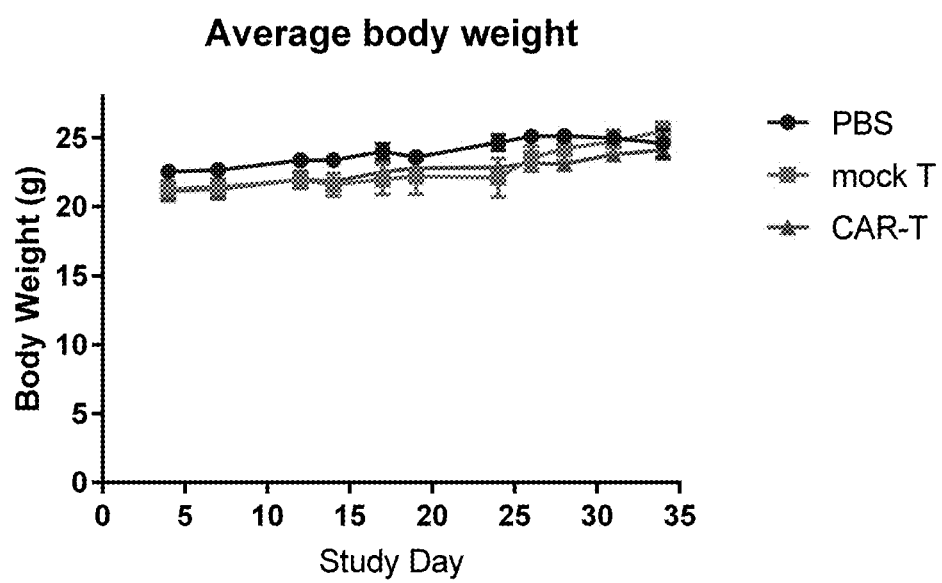
FIG. 17 shows the body weight of mice after injection of PBS, CEACAM-6-CAR-T cells, and T cells.

The data demonstrate very high efficacy of CEACAM-6 CAR-T cells using an established xenograft mouse model. CEACAM-6 CAR-T cells significantly decreased pancreatic cancer cell BxPC3 xenograft tumor growth versus PBS control group (p-value<0.002). The data show high therapeutic potential of CEACAM-6 CAR-T cells against pancreatic cancer and confirm and reproduce the above in vivo study result. These results suggest that the CEACAM-6-CAR-T cells would be useful in future clinical trials and treatment modalities.
RTCA Assay
Cytotoxicity of CEACAM-6-CAR-T cells against BxPC3 target cells was measured by real-time cell analysis (RTCA) for each batch of CAR-T cells (#1, 2 and 3) (FIGS. 15, 16, and 17). The RTCA to date provides reliable data when using adherent cell lines. The target cells were BxPC3 cells and effector cells were CAR-T cells at a ratio of 1:10.

RTCA experimental samples included the following:
(i) Target BxPC3 cells;
(ii) Normal, non-transduced CAR-T cells (negative effector cell control); and
(iii) CEACAM-6-CAR-T cells, human T-cells transduced with CEACAM-6 CAR lentivirus (positive effector cells).

In brief, cells were plated at $1\times10^4$ cells per well 24 hr prior to the introduction of CEACAM-6 CAR-T effector cells. Impedance values across the E-plate were recorded from this point on. Once cells were confluent, wells were washed and appropriate number of CAR-T cells were added at a 10:1 target cell ratio.

Data (FIGS. 15A, B, and C) clearly show a significant increase in BxPC3 cell cytotoxicity by CEACAM-6-CAR-T cells, as compared to the negative control T cells. The control T cells had some cytotoxic activity that was seen previously in some donors.

CEACAM-6 CAR-T Cells Significantly Decreased Established BxPC3 Xenograft Tumor Growth in Vivo CIEA NOG (NOD.Cg-Prkdcscid Il2rgtm1Sug/JicTac) female mice 5 weeks of age were obtained from Taconic Bioscience (Hudson, N.Y.). Pancreatic BxPC3 cancer cells, ($2\times10^6$ cells/mice) were injected subcutaneously into the hind flank of NOG mice. When tumor volume reached 100 mm$^3$, PBS, T cells or CEACAM-6-CAR-T cells were injected ($1\times10^7$/mouse) intravenously into the mouse tail vein at days 12, 20, and 26. The tumor size and mouse body weight were measured twice a week with calipers, and tumor volume was calculated using the following formula: (length×width$^2$)/2.

CEACAM-6 CAR-T cells significantly decreased established xenograft BxPC3 tumor growth in vivo (p-value versus PBS=0.0386, p-value vs mock T cells=0.0005, day 3, 1 way ANOVA with Tukey's multiple comparisons test) (FIG. 16).

CEACAM-6 CAR-T Cells Decreased Tumor Sizes

Figure 18:
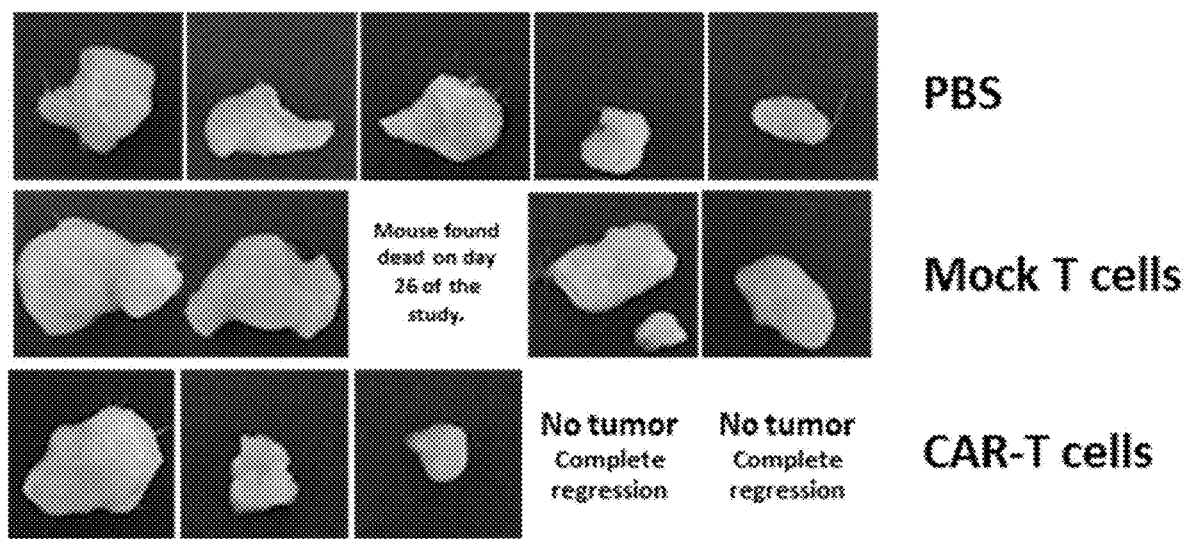
FIG. 18 shows images of tumors collected at day 34 after BxPC3 cell injection. CEACAM-6-treated mice had significantly decreased tumor sizes and two tumors were completely eliminated.

No toxic effects of CEACAM-6-CAR-T cells on mouse body weight were observed (FIG. 17) and all mice were alive after 3 injections of CEACAM-6-CAR-T cells (total $3\times10^7$ cells injected during 3 injections, which is approximately equivalent to a $3\times10^{10}$ human dose). There were no abnormal gross observations in the CEACAM-CAR-T group, while there were in control groups due to tumor growth. As shown in FIG. 18, CEACAM-6 CAR-T treated mice had decreased tumor sizes and elimination of two tumors completely.

CEACAM-6-CAR-T cells significantly decreased BxPC3 pancreatic cancer cell growth in vitro and significantly decreased established BxPC3 pancreatic cancer xenograft tumor growth in vivo. The results, in combination with those above, strongly support that CEACAM-6 can be used as a novel and effective immunotherapy treatment against CEACAM-6-expressing tumors.

The invention claimed is:

1. A chimeric antigen receptor (CAR) comprising or consisting of the sequence:

(SEQ ID NO: 5)
MLLLVTSLLLCELPHPAFLLIPASQVKLEESGGGLVQAGGSLRLSCRTSG

RTNSVYTMGWFRQAPGKEREFVAQIMWGAGTNTHYADSVKGRFTISRDSA

ESTVYLQMNSLKPEDTAVYYCAANRGIPIAGRQYDYWGQGTQVTVSSLEI

EVMYPPPYLDNEKSNGTIIHVKGKHLCPSPLFPGPSKPFWVLVVVGGVLA

CYSLLVTVAFIIFWVRSKRSRLLHSDYMNMTPRRPGPTRKHYQPYAPPRD

FAAYRSRVKFSRSADAPAYQQGQNQLYNELNLGRREEYDVLDKRRGRDPE

MGGKPRRKNPQEGLYNELQKDKMAEAYSEIGMKGERRRGKGHDGLYQGLS

TATKDTYDALHMQALPPR.

2. The CAR of claim 1, wherein the CAR is humanized.

3. An immune cell comprising the CAR of claim 1.

4. The immune cell of claim 3, wherein said cell is a T cell or a cytokine induced killer (CIK) cell.

5. The immune cell of claim 3, further comprising at least a second CAR.

6. The immune cell of claim 3, further comprising a transposon/transposase system.

7. The immune cell of claim 6, wherein the transposon/transposase system is a Sleeping Beauty transposon/transposase system.

8. The immune cell of claim 6, wherein the transposon/transposase system is the SB100X transposon/transposase system.

9. The immune cell of claim 3, further comprising a suicide gene.

10. The immune cell of claim 3, formulated into a composition comprising a pharmaceutically carrier, diluent, and/or excipient; and optionally a chemotherapeutic agent.

11. A method of treating or preventing cancer in a mammal, the method comprising administering the immune cell of claim 3 to the mammal in an amount effective to treat or prevent cancer in the mammal.

12. The method of claim 11, wherein the cancer is a CEACAM6-expressing cancer.

13. The method of claim 12, wherein the cancer is pancreatic cancer, breast cancer, colorectal cancer, lung cancer, gastric cancer, hepatocellular cancer, ovarian cancer or bladder cancer.

14. The method of claim 11, further comprising administration of a chemotherapeutic agent.

15. A chimeric antigen receptor (CAR) specific for binding to CEACAM6, said CAR comprising the sequence:
MLLLVTSLLLCELPHPAFLLIPASQVKLEESGG-
GLVQAGGSLRLSCRTSGRTNSVYTMG
WFRQAPGKEREFVAQIMWGAGTNTHY-
ADSVKGRFTISRDSAESTVYLQMNSLKPEDTA
VYYCAANRGIPI-
AGRQYDYWGQGTQVTVSSLEIEVMYPPPYLD-
NEKSNGTIIHVKGKHL
CPSPLFPGPSKPFWVLVVVGGVLACYSLL-
VTVAFIIFWVRSKRSRLLHSDYMNMTPRRP
GPTRKHYQPYAPPRDFAAYRSRVKFSRSADAPA-
YQQGQNQLYNELNLGRREEYDVLDK
RRGRDPEMGGKPRRKNPQEGLYNELQKDK-
MAEAYSEIGMKGERRRGKGHDGLYQGLS
TATKDTYDALHMQALPPR (SEQ ID NO:5) or a sequence at least 95% identical thereto that retains the activity and specificity of binding to CEACAM6.

16. An immune cell comprising the CAR of claim 15.

17. A chimeric antigen receptor (CAR) specific for binding to CEACAM6, said CAR consisting of the sequence:
MLLLVTSLLLCELPHPAFLLIPASQVKLEESGG-
GLVQAGGSLRLSCRTSGRTNSVYTMG
WFRQAPGKEREFVAQIMWGAGTNTHY-
ADSVKGRFTISRDSAESTVYLQMNSLKPEDTA
VYYCAANRGIPI-
AGRQYDYWGQGTQVTVSSLEIEVMYPPPYLD-
NEKSNGTIIHVKGKHL
CPSPLFPGPSKPFWVLVVVGGVLACYSLL-
VTVAFIIFWVRSKRSRLLHSDYMNMTPRRP
GPTRKHYQPYAPPRDFAAYRSRVKFSRSADAPA-
YQQGQNQLYNELNLGRREEYDVLDK
RRGRDPEMGGKPRRKNPQEGLYNELQKDK-
MAEAYSEIGMKGERRRGKGHDGLYQGLS
TATKDTYDALHMQALPPR (SEQ ID NO:5) or a sequence at least 95% identical thereto that retains the activity and specificity of binding to CEACAM6.

18. An immune cell comprising the CAR of claim 17.

19. The immune cell of claim 16, wherein said immune cell is a T cell or a cytokine induced killer (CIK) cell.

20. The immune cell of claim 18, wherein said immune cell is a T cell or a cytokine induced killer (CIK) cell.

21. The immune cell of claim 19, formulated into a composition comprising a pharmaceutically carrier, diluent, and/or excipient, and optionally a chemotherapeutic agent.

22. The immune cell of claim 20, formulated into a composition comprising a pharmaceutically carrier, diluent, and/or excipient, and optionally a chemotherapeutic agent.

* * * * *